US012709738B2

(12) United States Patent
Genovese et al.

(10) Patent No.: US 12,709,738 B2
(45) Date of Patent: Aug. 18, 2026

(54) COMPOSITIONS AND METHODS FOR INCREASING THE CULTURE DENSITY OF A CELLULAR BIOMASS WITHIN A CULTIVATION INFRASTRUCTURE

(71) Applicant: The Upside Group Inc., Emeryville, CA (US)

(72) Inventors: Nicholas J. Genovese, Hayward, CA (US); Meri Teresa Firpo, Oakland, CA (US); Daphné Dambournet, Berkeley, CA (US)

(73) Assignee: The Upside Group Inc., Emeryville, CA (US)

( * ) Notice: Subject to any disclaimer, the term of this patent is extended or adjusted under 35 U.S.C. 154(b) by 0 days.

(21) Appl. No.: 18/046,083

(22) Filed: Oct. 12, 2022

(65) Prior Publication Data

US 2023/0272346 A1 Aug. 31, 2023

Related U.S. Application Data

(63) Continuation of application No. 16/610,873, filed as application No. PCT/US2018/031276 on May 5, 2018, now Pat. No. 11,976,302.

(60) Provisional application No. 62/502,669, filed on May 6, 2017.

(51) Int. Cl.
*C12N 5/077* (2010.01)
*C07K 14/47* (2006.01)

(52) U.S. Cl.
CPC ........ *C12N 5/0658* (2013.01); *C07K 14/4703* (2013.01); *C12N 5/0656* (2013.01); *C12N 2501/998* (2013.01); *C12N 2511/00* (2013.01)

(58) Field of Classification Search
CPC . C12N 5/0658; C12N 5/0656; C07K 14/4703
See application file for complete search history.

(56) References Cited

U.S. PATENT DOCUMENTS 5,624,840 A 4/1997 Naughton et al.
6,593,275 B1 7/2003 Unkefer et al.
6,767,719 B1 7/2004 Morin et al.
6,835,390 B1 12/2004 Vein
7,033,744 B2 4/2006 Kobayashi et al.
7,147,871 B2 12/2006 Voytik Harbin et al.
7,270,829 B2 9/2007 Van Eelen
8,105,575 B2 1/2012 Kim et al.
8,703,216 B2 4/2014 Forgacs et al.
8,883,502 B2 11/2014 Zhang et al.
9,102,739 B2 8/2015 Lazar et al.
11,479,792 B2 10/2022 Genovese et al.
2002/0068706 A1 6/2002 Gyuris et al.
2005/0260748 A1 11/2005 Chang et al.
2006/0121006 A1 6/2006 Chancellor et al.
2007/0110789 A1 5/2007 Pan
2007/0248716 A1 10/2007 Kruse et al.
2010/0319079 A1 12/2010 Kruse et al.
2011/0091604 A1 4/2011 Miller
2011/0191871 A1 8/2011 Walsh et al.
2011/0225664 A1 9/2011 Smith
2011/0301249 A1 12/2011 Challakere
2012/0202759 A1 8/2012 Pan
2013/0004466 A1 1/2013 Tremblay et al.
2013/0029008 A1 1/2013 Forgacs et al.
2013/0171731 A1 7/2013 Ivashchenko et al.
2013/0224855 A1 8/2013 Gupta et al.
2013/0255003 A1 10/2013 Forgacs et al.
2014/0093618 A1 4/2014 Forgacs et al.
2014/0242155 A1 8/2014 Ramunas et al.
2014/0370537 A1 12/2014 Sakurai et al.
2015/0025128 A1 1/2015 Cain et al.
2015/0079238 A1 3/2015 Marga et al.
2015/0087532 A1 3/2015 Brown et al.
2015/0133520 A1 5/2015 Czech et al.

(Continued)

FOREIGN PATENT DOCUMENTS

CA 2333966 C 12/1999
CA 2780087 A1 12/2012

(Continued)

OTHER PUBLICATIONS

Tokumura et al., Lysophosphatidic acids induce proliferation of cultured vascular smooth muscle cells from rat aorta, Cell Physiology, 267(1): C204-210. (Year: 1994).*
Sinacire et al., Adaptation of Mammalian Cells to Growth in Serum-Free Media, Molecular Biotechnology, 15: 249-257 (Year: 2000).*
Rodríguez-Trelles et al. Is ectopic expression caused by deregulatory mutations or due to gene-regulation leaks with evolutionary potential?, BioEssays 27: 592-601. (Year: 2005).*
Panciera et al., Induction of Expandable Tissue-Specific Stem/Progenitor Cells through Transient Expression of YAP/TAZ, Cell Stem Cell, 19: 725-737 (Year: 2016).*
Stewart et al., Clonal isolation of hESCs reveals heterogeneity within the pluripotent stem cell compartment, Nature Methods, 3(10): 807-815. (Year: 2006).*

(Continued)

*Primary Examiner* — James D Schultz
*Assistant Examiner* — Joseph Paul Miano
(74) *Attorney, Agent, or Firm* — Ballard Spahr LLP

(57) ABSTRACT

Provided herein are methods to increase the culture density and/or thickness of a cellular biomass in a cultivation infrastructure, to improve the culture of cells in the absence of serum in a cultivation infrastructure, and to promote anchorage-independent growth of a cellular biomass in a cultivation infrastructure. The methods comprise inhibiting the HIPPO signaling pathway, for example, by activating YAP1, activating TAZ, and/or inhibiting MOB1, LATS1 kinase, LATS2 kinase, WW45, MST1 kinase, and/or MST2 kinase in the cellular biomass. In some embodiments, the cellular biomass is harvested from the cultivation infrastructure for the formulation of cell-based food products or ingredients, such as animal meat manufactured from cells in an ex vivo process or for therapeutic applications such as organ or tissue transplantation or grafting.

14 Claims, 18 Drawing Sheets

Specification includes a Sequence Listing.

(56) References Cited

U.S. PATENT DOCUMENTS

| | | | |
|---|---|---|---|
| 2015/0216216 | A1 | 8/2015 | Marga |
| 2015/0231209 | A1 | 8/2015 | Hsueh et al. |
| 2015/0289541 | A1 | 10/2015 | Brown et al. |
| 2015/0296834 | A1 | 10/2015 | Geistlinger |
| 2015/0296835 | A1 | 10/2015 | Anderson et al. |
| 2015/0305361 | A1 | 10/2015 | Holz-Schietinger et al. |
| 2015/0305390 | A1 | 10/2015 | Vrljic et al. |
| 2016/0032232 | A1* | 2/2016 | Khan ........................ C12M 1/06 |
| 2016/0227830 | A1 | 8/2016 | Genovese et al. |
| 2016/0251625 | A1 | 9/2016 | Genovese et al. |
| 2017/0101629 | A1 | 4/2017 | Minshull et al. |
| 2017/0114382 | A1 | 4/2017 | Follit et al. |
| 2017/0369849 | A1 | 12/2017 | Hanson et al. |
| 2019/0024079 | A1 | 1/2019 | Genovese et al. |
| 2020/0190524 | A1 | 6/2020 | Minshull et al. |
| 2021/0106032 | A1 | 4/2021 | Leung et al. |
| 2021/0145031 | A1 | 5/2021 | Leung et al. |
| 2021/0171912 | A1 | 6/2021 | Genovese et al. |

FOREIGN PATENT DOCUMENTS

| | | | |
|---|---|---|---|
| CN | 1942576 | A | 4/2007 |
| CN | 101291596 | A | 10/2008 |
| CN | 101624570 | A | 1/2010 |
| EP | 0435617 | A1 | 7/1991 |
| EP | 1037966 | B1 | 5/2003 |
| JP | 2013-81783 | | 5/2013 |
| WO | WO 1993/009236 | A1 | 5/1993 |
| WO | WO 1999/031222 | A1 | 6/1999 |
| WO | WO 1999/031223 | A1 | 6/1999 |
| WO | WO 2006/041429 | A2 | 4/2006 |
| WO | WO 2007/071339 | A1 | 6/2007 |
| WO | WO 2007/077256 | A1 | 7/2007 |
| WO | WO 2010/068897 | A2 | 6/2010 |
| WO | WO 2012/095514 | A1 | 7/2012 |
| WO | WO 2012/170995 | A2 | 12/2012 |
| WO | WO 2012/176023 | A1 | 12/2012 |
| WO | WO 2013/007656 | A1 | 1/2013 |
| WO | WO 2013/016547 | A2 | 1/2013 |
| WO | WO 2013/073246 | A1 | 5/2013 |
| WO | WO 2015/038988 | A1 | 3/2015 |
| WO | WO 2015/066377 | A1 | 5/2015 |
| WO | WO 2015/120174 | A1 | 8/2015 |
| WO | WO 2015/167959 | A1 | 11/2015 |
| WO | WO 2016/052472 | A1 | 4/2016 |
| WO | WO 2016/087560 | A1 | 6/2016 |
| WO | 2016121737 | A1 | 8/2016 |
| WO | WO 2017/019125 | A1 | 2/2017 |
| WO | WO 2017/120089 | A1 | 7/2017 |
| WO | WO 2017/124100 | A1 | 7/2017 |
| WO | WO 2018/208628 | A1 | 11/2018 |
| WO | WO 2019/014652 | A1 | 1/2019 |

OTHER PUBLICATIONS

Lee et al., Clonal Isolation of Muscle-derived Cells Capable of Enhancing Muscle Regeneration and Bone Healing, The Journal of Cell Biology, 150(5): 1085-1099. (Year: 2000).*

Moritz et al., Alternatives for large-scale production of cultured beef: A review, Journal of Integrative Agriculture, 14(2): 208-216. (Year: 2015).*

Fluri, et al., Derivation, expansion and differentiation of induced pluripotent stem cells in continuous suspension cultures, Nature Methods, 9(5): 509-516, including supplement. (Year: 2012).*

Santos et al., Screening for YAP Inhibitors Identifies Statins as Modulators of Fibrosis, Am J Respir Cell Mol Biol, 62(4): 479-492. (Year: 2020).*

Ensembl, mouse Yap1, retrieved from internet Aug. 1, 2024. (Year: 2024).*

Choe et al., Human embryonic stem cell-specific role of YAP in maintenance of self-renewal and survival, Cellular and Molecular Life Sciences, 79 (544): 1-14. (Year: 2022).*

Chen et al., Specific receptor subtype mediation of LPA-induced dual effects in cardiac fibroblasts, FEBS Letters, 580: 4737-4745. (Year: 2006).*

Sheng et al., Lysophosphatidic acid signalling in development, Development, 142: 1390-1395. (Year: 2015).*

Piersman et al., YAP1 Is a Driver of Myofibroblast Differentiation in Normal and Diseased Fibroblasts, The American Journal of Pathology, 185(12): 3326-3337. (Year: 2015).*

Das et al., Selecting the optimal Tet-On system for doxycycline-inducible gene expression in transiently transfected and stably transduced mammalian cells, Biotechnology Journal, 11: 71-79. (Year: 2016).*

Estares et al., YAP repression of the WNT3 gene controls hESC differentiation along the cardiac mesoderm lineage, Genes and Development, 31: 2250-2263. (Year: 2017).*

Shen et al., YAP1 plays a key role of the conversion of normal fibroblasts into cancer-associated fibroblasts that contribute to prostate cancer progression, Journal of Experimental and Clinical Cancer Research, 39(36): 1-16. (Year: 2020).*

Prelich et al., Gene Overexpression: Uses, Mechanisms, and Interpretation, Genetics, 190: 841-854. (Year: 2012).*

United States Office Action, U.S. Appl. No. 17/929,646, Feb. 13, 2023, nine pages.

United States Office Action, U.S. Appl. No. 16/610,873, Feb. 21, 2023, 28 pages.

United States Office Action, U.S. Appl. No. 17/929,652, Mar. 10, 2023, eight pages.

United States Office Action, U.S. Appl. No. 17/929,652, Jun. 27, 2023, nine pages.

Benjaminson, M., et al., "In Vitro Edible Muscle Protein Production System (MPPS): Stage 1, Fish," Acta Astronautica 51 (12), 2002, pp. 879-889.

Bian, W. et al., "Engineered skeletal muscle tissue networks with controllable architecture," Biomaterials, 30, Dec. 12, 2008, pp. 1401-1412.

Broedel, S.E.et al., "The Case for Serum-Free Media," Bio Process International, Feb. 2003, pp. 56-58.

Chen, et al., Homeostatic control of Hippo signaling activity revealed by an endogenous activating mutation in YAP, Genes & Development, 29, Jun. 2015, 1285-1297.

dictionary.com, "myogenic" definition, Date Unknown, one page, [Online] [Retrieved on Aug. 19, 2022] Retrieved from the Internet <URL: https://www.dictionary.com/browse/myogenic>.

Dong, J. et al. "Elucidation of a Universal Size-Control Mechanism in *Drosophila* and Mammals," Cell, vol. 130, No. 6, Sep. 21, 2007, pp. 1120-1133.

European Patent Office, Extended European Search Report and Opinion, EP Patent Application No. 18797874.7, May 21, 2021, 15 pages.

George et al. "Exploiting Expression of Hippo Effector, Yap, for Expansion of Functional Islet Mass," Molecular Endocrinology. Sep. 2015, vol. 29, Iss. 11, pp. 1594-1607.

International Search Report and Written Opinion issued by The International Searching Authority for Application No. PCT/US2018/031276, dated Sep. 10, 2018, 10 pages.

Judson, R.N. et al., "The Hippo Pathway Member Yap Plays a Key Role in Influencing Fate Decisions in Muscle Satellite Cells," Journal of Cell Science, 125, Dec. 2012, pp. 6009-6019.

Kuang, S. et al., "Asymmetric Self-Renewal and Commitment of Satellite Stem Cells in Muscle," Cell, 129, Jun. 1, 2007, pp. 999-1010.

Kucharczak, J. et al., "R-Cadherin Expression Inhibits Myogenesis and Induces Myoblast Transformation via Rac1 GTPase," Cancer Research, vol. 68, No. 16, Aug. 15, 2008, pp. 6559-6568.

Lei, et al., TAZ promotes cell proliferation and epithelial-mesenchymal transition and is inhibited by the hippo pathway, Molecular and Cellular Biology, 28(7): 2426-2436. (Year: 2008).

Mannaerts et al. The Hippo pathway effector YAP controls mouse hepatic stellate cell activation, Journal of Hepatology, 63, Sep. 2015, 679- 688.

(56) References Cited

OTHER PUBLICATIONS

Mckinnon, T. et al., "Kras activation in p53-deficient myoblasts results in high-grade sarcoma formation with impaired mvogenic differentiation," Oncotaraet, vol. 6, No. 16, Jun. 10, 2015, pp. 14220-14232.
Merriam-Webster, "Game" definition, Date Unknown, one page, [Online] [Retrieved on Aug. 19, 2022] Retrieved from the Internet <URL: https://www.merriam-webster.com/dictionary/game>.
Merriam-Webster, "Livestock" definition, Date Unknown, one page, [Online] [Retrieved on Aug. 19, 2022] Retrieved from the Internet <URL: https://www.merriam-webster.com/dictionary/livestock>.
Metzen, E. et al., "Pericellular $P_{O2}$ and $O_2$ consumption in monolayer cell cultures," Respiration Physiology, 100, 1995, pp. 101-106.
Minniti, C.P. et al., "Insulin-like growth factor II overexpression in myoblasts induces phenotypic changes typical of the malignant phenotype," Cell Growth & Differentiation, vol. 6, Mar. 1995, pp. 263-269.
Miranda, A.F. et al., "Transformation of human skeletal muscle cells by simian virus 40," PNAS, vol. 80, Nov. 1983, pp. 6581-6585.
Mohamed, A. et al., "The Hippo effector TAZ (WWTR1) transforms myoblasts and TAZ abundance is associated with reduced survival in embryonal rhabdomyosarcoma," Journal of Pathology, 240, Sep. 2016, pp. 3-14.
Nguyen, H.T. et al., "Viral Small T Oncoproteins Transform Cells by Alleviating Hippo-Pathway-Mediated Inhibition of the YAP Proto-oncogene," Cell Reports, vol. 8, No. 3, Aug. 7, 2014, pp. 707-713.
Overholtzer, M. et al., "Transforming properties of YAP, a candidate oncogene on the chromosome 11a22 amplicon," PNAS, vol. 103, No. 33, Aug. 15, 2006, pp. 12405-12410.
Pandurangan, M. et al., "A novel approach for in vitro meat production," Applied Microbiology and Biotechnology, vol. 99, May 14, 2015, pp. 5391-5395.
Poon et al., The sterile 20-like kinase Tao-1 controls tissue growth by regulating the Salvador-Warts-Hippo pathway, Developmental Cell, 21, Nov. 15, 2011, pp. 896-906.
Powers, D.E. et al., "Accurate Control of Oxygen Level in Cells During Culture on Silicone Rubber Membranes with Application to Stem Cell Differentiation," Biotechnology Progress, 26(3), Dec. 28, 2009, pp. 805-818.
Schutte, U. et al., "Hippo Signaling Mediates Proliferation, Invasiveness, and Metastatic Potential of Clear Cell Renal Cell Carcinoma," Translational Oncology, vol. 7, Iss. 2, Apr. 2014, pp. 309-321.
Watt et al. "Regulation of Tissue Growth by the Mammalian Hippo Signaling Pathway," Frontiers in Physiology. Nov. 24, 2017 (Nov. 24, 2017), vol. B, Article 942, pp. 1-12.
Zeng, Q. et al., "The Emerging Role of the Hippo Pathway in Cell Contact Inhibition, Organ Size Control, and Cancer Development in Mammals," Cancer Cell, vol. 13, Mar. 2008, pp. 188-192.
Zhao, B. et al., "Cell detachment activates the Hippo pathway via cytoskeleton reorganization to induce anoikis," Genes & Development, vol. 26, Jan. 2012, pp. 54-68.
Addgene. "pBABE-hygro-hTERT." Plasmid #1773, Dec. 1998, 6 pages, [Online] [Retrieved Dec. 3, 2020], Retrieved from the Internet <UR: https://www.addgene.org/1773/>.
Addgene. "pBABE-neo-hTERT." Plasmid #1774, Dec. 1998, 5 pages, [Online] [Retrieved Dec. 4, 2020], Retrieved from the Internet <URL: https://www.addgene.org/1774/>.
Albini, S. et al., "Epigenetic Reprogramming of Human Embryonic Stem Cells into Skeletal Muscle Cells and Generation of Contractile Mvospheres," Cell Reports 3:661-670 (2013).
Animal Sake Farm Animals List. downloaded May 24, 2022; on the web at animalsake.com/farm-animals-list. pp. 1-10.
Baquero-Perez et al., "A Simplified but Robust Method for the Isolation of Avian and Mammalian Satellite cells," BMC Cell Biology 13(16): Jan. 2011-Nov. 2011 (2012).
Barberi, T., et al., "Derivation of engraftable skeletal myoblasts from human embryonic stem cells," Nature Medicine 13(5):642-648(2007).
Barnes, et al., Advances in animal cell recombinant protein production: GS-NSO expression system, Cytotechnology 2000, vol. 32, pp. 109-123.
Bartholet, J., "Inside the Meat Lab A Handful Of Scientists Aim to Satisfy the World's Growing Appetite for Steak Without Wrecking The Planet. The First Step: Grab a Petri Dish," Scientific American, pp. 65-69 (2011).
Bell et. al., "Understanding TERT Promoter Mutations: A Common Path to Immortality," Mol Cancer Res 14:315-323 (2016). Published Online First Mar. 3, 2016, retrieved Jul. 6, 2017, from mcr.aacrjournals.org, 10 pages.
Bentzinger, C., et al., "Building Muscle: Molecular Regulation of Myogenesism," Cold Spring Harb Perspect Biol 4(2): 1-16 (2012).
Bernardes De Jesus et. al., "The telomerase activator TA-65 elongates short telomeres and increases health span of adult/old mice without increasing cancer incidence," Aging Cell 10:604-621 (2011).
Bhagavati and Xu., "Generation Of Skeletal Muscle from Transplanted Embryonic Stem Cells in Dvstrophic Mice," Biochemical and Biophysical Research Communications 333:644-649 (2005).
Bhat and Bhat, "Animal-Free Meat Biofabrication," American Journal of Food Technology 6(6):441-459, (2011 ).
Bhat, Z.F. et al., "Prospectus of cultured meat—Advancing meat alternatives," Journal of Food Science and Technology 48(2), Apr. 2010, pp. 125-140.
Black, Brian L., and Eric N. Olson. "Transcriptional control of muscle development by myocyte enhancer factor-2 (MEF2) proteins" Annual review of cell and developmental biology 14.1 (1998): 167-196.
Blomberg et al. Twenty years of embryonic stem cell research in farm animals. Reproduction in Domestic Animals, vol. 47, Suppl. 4, pp. 80-85, Aug. 2012.
Boonen and Post, "The Muscle Stem Cell Niche: Regulation of Satellite Cells During Regeneration," Tissue Engineering—Part B: Reviews 14(4):419-431 (2008).
Canizo et al., "Exogenous human OKSM factors maintain pluripotency gene expression of bovine and porcine iPS-like cells obtained with STEMCCA delivery system," BMC Research Notes vol. 11, Article No. 509, Jul. 2018, 8 pages.
Cenciarelli et al., "Critical Role Played by Cyclin D3 in the Myod-Mediated Arrest of Cell Cycle During Myoblast Differentiation," Molecular and Cellular Biology 19(7):5203-5217 (1999).
Chang, et al., "Generation of Transplantable, Functional Satellite-Like Cells from Mouse Embryonic Stem Cells," FASEB J. 23, 1907-1919 (2009).
Chen et al. DNA methyltransferase inhibitor CDA-11 inhibits myogenic differentiation. Biochemical and Biophysical Research Communications, vol. 422, pp. 522-526, May 22, 2012.
Chen et al., "Potentiation of MyoD1 Activity By 5-Aza-2'-Deoxycytidine," Cell Growth & Differentiation, 1:383-392 (1990).
Chiu and Blau, "5-5Azacytidine Permits Gene Activation in a Previously Noninducible Cell Type," Cell, vol. 40, 417-424 (1985).
Choi, Sang-Woon, and Simonetta Friso. "Epigenetics: a new bridge between nutrition and health" Advances in nutrition 1.1 (2010): 8-16.
Cox et al., "Yap reprograms glutamine metabolism to increase nucleotide biosynthesis and enable liver growth," Nat. Cell. Biol. 18(8), Jan. 18, 2017, pp. 886-896.
Darabi, R., et al, "Perspective Lineage-Specific Reprogramming as a Strategy for Cell Therapy," Cell Cycle 7(12):1732-1737 (2008).
Darabi, R., et al., "Assessment of the Myogenic Stem Cell Compartment Following Transplantation of Pax3/Pax7-Induced Embryonic Stem Cell-Derived Progenitors," Lillehei Heart Institute, Department of Medicine, University of Minnesota, Minneapolis, Mn, USA, 27 pages (2011).
Darabi, R., et al., Functional Skeletal Muscle Regeneration from Differentiating Embryonic Stem Cells, Nature and Medicine 14(2):134-143 (2008).
Datar and Betti, "Possibilities for an In Vitro Meat Production System," Innovative Food Science & Emerging Technologies 11(1):13-22(2010).
Davis, R., et al., "Expression of a Single Transfected cDNA Converts Fibmblasts to Myoblasts," Cell, vol. 51. 987-1000 (1987).

(56) References Cited

OTHER PUBLICATIONS

Dekel, I., et al., "Conditional Conversion of ES Cells to Skeletal Muscle by an Exogenous MyoDI Gene," (1992).
Delany, M. E et al. "Telomeres in the Chicken: Genome Stability and Chromosome Ends." Poultry Science, vol. 82, No. 6, Jun. 1, 2003, pp. 917-926.
Desbois-Mouthon, Christele, et al. "Insulin and IGF-1 stimulate the.beta.-catenin pathway through two signalling cascades involving GSK-3.beta. inhibition and Ras activation" Oncogene 20.2 (2001): 252-259.
Ding, Vanessa MY, et al. "FGF-2 modulates Wnt signaling in undifferentiated hESC and iPS cells through activated PI3-K/GSK3.beta. signaling" Journal of cellular physiology 225.2 (2010): 417-428.
Dominguez et. al., "Beyond editing: repurposing CRISPR-Cas9 for precision genome regulation and interrogation," Nature Reviews Molecular Cell Biology 17:5-15, Dec. 16, 2015.
Edelman, P., et al., "In Vitro-Cultured Meat Production," Tissue Engineering 11(5/6):659-662 (2005).
European Patent Office, Extended European Search Report and Opinion, EP Patent Application No. 18832585.6, Apr. 9, 2021, nine pages.
Extended European Search Report dated May 19, 2017, from the European patent Office for Application No. 14858383.4, filed Oct. 30, 2014, 10 pages.
Fan, L. et al., "The use of glutamine synthetase as a selection marker: recent advances in Chinese hamster ovary cell line generation processes," Pharmaceutical Bioprocessing 1(15), 2013, pp. 487-502.
Garrels et al. Ectopic expression of human telomerase KNA component results 1n increased telomerase activity and elongated telomeres in bovine blastocysts. Biol Reprod. 2012, 87(4):95, 1-7.
Genbank. "Bos Taurus Cyclin-Dependent Kinase 4, mRNA (cDNA Clone MGC: 133903 Image:8041087), Complete CDS." NCBI, GenBank: BC109858.1, Nov. 2005, 2 pages, [Online] [Retrieved Dec. 7, 2020], Retrieved from the Internet <URL:https://www.ncbi.nlm.nih.gov/nuccore/BC109858>.
Genbank. "Gallus Gallus Gallus Telomerase Reverse Transcriptase (TERT) mRNA, Complete CDS." GenBank: NCBI, AY502592.1, 2004, 3 pages, [Online] [Retrieved Dec. 7, 2020], Retrieved from the Internet <URL:https://www.ncbi.nlm.nih.gov/nuccore/AY502592>.
Genovese et al., "Enhanced Development of Skeletal Myotubes from Porcine Induced Pluripotent Stem Cells," Scientific Reports, vol. 7, Feb. 6, 2017, 12 pages.
Gianakopoulos, P., et al., "MyoD Directly Up-regulates Premyogenic Mesoderm Factors during Induction of Skeletal Myogenesis in Stem Cells," The Journal of Biological Chemistry 286(4):2517-2525 (2011).
Good Food Institute, "Deep Dive: Cultivated Meat Cell Lines," Feb. 25, 2021, 13 pages, [Online] [Retrieved on Oct. 25, 2022] Retrieved from the Internet <URL: https://gfi.org/science/the-science-of-cultivated-meat/deep-dive-cultivated-meat-cell-lines/>.
Goudenege, S., et al., "Myoblasts Derived From Normal hESCs and Dystrophic hiPSCs Efficiently Fuse With Existing Muscle Fibers Following Transplantation," Molecular Therapy 20(11):2153-2167 Nov. 2012 (2012).
Hanas et al. Potentiation of myogenesis by 5-azacytidine. Journal of Cell Biology, vol. 91, No. 2, p. 27, Abstract 1051, Nov. 1981.
Harley, "Telomerase is not an oncogene," Oncogene 2002, 21(4):494-502.
He Rong et al., "Expression and clinical significance of p15 protein, mRNA in nasopharyngeal carcinoma," Chinese Journal of Laboratory Diagnosis, vol. 13, No. 5, Jun. 19, 2009, pp. 618-622, (with English abstract).
Hollenberg, S., et al., "Use of a conditional MyoD transcription factor in studies of MyoD trans-activation and muscle determination," Proc. Natl. Acad. Sci. USA vol. 90, pp. 8028-8032 (1993).
Hopkins and Dacey, "Vegetarian meat: Could Technology Save Animals And Satisfy Meat Eaters?" Journal of Agricultural and Environmental Ethics 21(6):579-596 (2008).
Hu, Yang "Exercise molecule biology," Beijing Sport University press, pp. 152-157 (2013) (with the English translation of paragraph 2 on p. 152 to paragraph 1 on p. 157).
Huang et al. "Zfp423 Promotes Adipogenic Differentiation of Bovine Stromal Vascular Cells," PLOS ONE, Oct. 2012, vol. 7, Issue 10, 10 pages.
Hupkes et al. Epigenetics: DNA demethylation promotes skeletal myyotube maturation. The FASEB Journal, vol. 25, No. 11, pp. 3861-3872, Nov. 2011.
Hupkes, Marlinda, et al. "DNA methylation restricts spontaneous multi-lineage differentiation of mesenchymal progenitor cells, but is stable during growth factor-induced terminal differentiation" Biochimica et Biophysica Acta (BBA)—Molecular Cell Research 1813.5 (2011): 839-849.
Hwang, Y., et al., "Directed In Vitro Myogenesis of Human Embryonic Stem Cells and Their In Vivo Engraftment," PLOS ONE e72023 8(8):1-10 (2013).
Iacovino, M., et al., "Inducible Cassette Exchange: A Rapid and Efficient System Enabling Conditional Gene Expression in Embryonic Stem and Primary Cells," Stem Cells 2011;29:1580-1587 (2011).
Iemata, M., et al., "Suppression by Glutamate of Proliferative Activity Through Glutathione Depletion Mediated by the Cystine/Glutamate Anti porter in Mesenchymal C3H10T1/2 Stem Cells," Journal of Cellular Physiology 213:721-729 (2007).
International Preliminary Report on Patentability in corresponding PCT Application No. PCT/US2014/063250, mailed May 3, 2016.
International Search Report and Written Opinion issued by The International Searching Authority for Application No. PCT/US14/63250, dated Jan. 21, 2015, 9 pages.
International Search Report and Written Opinion issued by the International Searching Authority for Application No. PCT/US2017/13782, dated Apr. 10, 2017, 7 pages.
International Search Report and Written Opinion issued by the International Searching Authority for Application No. PCT/US2018/042187, dated Nov. 1, 2018, 16 pages.
Jones, N., "A Taste of Things to Come?" Nature 468:752-753 (2010).
Kadim, I.T. et al., "Cultured meat from muscle stem cells: A review of challenges and prospects," Journal of Integrative Agriculture 14(2), Feb. 2015, pp. 222-233.
Kanzaki et al. 2002; Telomerase rescues the expression levels of keratinocyte growth factor and insulin-like growth factor-II in senescent human fibroblasts. Environmental Cell Research. 279: 321-329.
Knox et al., "A streamlined implementation of the glutamine synthetase-based protein expression system," BMC Biotechnol. Sep. 24, 2013;13:74, 10 pages.
Langelaan, et al., "Meet The New Meat: Tissue Engineered Skeletal Muscle," Trends in Food Science & Technology 21(2):59-66 (2010).
Lassar, A., et al., "Transfection of a DNA Locus That Mediates the Conversion of IOTV2 Fibroblasts to Myoblasts," Cell 47:649-656 (1986).
Lavial et al., "Chicken Embryonic Stem Cells As A Non-Mammalian Embryonic Stem Cell Model," Development, Growth & Differentiation 52:101-1114 (2010).
Lee et al. "Establishment of an immortal chicken embryo liver-derived cell line," 2013 Poultry Science, vol. 92, No. 6, 9 pages.
Leung, M., et al., "Nanofiber-Based in Vitro System for High Myogenic Differentiation of Human Embryonic Stem Cells," Biomacromolecules 14:4207-4216 (2013).
Li et al., "Short-Term Serum-Free Culture Reveals That Inhibition of Gsk3beta Induces the Tumor-Like Growth of Mouse Embryonic Stem Cells," 6(6):1/10-10/10 (2011).
Li, J., "Cultured Meat: Growing Meat in the Lab," Berkeley Scientific Journal, vol. 26, Issue 1, Fall 2021, pp. 67-70.
Lian et al., Directed Cardiomyocyte Differentiation From Human Pluripotent Stem Cells by Modulating WnVBeta-Catenin Signaling Under Fully Defined Conditions. Nature Protocols, 8(1 ): 162-175 (2013).

(56) References Cited

OTHER PUBLICATIONS

Liu et. al., "Linking Telomere Regulation to Stem Cell Pluripotency," Trends in Genetics 33(1), Jan. 2017, 16-33.
Maak et al., "Identification and Analysis of Putative Regulatory Sequences for the MYF5/MYF6 Locus in Different Vertebrate Species," Gene, 379: 141-147 (2006).
Mahmood, A., Enhanced Differentiation of Human Embryonic Stem Cells to Mesenchymal Progenitors by Inhibition ofTGF-beta/ Activin/Nodal Signaling Using SB-431542 Journal of Bone and Mineral Research 25(6):1216-1233 (2010).
Mcfarlane et al., "Myostatin Signals Through Pax? To Regulate Satellite Cell Self-Renewal," Experimental Cell Research 314:317-329 (2008), available online Sep. 2007.
Minzuno, Y., et al., "Generation of Skeletal Muscle Stem/Progenitor Cells from Murine Induced Pluripotent Stem Cells," The FASEB Journal 24:2245-2243 (2010).
Molkentin et al. Cooperative activation of muscle gene expression by MEF2 and myogenic bHLH proteins. Cell, vol. 83, pp. 1125--1136, Dec. 1995.
Munro, et al. Histone deacetylase inhibitors induce a senescence-like state in human cells by a p16-dependent mechanism that is independent of a mitotic clock. Exp Cell Res. 2004 295(2):525-538.
Nagashima et al., "The Hippo Pathway as Drug Targets in Cancer Therapy and Regenerative Medicine," Current Drug Targets, vol. 18, Mar. 2017, pp. 447-454.
Noh et al., "Reduction of ammonia and lactate through the coupling of glutamine synthetase selection and downregulation of lactate dehydrogenase-A in CHO cells," Appl Microbial Biotechnol. Feb. 2017; 101(3): 1035-1045.
Nowak-Lmialek et al. Pluripotent cells in farm animals: state of the art and future perspectives. Reproduction, Fertility and Development, vol. 25, No. 1, pp. 103-108, 2012. (Year: 2012).
Ozasa et al., "Efficient Conversion Of ES Cells into Myogenic Lineage Using the Gene-Inducible System," Biochemical and Biophysical Research Communications 357: 957-963 (2007).
Paredes, C et al., "Modification of glucose and glutamine metabolism in hybrid om a cells through metabolic engineering," Cytotechnology, vol. 30, Jul. 1999, pp. 85-93.
Park et al. "Generation of porcine induced pluripotent stem cells and evaluation of their major histocompatibility complex protein expression in vitro." Veterinary Research Communications, vol. 37, No. 4, pp. 293-301, Dec. 2013, published online Aug. 23, 2013. (Year: 2013).
Post, M., "Cultured beef: Medical Technology to Produce Food," Journal of the Science of Food and Agriculture 94(6), Apr. 2014, pp. 1039-1041.
Post, M., "Cultured Meat from Stem Cells: Challenges and Prospects," Meat Sci. 92(3), Nov. 2012, pp. 297-301.
Rao, L., et al., "Highly Efficient Derivation of Skeletal Myotubes from Human Embryonic Stem Cells," Stem Cell Rev and Rep 8:1109-1119 (2012).
Rezanejad et al., Induced pluripotent stem cells: Progress and future perspectives in the stem cell world. Cellular Reprogramming 14(6), Dec. 2012, pp. 459-470.
Rinkevich, B. Cell cultures from marine invertebrates: New insights for capturing endless sternness. Marine Biotechnology (New York, N.Y.), vol. 13, No. 3, pp. 345-354, Jun. 2011, Epub Jan. 7, 2011.
Rohwedel, J., et al., "Muscle Cell Differentiation of Embryonic Stem Cells Reflects Myogenesis In Vivo: Developmentally Regulated Expression of Myogenic Determination Genes and Functional Expression of Ionic Currents.," Dev Biol. 164(1):87-101 (1994). (Abstract).
Rommel, C., "Mediation of IGF-1-Induced Skeletal Myotube Hypertrophy by PI(3)K/AkVmTOR and PI(3)K/AkVGSK3 Pathways," Nature Cell Biology 3:1009-1013 (2001).
Ryan, T., "Retinoic Acid Enhances Skeletal Myogenesis in Human Embryonic Stem Cells by Expanding the Premyogenic Progenitor Population," Stem Cell Rev and Rep 8, Jun. 2012, pp. 482-493.
Sakurai, H., et al., "Bidirectional Induction Toward Paraxial Mesodermal Derivatives from Mouse ES Cells In Chemically Defined Medium," Stem Cell Research 3:157-169 (2009).
Sakurai, H., et al., "Paraxial Mesodermal Progenitors Derived from Mouse Embryonic Stem Cells Contribute to Muscle Regeneration via Differentiation into Muscle Satellite Cells," Stem Cells 26:1865-1873 (2008).
Salani, S., et al., "Generation Of Skeletal Muscle Cells from Embryonic and Induced Pluripotent Stem Cells As An In Vitro Model and for Therapy of Muscular Dystrophies," J. Cell. Mol. Med. 16(7), Jul. 2012, pp. 1353-1364.
Sasaki, T., et al., "Generation of a Multi-Layer Muscle Fiber Sheet from Mouse ES Cells by the Spermine Action At Specific Timing and Concentration," Differentiation 76, Dec. 2008, pp. 1023-1030.
Schnapp, Esther, et al. "Induced early expression of mrf4 but not myog rescues myogenesis in the myod/myf5 double-morphant zebrafish embryo" Journal of Cell Science 122.4, Feb. 15, 2009, pp. 481-488.
Sharpless, et al. Forging a signature of in vivo senescence. Nature Reviews Cancer, Jul. 2015, 15(7):397-408.
Stadler, G. et al. "Establishment of Clonal Myogenic Cell Lines from Severely Affected Dystrophic Muscles—CDK4 Maintains the Myogenic Population." Skeletal Muscle, vol. 1, Article 12, Mar. 2011, pp. 1-10.
Tako, E. et al. "Using the Domestic Chicken (*Gallus gallus*) as an In Vivo Model for Iron Bioavailability." Poultry Science, vol. 89, No. 3, Mar. 1, 2010, pp. 514-521.
Tan et al., "Efficient Derivation Of Lateral Plate and Paraxial Mseoderm Subtypes From Human Embryonic Stem Cells Through GS Kimediated Differentiation," Stem Cells and Development 22(13), Jul. 2013, pp. 1893-1906.
Tanaka, et al., "Efficient and Reproducible Myogenic Differentiation from Human iPS Cells: Prospects for Modeling Miyoshi Myopathy In Vitro," PLOS ONE e61540 8(4), Apr. 23, 2013, pp. 1-14.
Taylor et al. "Multiple new phenotypes induced in 10T 1 /2 and 3T3 cells treated with 5-azacytidine," Cell 17:771-779 (1979).
Telugu, B., et al., "Leukemia Inhibitory Factor (LIF)-dependent, Pluripotent Stem Cells Established from Inner Cell Mass of Porcine Embryos," Journal of Biological Chemistry, Aug. 2011, 286(33):28948-28953.
Telugu, B., et al., "Lif-Dependent, Pluripotent Stem Cells Established from Inner Cell Mass of Porcine Embryos," The American Society for Biochemistry and Molecular Biology, Inc., Downloaded from www.jbc.org at University of Missouri-Columbia, on Jul. 15, 2011.
Tseng et al. The GSK-3 inhibitor BIO promotes proliferation in mammalian cardiomyocytes. Chemistry & Biology, vol. 13, pp. 957-963, Sep. 2006.
Tuomisto, et al., "Environmental Impacts of Cultured Meat Production," Environ. Sci. Technol. 45(14):6117-6123 (2011).
Van Der Schaft, D., et al., "Engineering Skeletal Muscle Tissues from Murine Myoblast Progenitor Cells and Application of Electrical Stimulation," J. Vis. Exp. 73:1-6 (Mar. 2013).
Van Der Velden, J., et al., "Inhibition of Glycogen Synthase Kinase-3beta-activity is Sufficient To Stimulate Myogenic Differentiation," Am J Physiol Cell Physiol 290: C453-C462, (2006).
Van Der Weele et al. Cultured meat: every village its own factory?, Trends in Biotechnology, Jun. 2014, vol. 32, No. 6, 3 pages.
Van Der Weele, C., "In Vitro Meat," Encyclopedia of Food and Agricultural Ethics, Oct. 2014, pp. 1-8.
Van Der Weele, C., "In Vitro Meat: Promises and Responses: Cooperation Between Science, Social Research And Ethics," Global Food Security: Ethical and Legal Challenges: EurSafe 2010 Bilbao, Spain Sep. 16-18, 2010, pp. 507-512.
Vyas, D., et al., "GSK-3 Negatively Regulates Skeletal Myotube Hypertrophy," Am J Physiol Cell Physiol 283: C545-C551 (2002).
Wagers, A., "Want Not, Waste Not," Cell Stem Cell 2:6-7 (2008).
Wang et. al., "Immortalization of chicken preadipocytes by retroviral transduction of chicken TERT and TR," (2017), PLoS ONE 12(5): e0177348. retrieved May 9, 2017 at https://doi.org/10.1371 /journal.pone.0177348.

(56) References Cited

OTHER PUBLICATIONS

Weintraub et al. Activation of muscle-specific genes in pigment, nerve, fat, liver and fibroblast cell lines by forced expression of MyoD. Proceedings of the National Academy of Sciences, USA, 86:5434-5438 (1989).
West et al. Porcine induced pluripotent stem cells produce chimeric offspring. Stem Cells and Development, vol. 19, No. 8, 2010, pp. 1211-1220, 2010. (Year: 2010).
Wilschut, K., et al., "Alpha 6 Integrin is Important for Myogenic Stem Cell Differentiation," Stem Cell Research 7: 112-123 (2011).
Wilschut, K., et al., "Extracellular Matrix Components Direct Porcine Muscle Stem Cell Behavior," Experimental Cell Research 316:341-352 (2010).
Wilschut, K., et al., "Isolation and Characterization of Porcine Adult Muscle-Derived Progenitor Cells," Journal of Cellular Biochemistry 105: 1228-1239 (2008).
Wootton et al. "Telomerase Alone Extends the Replicative Life Span of Human Skeletal Muscle Cells Without Compromising Genomic Stability," Human Gene Therapy, vol. 14, No. 15, Oct. 10, 2003, 15 pages.
Wu, G., et al., "Production and Supply of High-Quality Food Protein for Human Consumption: Sustainability, Challenges, and Innovations," Annals of the New York Academy of Sciences 1321 (1), Aug. 2014, pp. 1-19.
Xu et al., "Effects of glutamine and asparagine on recombinant antibody production using CHO-GS cell lines," Biotechnol Prog. Nov.-Dec. 2014;30(6):1457-68.
Yokoyama et al., "The Myogenic Transcriptional Network," Cellular and Molecular Life Sciences 68: 1843-1849 (2011).
Yu et al., "Chinese Disease Signal Pathway and Targeted Therapy," Anhui Science and Technology Press, p. 372 (2013) (with the English translation of paragraphs 4-8 on p. 372).
Zheng, J., K., et al., "Skeletal Myogenesis by Human Embryonic Stem Cells," Cell Research 713-722 (2006).
Zhu, C-H. et al. "Cellular Senescence in Human Myoblasts is Overcome by Human Telomerase Reverse Transcriptase and Cyclin-Dependent Kinase 4: Consequences in Aging Muscle and Therapeutic Strategies for Muscular Dystrophies." Aging Cell, vol. 6, No. 4, Aug. 2007, pp. 515-523.
Miki Hideo et al: "Design of serum-free medium for suspension culture of CHO cells on the basis of general commercial media", Cytotechnology, Springer Netherlands, Dordrecht, vol. 67, No. 4, Aug. 23, 2014.
Nguyen Hung Thanh et al: "Viral Small T Oncoproteins Transform Cells by Alleviating Hippo-Pathway-Mediated Inhibition of the YAP Proto-oncogene", Cell Reports, vol. 8, No. 3, Aug. 1, 2014 (Aug. 1, 2014), pp. 707-713.
Chen Yuxuan et al: "Systematic analysis of the Hippo pathway organization and oncogenic alteration in evolution", Scientific Reports, vol. 10, No. 1, Feb. 21, 2020.
Extended European Search Report for European Patent Application No. 24176865.4 dated Nov. 12, 2024.

* cited by examiner

A

B

A

B

A

B

SEQUENCE LISTING

```
Sequence total quantity: 31
SEQ ID NO: 1            moltype = DNA  length = 1464
FEATURE                 Location/Qualifiers
source                  1..1464
                        mol_type = other DNA
                        organism = Homo sapiens
SEQUENCE: 1
atggatcccg ggcagcagcc gccgcctcaa ccggcccccc agggccaagg gcagccgcct  60
tcgcagcccc cgcaggggca gggcccgccg tccggacccg ggcaaccggc acccgcggcg  120
acccaggcgg cgccgcaggc accccccgcc gggcatcaga tcgtgcacgt ccgcggggac  180
tcggagaccg acctggaggc gctctttaac gccgtcatga accccaagac ggccaacgtg  240
ccccagaccg tgcccatgag gctccggaag ctgcccgact ccttcttcaa gccgccggag  300
cccaaatccc actcccgaca ggccagtact gatgcaggca ctgcaggagc cctgactcca  360
cagcatgttc gagctcatgc ctctccagct tctctgcagt tgggagctgt ttctcctggg  420
acactgaccc ccactggagt agtctctggc ccagcagcta cacccacagc tcagcatctt  480
cgacagtctt cttttgagat acctgatgat gtacctctgc cagcaggttg ggagatggca  540
aagacatctt ctggtcagag atacttctta aatcacatcg atcagacaac aacatggcag  600
gaccccagga aggccatgct gtcccagatg aacgtcacag cccccaccag tccaccagtg  660
cagcagaata tgatgaactc ggcttcaggt cctcttcctg atggatggga acaagccatg  720
actcaggatg gagaaattta ctatataaac cataagaaca agaccacctc ttggctagac  780
ccaaggcttg accctcgttt tgccatgaac cagagaatca gtcagagtgc tccagtgaaa  840
cagccaccac ccctggctcc ccagagccca cagggaggcg tcatgggtgg cagcaactcc  900
aaccagcagc aacagatgcg actgcagcaa ctgcagatgg agaaggagag gctgcggctg  960
aaacagcaag aactgcttcg gcaggagtta gccctgcgta gccagttacc aacactggag  1020
caggatggtg ggactcaaaa tccagtgtct tctcccggga tgtctcagga attgagaaca  1080
atgacgacca atagctcaga tcctttcctt aacagtggca cctatcactc tcgagatgag  1140
agtacagaca gtggactaag catgagcagc tacagtgtcc ctcgaacccc agatgacttc  1200
ctgaacagtg tggatgagat ggatacaggt gatactatca accaaagcac cctgccctca  1260
cagcagaacc gtttcccaga ctaccttgaa gccattcctg ggacaaatgt ggaccttgga  1320
acactggaag gagatggaat gaacatagaa ggagaggagc tgatgccaag tctgcaggaa  1380
gctttgagtt ctgacatcct taatgacatg gagtctgttt tggctgccac caagctagat  1440
aaagaaagct ttcttacatg gtta                                        1464

SEQ ID NO: 2            moltype = DNA  length = 1467
FEATURE                 Location/Qualifiers
source                  1..1467
                        mol_type = other DNA
                        organism = Homo sapiens
SEQUENCE: 2
atggatcccg ggcagcagcc gccgcctcaa ccggcccccc agggccaagg gcagccgcct  60
tcgcagcccc cgcaggggca gggcccgccg tccggacccg ggcaaccggc acccgcggcg  120
acccaggcgg cgccgcaggc accccccgcc gggcatcaga tcgtgcacgt ccgcggggac  180
tcggagaccg acctggaggc gctcttcaac gccgtcatga accccaagac ggccaacgtg  240
ccccagaccg tgcccatgag gctccggaag ctgcccgact ccttcttcaa gccgccggag  300
```

```
cccaaatccc actcccgaca ggccagtact gatgcaggca ctgcaggagc cctgactcca  360
cagcatgttc gagctcattc ctctccagct tctctgcagt tgggagctgt ttctcctggg  420
acactgaccc ccactggagt agtctctggc ccagcagcta cacccacagc tcagcatctt  480
cgacagtctt cttttgagat acctgatgat gtacctctgc cagcaggttg ggagatggca  540
aagacatctt ctggtcagag atacttctta aatcacatcg atcagacaac aacatggcag  600
gaccccagga aggccatgct gtcccagatg aacgtcacag cccccaccag tccaccagtg  660
cagcagaata tgatgaactc ggcttcaggt cctcttcctg atggatggga acaagccatg  720
actcaggatg gagaaattta ctatataaac cataagaaca agaccacctc ttggctagac  780
ccaaggcttg accctcgttt tgccatgaac cagagaatca gtcagagtgc tccagtgaaa  840
cagccaccac ccctggctcc ccagagccca cagggaggcg tcatgggtgg cagcaactcc  900
aaccagcagc aacagatgcg actgcagcaa ctgcagatgg agaaggagag gctgcggctg  960
aaacagcaag aactgcttcg gcaggagtta gccctgcgta gccagttacc aacactggag  1020
caggatggtg ggactcaaaa tccagtgtct tctcccggga tgtctcagga attgagaaca  1080
atgacgacca atagctcaga tcctttcctt aacagtggca cctatcactc tcgagatgag  1140
agtacagaca gtggactaag catgagcagc tacagtgtcc ctcgaacccc agatgacttc  1200
ctgaacagtg tggatgagat ggatacaggt gatactatca accaaagcac cctgccctca  1260
cagcagaacc gtttcccaga ctaccttgaa gccattcctg ggacaaatgt ggaccttgga  1320
acactggaag gagatggaat gaacatagaa ggagaggagc tgatgccaag tctgcaggaa  1380
gctttgagtt ctgacatcct taatgacatg gagtctgttt tggctgccac caagctagat  1440
aaagaaagct ttcttacatg gttatag                                    1467

SEQ ID NO: 3            moltype = DNA  length = 1200
FEATURE                 Location/Qualifiers
source                  1..1200
                        mol_type = other DNA
                        organism = Homo sapiens
SEQUENCE: 3
atgaatccgg cctcggcgcc ccctccgctc ccgccgcctg ggcagcaagt gatccacgtc  60
acgcaggacc tagacacaga cctcgaagcc ctcttcaact ctgtcatgaa tccgaagcct  120
agctcgtggc ggaagaagat cctgccggag tctttcttta aggagcctga ttcgggctcg  180
cactcgcgcc agtccagcac cgactcgtcg ggcggccacc cggggcctcg actggctggg  240
ggtgcccagc atgtccgctc gcacgcgtcg cccgcgtccc tgcagctggg caccggcgcg  300
ggtgctgcgg gtagccccgc gcagcagcac gcgcacctcc gccagcagtc ctacgacgtg  360
accgacgagc tgccactgcc cccgggctgg gagatgacct tcacggccac tggccagagg  420
tacttcctca atcacataga aaaaatcacc acatggcaag accctaggaa ggcgatgaat  480
cagcctctga atcatatgaa cctccaccct gccgtcagtt ccacaccagt gcctcagagg  540
tccatggcag tatcccagcc aaatctcgtg atgaatcacc aacaccagca gcagatggcc  600
cccagtaccc tgagccagca gaaccacccc actcagaacc cacccgcagg gctcatgagt  660
atgcccaatg cgctgaccac tcagcagcag cagcagcaga aactgcggct tcagagaatc  720
cagatggaga gagaaaggat tcgaatgcgc caagaggagc tcatgaggca ggaagctgcc  780
ctctgtcgac agctccccat ggaagctgag actcttgccc cagttcaggc tgctgtcaac  840
ccacccacga tgaccccaga catgagatcc atcactaata atagctcaga tcctttcctc  900
aatggagggc catatcattc gagggagcag agcactgaca gtggcctggg gttagggtgc  960
tacagtgtcc ccacaactcc ggaggacttc ctcagcaatg tggatgagat ggatacagga  1020
gaaaacgcag gacaaacacc catgaacatc aatccccaac agacccgttt ccctgatttc  1080
cttgactgtc ttccaggaac aaacgttgac ttaggaactt tggaatctga agacctgatc  1140
cccctcttca atgatgtaga gtctgctctg aacaaaagtg agccctttct aacctggctg  1200

SEQ ID NO: 4            moltype = DNA  length = 1203
FEATURE                 Location/Qualifiers
source                  1..1203
                        mol_type = other DNA
                        organism = Homo sapiens
SEQUENCE: 4
atgaatccgg cctcggcgcc ccctccgctc ccgccgcctg ggcagcaagt gatccacgtc  60
acgcaggacc tagacacaga cctcgaagcc ctcttcaact ctgtcatgaa tccgaagcct  120
agctcgtggc ggaagaagat cctgccggag tctttcttta aggagcctga ttcgggctcg  180
cactcgcgcc agtccagcac cgactcgtcg ggcggccacc cggggcctcg actggctggg  240
ggtgcccagc atgtccgctc gcacgcgtcg cccgcgtccc tgcagctggg caccggcgcg  300
ggtgctgcgg gtagccccgc gcagcagcac gcgcacctcc gccagcagtc ctacgacgtg  360
accgacgagc tgccactgcc cccgggctgg gagatgacct tcacggccac tggccagagg  420
tacttcctca atcacataga aaaaatcacc acatggcaag accctaggaa ggcgatgaat  480
cagcctctga atcatatgaa cctccaccct gccgtcagtt ccacaccagt gcctcagagg  540
tccatggcag tatcccagcc aaatctcgtg atgaatcacc aacaccagca gcagatggcc  600
cccagtaccc tgagccagca gaaccacccc actcagaacc cacccgcagg gctcatgagt  660
atgcccaatg cgctgaccac tcagcagcag cagcagcaga aactgcggct tcagagaatc  720
cagatggaga gagaaaggat tcgaatgcgc caagaggagc tcatgaggca ggaagctgcc  780
ctctgtcgac agctccccat ggaagctgag actcttgccc cagttcaggc tgctgtcaac  840
ccacccacga tgaccccaga catgagatcc atcactaata atagctcaga tcctttcctc  900
aatggagggc catatcattc gagggagcag agcactgaca gtggcctggg gttagggtgc  960
tacagtgtcc ccacaactcc ggaggacttc ctcagcaatg tggatgagat ggatacagga  1020
gaaaacgcag gacaaacacc catgaacatc aatccccaac agacccgttt ccctgatttc  1080
cttgactgtc ttccaggaac aaacgttgac ttaggaactt tggaatctga agacctgatc  1140
cccctcttca atgatgtaga gtctgctctg aacaaaagtg agccctttct aacctggctg  1200
taa                                                              1203

SEQ ID NO: 5            moltype = AA  length = 488
FEATURE                 Location/Qualifiers
source                  1..488
```

```
                        mol_type = protein
                        organism = Homo sapiens
SEQUENCE: 5
MDPGQQPPPQ PAPQGQGQPP SQPPQGQGPP SGPGQPAPAA TQAAPQAPPA GHQIVHVRGD  60
SETDLEALFN AVMNPKTANV PQTVPMRLRK LPDSFFKPPE PKSHSRQAST DAGTAGALTP  120
QHVRAHASPA SLQLGAVSPG TLTPTGVVSG PAATPTAQHL RQSSFEIPDD VPLPAGWEMA  180
KTSSGQRYFL NHIDQTTTWQ DPRKAMLSQM NVTAPTSPPV QQNMMNSASG PLPDGWEQAM  240
TQDGEIYYIN HKNKTTSWLD PRLDPRFAMN QRISQSAPVK QPPPLAPQSP QGGVMGGSNS  300
NQQQQMRLQQ LQMEKERLRL KQQELLRQEL ALRSQLPTLE QDGGTQNPVS SPGMSQELRT  360
MTTNSSDPFL NSGTYHSRDE STDSGLSMSS YSVPRTPDDF LNSVDEMDTG DTINQSTLPS  420
QQNRFPDYLE AIPGTNVDLG TLEGDGMNIE GEELMPSLQE ALSSDILNDM ESVLAATKLD  480
KESFLTWL                                                          488

SEQ ID NO: 6            moltype = AA  length = 488
FEATURE                 Location/Qualifiers
source                  1..488
                        mol_type = protein
                        organism = Homo sapiens
SEQUENCE: 6
MDPGQQPPPQ PAPQGQGQPP SQPPQGQGPP SGPGQPAPAA TQAAPQAPPA GHQIVHVRGD  60
SETDLEALFN AVMNPKTANV PQTVPMRLRK LPDSFFKPPE PKSHSRQAST DAGTAGALTP  120
QHVRAHSSPA SLQLGAVSPG TLTPTGVVSG PAATPTAQHL RQSSFEIPDD VPLPAGWEMA  180
KTSSGQRYFL NHIDQTTTWQ DPRKAMLSQM NVTAPTSPPV QQNMMNSASG PLPDGWEQAM  240
TQDGEIYYIN HKNKTTSWLD PRLDPRFAMN QRISQSAPVK QPPPLAPQSP QGGVMGGSNS  300
NQQQQMRLQQ LQMEKERLRL KQQELLRQEL ALRSQLPTLE QDGGTQNPVS SPGMSQELRT  360
MTTNSSDPFL NSGTYHSRDE STDSGLSMSS YSVPRTPDDF LNSVDEMDTG DTINQSTLPS  420
QQNRFPDYLE AIPGTNVDLG TLEGDGMNIE GEELMPSLQE ALSSDILNDM ESVLAATKLD  480
KESFLTWL                                                          488

SEQ ID NO: 7            moltype = AA  length = 472
FEATURE                 Location/Qualifiers
source                  1..472
                        mol_type = protein
                        organism = Mus musculus
SEQUENCE: 7
MEPAQQPPPQ PAPQGPAPPS VSPAGTPAAP PAPPAGHQVV HVRGDSETDL EALFNAVMNP  60
KTANVPQTVP MRLRKLPDSF FKPPEPKSHS RQASTDAGTA GALTPQHVRA HSSPASLQLG  120
AVSPGTLTAS GVVSGPAAAP AAQHLRQSSF EIPDDVPLPA GWEMAKTSSG QRYFLNHNDQ  180
TTTWQDPRKA MLSQLNVPAP ASPAVPQTLM NSASGPLPDG WEQAMTQDGE VYYINHKNKT  240
TSWLDPRLDP RFAMNQRITQ SAPVKQPPPL APQSPQGGVL GGGSSNQQQQ IQLQQLQMEK  300
ERLRLKQQEL FRQELALRSQ LPTLEQDGGT PNAVSSPGMS QELRTMTTNS SDPFLNSGTY  360
HSRDESTDSG LSMSSYSIPR TPDDFLNSVD EMDTGDTISQ STLPSQQSRF PDYLEALPGT  420
NVDLGTLEGD AMNIEGEELM PSLQEALSSE ILDVESVLAA TKLDKESFLT WL          472

SEQ ID NO: 8            moltype = AA  length = 448
FEATURE                 Location/Qualifiers
source                  1..448
                        mol_type = protein
                        organism = Gallus gallus
SEQUENCE: 8
MDPGQPQPQQ PPQAAQPPAP QQAAPQPPGA GSGAPGGAAQ PPGAGPPPAG HQIVHVRGDS  60
ETDLEALFNA VMNPKGANVP HTLPMRLRKL PDSFFKPPEP KAHSRQASTD AGTAGALTPQ  120
HVRAHSSPAS LQLGAVSPGT LTPSGVVTGP GAPSSQHLRQ SSFEIPDDVP LPPGWEMAKT  180
PSGQRYFLNH IDQTTTWQDP RKAMLSQMNV TAPTSPPVQQ NLMNSASAMN QRISQSAPVK  240
QPPPLAPQSP QGGVMGGSSS NQQQQMRLQQ LQMEKERLRL KHQELLRQEL ALRSQLPTME  300
QDGGSQNPVS SPGMSQELRT MTTNSSDPFL NSGTYHSRDE STDSGLSMSS YSVPRTPDDF  360
LNSVDEMDTG DSISQSNIPS HQNRFPDYLE AIPGTNVDLG TLEGDGMNIE GEELMPSLQE  420
ALSSDILNDM ESVLAATKPD KESFLTWL                                    448

SEQ ID NO: 9            moltype = AA  length = 505
FEATURE                 Location/Qualifiers
VARIANT                 48
                        note = Xaa can be any naturally occurring amino acid
source                  1..505
                        mol_type = protein
                        organism = Sus scrofa
SEQUENCE: 9
MDPGQQQPPP QPAPQGQGQP PAQPPQGQGP PSGPGQPAPP GSQAATQXPP AGHQIVHVRG  60
DSETDLEALF NAVMNPKTAN VPQTVPMRLR KLPDSFFKPP EPKSHSRQAS TDAGTAGALT  120
PQHVRAHSSP ASLQLGAISP GTLTPTGVVS GPAATPTAQH LRQSSFEIPD DVPLPAGWEM  180
AKTSSGQRYF LNHIDQTTTW QDPRKAMLSQ MNVTAPTSPP VQQNMMNSAS GPLPDGWEQA  240
MTQDGEIYYI NHKNKTTSWL DPRLDPRFAM NQRISQSAPV KQPPPLAPQS PQGGVMGGGS  300
SNQQQQMRLQ QLQMEKERLR LKQQELLRQA MRNINPSTAN SPKCQELALR SQLPTLEQDG  360
GTQNPVSSPG MSQELRTMTT NSSDPFLNSG TYHSRDESTD SGLSMSSYSV PRTPDDFLNS  420
VDEMDTGDTI NQSTLPSQQN RFPDYLEAIP GTNVDLGTLE GDGMNIEGEE LMPSLQEALS  480
SDILNDMESV LAATKLDKES FLTWL                                       505

SEQ ID NO: 10           moltype = AA  length = 432
FEATURE                 Location/Qualifiers
```

```
source                1..432
                      mol_type = protein
                      organism = Bos taurus
SEQUENCE: 10
MNPKTANVPQ TVPMRLRKLP DSFFKPPEPK SHSRQASTDA GTAGALTPQH VRAHSSPASL  60
QLGAVSPGTL TPTGVVSGPA AAPAAQHLRQ SSFEIPDDVP LPAGWEMAKT SSGQRYFLNH  120
IDQTTTWQDP RKAMLSQMNV TAPTSPPVQQ NMMNSASGPL PDGWEQAMTQ DGEIYYINHK  180
NKTTSWLDPR LDPRFAMNQR ISQSAPVKQP PPLAPQSPQG GVLGGGSSNQ QQQMRLQQLQ  240
MEKERLRLKQ QELLRQAMRN INPSTANSPK CQELALRSQL PTLEQDGGTQ NPVSSPGMSQ  300
ELRTMTTNSS DPFLNSGTYH SRDESTDSGL SMSSYSVPRT PDDFLNSVDE MDTGDTINQS  360
TLPSQQNRFP DYLEAIPGTN VDLGTLEGDG MNIEGEELMP SLQEALSSDI LNDMESVLAA  420
TKLDKESFLT WL                                                     432

SEQ ID NO: 11         moltype = AA  length = 437
FEATURE               Location/Qualifiers
source                1..437
                      mol_type = protein
                      organism = Oreochromis niloticus
SEQUENCE: 11
MDPSQHNPPA GHQIVHVRGD SETDLEALFN AVMNPKVNTV PHSVPMRMRK LPDSFFKPPE  60
PKSHSRQAST DAGSGGVLIP HHVRAHSSPA SLQLGAVSGG SLSGMGSTGA SPQHLRQSSY  120
EIPDDMPLPD GWEMAKTASG QRYFLNHIDQ TTTWQDPRKA MLQMNQPPPP SSVPVQPQPI  180
MNPASGPLPD GWEQAITAEG EIYYINHKNK TTSWLDPRLE PRYALNQQRI SQSAPVKPPG  240
QLPPSISGVM GSNNQMRLQQ IEKERLRLKQ QELLRQRPQE LALRNQLPTS MDQDGSTNPV  300
SSPMAQDART MTANSSDPFL NSGTYHSRDE STDSGLSMSS YSVPRTPDDF LNSVDEMDTG  360
DPLAPSMATQ PSRFPDYLDT IPGTDVDLGT LEGESMAVEG EELMPSLQEA LSSDILNDME  420
SVLAATKLDK ESFLTWL                                                437

SEQ ID NO: 12         moltype = AA  length = 400
FEATURE               Location/Qualifiers
source                1..400
                      mol_type = protein
                      organism = Homo sapiens
SEQUENCE: 12
MNPASAPPPL PPPGQQVIHV TQDLDTDLEA LFNSVMNPKP SSWRKKILPE SFFKEPDSGS  60
HSRQSSTDSS GGHPGPRLAG GAQHVRSHAS PASLQLGTGA GAAGSPAQQH AHLRQQSYDV  120
TDELPLPPGW EMTFTATGQR YFLNHIEKIT TWQDPRKAMN QPLNHMNLHP AVSSTPVPQR  180
SMAVSQPNLV MNHQHQQQMA PSTLSQQNHP TQNPPAGLMS MPNALTTQQQ QQQKLRLQRI  240
QMERERIRMR QEELMRQEAA LCRQLPMEAE TLAPVQAAVN PPTMTPDMRS ITNNSSDPFL  300
NGGPYHSREQ STDSGLGLGC YSVPTTPEDF LSNVDEMDTG ENAGQTPMNI NPQQTRFPDF  360
LDCLPGTNVD LGTLESEDLI PLFNDVESAL NKSEPFLTWL                       400

SEQ ID NO: 13         moltype = AA  length = 400
FEATURE               Location/Qualifiers
source                1..400
                      mol_type = protein
                      organism = Homo sapiens
SEQUENCE: 13
MNPASAPPPL PPPGQQVIHV TQDLDTDLEA LFNSVMNPKP SSWRKKILPE SFFKEPDSGS  60
HSRQSSTDSS GGHPGPRLAG GAQHVRSHSS PASLQLGTGA GAAGSPAQQH AHLRQQSYDV  120
TDELPLPPGW EMTFTATGQR YFLNHIEKIT TWQDPRKAMN QPLNHMNLHP AVSSTPVPQR  180
SMAVSQPNLV MNHQHQQQMA PSTLSQQNHP TQNPPAGLMS MPNALTTQQQ QQQKLRLQRI  240
QMERERIRMR QEELMRQEAA LCRQLPMEAE TLAPVQAAVN PPTMTPDMRS ITNNSSDPFL  300
NGGPYHSREQ STDSGLGLGC YSVPTTPEDF LSNVDEMDTG ENAGQTPMNI NPQQTRFPDF  360
LDCLPGTNVD LGTLESEDLI PLFNDVESAL NKSEPFLTWL                       400

SEQ ID NO: 14         moltype = AA  length = 395
FEATURE               Location/Qualifiers
source                1..395
                      mol_type = protein
                      organism = Mus musculus
SEQUENCE: 14
MNPSSVPHPL PPPGQQVIHV TQDLDTDLEA LFNSVMNPKP SSWRKKILPE SFFKEPDSGS  60
HSRQSSTDSS GGHPGPRLAG GAQHVRSHSS PASLQLGTGA GAAGGPAQQH AHLRQQSYDV  120
TDELPLPPGW EMTFTATGQR YFLNHIEKIT TWQDPRKVMN QPLNHVNLHP SITSTSVPQR  180
SMAVSQPNLA MNHQHQQVVA TSLSPQNHPT QNQPTGLMSV PNALTTQQQQ QQKLRLQRIQ  240
MERERIRMRQ EELMRQEAAL CRQLPMETET MAPVNTPAMS TDMRSVTNSS SDPFLNGGPY  300
HSREQSTDSG LGLGCYSVPT TPEDFLSNMD EMDTGENSGQ TPMTVNPQQT RFPDFLDCLP  360
GTNVDLGTLE SEDLIPLFND VESALNKSEP FLTWL                            395

SEQ ID NO: 15         moltype = AA  length = 386
FEATURE               Location/Qualifiers
source                1..386
                      mol_type = protein
                      organism = Gallus gallus
SEQUENCE: 15
MNPSPAAPPP GQQVIHITQD LDTELEALFN AVMNPRPSSW RKKILPESFF KEPDSGSHSR  60
QSSTDSGGPP PRPVAAQHVR SHSSPASLVG SAAAPQHGHL RQRSYDVTDE LPLPPGWEMA  120
LTHTGQRYFL NHIEKITTWQ DPRKTMNQPL NHMSHHPAAT STPVPQRSMA MSQPNLVMNH  180
```

-continued

```
QHQITGNTSI SQQSCPSQTP QPGLLNMPSA LTAQQQQQQK LRLQRIQMER ERIRMRQEEL  240
LRQEAALCRQ LPMDSENMTA VQTAVSTAAM TQDMRSITNN GSDPFLNSGP YHSREQSTDS  300
GLGLGCYSIP TTPEDFLSNV DEMDTGETVA QTTVNINAQQ TRFPDFLDCL PGTNVDLGTL  360
ESEDLIPILN DVESVLSKNE PFLTWL                                       386

SEQ ID NO: 16          moltype = AA  length = 399
FEATURE                Location/Qualifiers
VARIANT                129
                       note = Xaa can be any naturally occurring amino acid
source                 1..399
                       mol_type = protein
                       organism = Sus scrofa
SEQUENCE: 16
MNPASAPPPL PPPGQQVIHV TQDLDTDLEA LFNSVMNPKP SSWRKKILPE SFFKEPDSGS  60
HSRQSSTDSS GGHPGPRLAG GAQHVRSHSS PASLQLGTGA GAAGNPAQQH AHLRQQSYDV  120
TDELPLPPXW EMTFTATGQR YFLNHIEKIT TWQDPRKAMN QPLNHMNLHP AATSTPAPQR  180
SMAVSQPNLV MNHHQQQMAP SSLSQQSHPP QNPPAGLMNM PNALTTQQQQ QQKLRLQRIQ  240
MERERIRMRQ EELMRQEAAL CRQLPMEAET LPTVQAAVNP PAMTPDMRSI TNNSSDPFLN  300
GGPYHSREQS TDSGLGLGCY SVPTTPEDFL SNVDEMDTGE NAGPTPMNIN PQQTRFPDFL  360
DCLPGTNVDL GTLESEDLIP LFNDVESALN KSEPFLTWL                         399

SEQ ID NO: 17          moltype = AA  length = 400
FEATURE                Location/Qualifiers
source                 1..400
                       mol_type = protein
                       organism = Bos taurus
SEQUENCE: 17
MNPASAPPPL PPPGQQVIHV TQDLDTDLEA LFNSVMNPKP SSWRKKILPE SFFKEPDSGS  60
HSRQSSTDSS GGHPGPRLAG GAQHVRSHSS PASLQLGTGA GAAVSPAQQH AHLRQQSYDV  120
TDELPLPPGW EMTFTATGQR YFLNHIEKIT TWQDPRKAMN QPLNHMNLHP AATSTPAPQR  180
SMAVSQPNLV MNHQHQQQMA PSSLSQQNHP PQNPSAGLMS MPNALTTQQQ QQQKLRLQRI  240
QMERERIRMR QEELMRQEAA LCRQLPMEAE TLATVQAAVN PPAMTPDMRS ITNNSSDPFL  300
NGGPYHSREQ STDSGLGLGC YSVPTTPEDF LSNVDEMDTG ENTGQTPMNI NPQQTRFPDF  360
LDCLPGTNVD LGTLESEDLI PLFNDVESAL NKSEPFLTWL                        400

SEQ ID NO: 18          moltype = AA  length = 391
FEATURE                Location/Qualifiers
source                 1..391
                       mol_type = protein
                       organism = Danio rerio
SEQUENCE: 18
MSGNPLQPIP GHQVIHVAKD LDTDLEALFN SVMNPKPSSW RNKDMPQSFF QEPDSGSHSR  60
QSSADSGSLP PRVHFRSRSS PASLQLPAGS VSGPSPGRLH SHTRHQSCDV AEELPLPPGW  120
EMAFTPNGQK YFLNHIEKIT TWHDPRKSMT PSVAQLSLHN QVSNTASIQQ RSMALSQPNL  180
VLNQQAHQQQ QQHLQQQQQQ VPVQVPVQAP QQQSSQPMMN LSAQQHQQKM RLQRIQMERE  240
RIQRRQEELM RQEVALRQLP MDSDNLPPVA PAIGSPAMSA GNMPNNSADP FLNSGPYHSR  300
EQSTDSGLGL GCYSIPTTPE DFLNNMEDMD TGENMVPVSM NVPPQSRFPD FLDSMPGTNV  360
DLGTLEGTDL MPILNDVESV LNKSEPFLTW L                                 391

SEQ ID NO: 19          moltype = AA  length = 395
FEATURE                Location/Qualifiers
source                 1..395
                       mol_type = protein
                       organism = Drosophila melanogaster
SEQUENCE: 19
MLTTMSASSN TNSLIEKEID DEDMLSPIKS NNLVVRVNQD TDDNLQALFD SVLNPGDAKR  60
PLQLPLRMRK LPNSFFTPPA PSHSRANSAD STYDAGSQSS INIGNKASIV QQPDGQSPIA  120
AIPQLQIQPS PQHSRLAIHH SRARSSPASL QQNYNVRARS DAAAANNPNA NPSSQQQPAG  180
PTFPENSAQE FPSGAPASSA IDLDAMNTCM SQDIPMSMQT VHKKQRSYDV ISPIQLNRQL  240
GALPPGWEQA KTNDGQIYYL NHTTKSTQWE DPRIQYRQQQ QILMAERIKQ NDVLQTTKQT  300
TTSTIANNLG PLPDGWEQAV TESGDLYFIN HIDRTTSWND PRMQSGLSVL DCPDNLVSSL  360
QIEDNLCSNL FNDAQAIVNP PSSHKPDDLE WYKIN                             395

SEQ ID NO: 20          moltype = DNA  length = 19
FEATURE                Location/Qualifiers
source                 1..19
                       mol_type = other DNA
                       organism = Homo sapiens
SEQUENCE: 20
cagcagcaac agatgcgac                                               19

SEQ ID NO: 21          moltype = DNA  length = 25
FEATURE                Location/Qualifiers
source                 1..25
                       mol_type = other DNA
                       organism = Homo sapiens
SEQUENCE: 21
cagccaaaac agactccatg tcatt                                        25
```

-continued

```
SEQ ID NO: 22          moltype = DNA  length = 20
FEATURE                Location/Qualifiers
source                 1..20
                       mol_type = other DNA
                       organism = Homo sapiens
SEQUENCE: 22
agctcagcat cttcgacagt                                          20

SEQ ID NO: 23          moltype = DNA  length = 22
FEATURE                Location/Qualifiers
source                 1..22
                       mol_type = other DNA
                       organism = Homo sapiens
SEQUENCE: 23
tcaggaagtc atctggggtt cg                                       22

SEQ ID NO: 24          moltype = DNA  length = 31
FEATURE                Location/Qualifiers
variation              7
                       note = note = n is a, c, g, or t
variation              10
                       note = note = n is a, c, g, or t
source                 1..31
                       mol_type = other DNA
                       organism = synthetic construct
SEQUENCE: 24
thacatnrrn cccatgcgca ttaaggtggt c                             31

SEQ ID NO: 25          moltype = DNA  length = 20
FEATURE                Location/Qualifiers
source                 1..20
                       mol_type = other DNA
                       organism = synthetic construct
SEQUENCE: 25
tcgaccggta cgtagtcaca                                          20

SEQ ID NO: 26          moltype = DNA  length = 20
FEATURE                Location/Qualifiers
source                 1..20
                       mol_type = other DNA
                       organism = synthetic construct
SEQUENCE: 26
acctacgaag atggaggcgt                                          20

SEQ ID NO: 27          moltype = DNA  length = 19
FEATURE                Location/Qualifiers
source                 1..19
                       mol_type = other DNA
                       organism = synthetic construct
SEQUENCE: 27
gcgtgttccc tctgaacga                                           19

SEQ ID NO: 28          moltype = DNA  length = 22
FEATURE                Location/Qualifiers
source                 1..22
                       mol_type = other DNA
                       organism = synthetic construct
SEQUENCE: 28
tccgcgttac ataacttacg gt                                       22

SEQ ID NO: 29          moltype = DNA  length = 20
FEATURE                Location/Qualifiers
source                 1..20
                       mol_type = other DNA
                       organism = synthetic construct
SEQUENCE: 29
cccgtgagtc aaaccgctat                                          20

SEQ ID NO: 30          moltype = DNA  length = 20
FEATURE                Location/Qualifiers
source                 1..20
                       mol_type = other DNA
                       organism = synthetic construct
SEQUENCE: 30
aagtacgccc cctattgacg                                          20
```

-continued

```
SEQ ID NO: 31           moltype = DNA  length = 20
FEATURE                 Location/Qualifiers
source                  1..20
                        mol_type = other DNA
                        organism = synthetic construct
SEQUENCE: 31
tacacgccta ccgcccattt                                        20
```

COMPOSITIONS AND METHODS FOR INCREASING THE CULTURE DENSITY OF A CELLULAR BIOMASS WITHIN A CULTIVATION INFRASTRUCTURE

CROSS-REFERENCE TO RELATED APPLICATIONS

This application is a continuation of co-pending U.S. patent application Ser. No. 16/610,873, filed Nov. 4, 2019, which is the 371 National Stage application of PCT Application No. PCT/US2018/031276, filed May 5, 2018, which claims the benefit of and priority to U.S. Provisional Application No. 62/502,669, filed May 6, 2017, the disclosures of each of which are hereby incorporated by reference in their entireties for all purposes.

DESCRIPTION OF THE TEXT FILE SUBMITTED ELECTRONICALLY

The instant application contains a Sequence Listing with 31 sequences, which has been submitted in XML format and is hereby incorporated herein by reference in its entirety. Said XML copy, created on Nov. 28, 2022, is named 39028-53680-002-02-SequenceListing-11-28-2022.xml, and is 41 kilobytes (KB) in size.

BACKGROUND OF THE INVENTION

The mass production of cells remains limited by several factors, thus limiting final yields. Such mass production finds several downstream applications.

For example, foods formulated from metazoan cells, cultured in vitro, have prospective advantages over potential advantages over their corporal-derived animal counterparts, including improved nutrition and safety. Production of these products have been projected to require fewer resources, convert biomass a higher caloric efficiency and result in reduced environmental impacts relative to conventional in vivo methods. Together, metazoan cells, and their extracellular products, constitute a biomass that can potentially be harvested from a cultivation infrastructure for formulation of cell-based food products, such as cultured meat. Cellular biomass produced by cell culture method can also be used in medical applications such as organ or tissue transplant and grafts.

However, mass production of a cellular biomass originating from cultured metazoan cells remains limited by several factors, for example the maximum culture density that can be conventionally achieved, thus limiting final yields. Provided herein are compositions and methods that address this and other related needs.

BRIEF SUMMARY OF THE INVENTION

Provided are compositions and methods for increasing the culture density and thickness of a metazoan cellular biomass (also referred to herein as simply "biomass") in a cultivation infrastructure. These methods comprise inhibiting the HIPPO signaling pathway, for example, by activating Yes-Associated Protein 1 (YAP1) and/or Transcriptional Co-Activator with PDZ-binding motif (TAZ or WWTR1) or homologs thereof, or by inhibiting Mps One Binder kinase activator 1 (MOB1), Large Tumor Suppressor 1 (LATS1) kinase, LATS2 kinase, WW45, Macrophage Stimulating 1 (MST1) kinase, and/or MST2 kinase or homologs thereof in the cellular biomass.

Provided are compositions and methods for increasing the culture density of a cellular biomass in a cultivation infrastructure, for increasing the thickness of a cellular biomass in a cultivation infrastructure, and/or for promoting/increasing anchorage-independent growth of a cellular biomass in a cultivation infrastructure, and/or for promoting/increasing growth of a cellular biomass in a cultivation infrastructure in the absence of serum.

In some embodiments, provided are compositions and methods for increasing cell proliferation, for increasing the culture density of a cellular biomass in a cultivation infrastructure, for increasing the thickness of a cellular biomass in a cultivation infrastructure, and/or for promoting/increasing anchorage-independent growth of a cellular biomass in a cultivation infrastructure in the absence of serum.

In one aspect, provided herein is a method for increasing the thickness of a cellular biomass comprising: (a) culturing a metazoan cellular biomass in a cultivation infrastructure; and (b) inhibiting the HIPPO signaling pathway in the cellular biomass. In another aspect, provided herein is a method for increasing the density of a metazoan cellular biomass comprising: (a) culturing a metazoan cellular biomass in a cultivation infrastructure; and (b) inhibiting the HIPPO signaling pathway in the cellular biomass. In another aspect, provided herein is a method for anchorage-independent cell growth comprising: (a) culturing a metazoan cellular biomass in a cultivation infrastructure; and (b) inhibiting the HIPPO signaling pathway in the cellular biomass.

In some embodiments, inhibiting the HIPPO signaling pathway comprises activating Yes-Associated Protein 1 (YAP1) and/or Transcriptional co-Activator with PDZ-binding motif (TAZ) or homologs thereof in the cellular biomass. In some embodiments, inhibiting the HIPPO signaling pathway comprises inhibiting MOB1, LATS1 kinase, LATS2 kinase, WW45, MST1 kinase, and/or MST2 kinase or homologs thereof in the cellular biomass.

In some embodiments, the inhibiting a HIPPO signaling pathway comprises contacting the cellular biomass with one or more of serum, lysophosphatidic acid, sphingosine-1-phosphate, and thrombin.

In one aspect, the HIPPO signaling pathway is inhibited to provide a culture density of about $10^5$ cells/mL to about $10^{10}$ cells/mL in the cultivation infrastructure. In another aspect, the HIPPO signaling pathway is inhibited to provide a culture density of about 1.0 g/L to about 1000 g/L in the cultivation infrastructure.

In one aspect, the HIPPO signaling pathway is inhibited to provide a thickness of about 10 μm to about 2 mm to cellular biomass in the cultivation infrastructure.

In one aspect, provided herein is a method for increasing the thickness of a cellular biomass comprising: (a) culturing a metazoan cellular biomass in a cultivation infrastructure; and (b) activating Yes-Associated Protein 1 (YAP1) and/or Transcriptional co-Activator with PDZ-binding motif (TAZ) or homologs thereof in the cellular biomass. In another aspect, provided herein is a method for increasing the density of a metazoan cellular biomass comprising: (a) culturing a metazoan cellular biomass in a cultivation infrastructure; and (b) activating Yes-Associated Protein 1 (YAP1) and/or Transcriptional co-Activator with PDZ-binding motif (TAZ) or homologs thereof in the cellular biomass. In another aspect, provided herein is a method for anchorage-independent cell growth comprising: (a) culturing a metazoan cellular biomass in a cultivation infrastructure; and (b) activating Yes-Associated Protein 1 (YAP1) and/or Transcriptional co-Activator with PDZ-binding motif (TAZ) or homologs thereof in the cellular biomass.

In some embodiments, activating YAP1 and/or TAZ comprises contacting the cellular biomass with one or more of serum, lysophosphatidic acid, sphingosine-1-phosphate, and thrombin. In some embodiments, YAP1 and/or TAZ are activated in serum-free conditions. In some embodiments, activating YAP1 and/or TAZ comprises modifying one or more mechanical factors selected from substrate elasticity, substrate rigidity, confinement, stretching, and shear stress.

In some embodiments, activating YAP1 comprises increasing cellular expression of YAP1. In some embodiments, activating TAZ comprises increasing cellular expression of TAZ. In some embodiments, activating YAP1 and TAZ comprises increasing cellular expression of YAP1 and TAZ. In some embodiments, the YAP1 is wild-type YAP1. In some embodiments, the YAP1 comprises one or more mutations in the region targeted by LATS1 and/or LATS2 kinase activity. In some embodiments, the YAP1 comprises one or more mutations at residues corresponding to S5, S61, S109, S127, S163, S164, and 5318 in the human YAP1 protein. In some embodiments, the YAP1 comprises one or more of S5A, S61A, S109A, S127A, S163A, S164A, and S318A mutations, residue numbers corresponding to the human YAP1 protein. In some embodiments, the TAZ is wild-type TAZ. In some embodiments, the TAZ comprises one more mutations in the region targeted by LATS1 and/or LATS2 kinase activity. In some embodiments, the TAZ comprises a mutation at a residue corresponding to S89 in the human TAZ protein. In some embodiments, the TAZ comprises a S89A mutation, the residue number corresponding to the human TAZ protein.

In one aspect, provided herein is a method for increasing the thickness of a cellular biomass comprising: (a) culturing a metazoan cellular biomass in a cultivation infrastructure; and (b) inhibiting MOB1, LATS1 kinase, LATS2 kinase, WW45, MST1 kinase, and/or MST2 kinase or homologs thereof in the cellular biomass. In another aspect, provided herein is a method for increasing the density of a metazoan cellular biomass comprising: (a) culturing a metazoan cellular biomass in a cultivation infrastructure; and (b) inhibiting MOB1, LATS1 kinase, LATS2 kinase, WW45, MST1 kinase, and/or MST2 kinase or homologs thereof in the cellular biomass. In another aspect, provided herein is a method for anchorage-independent cell growth comprising: (a) culturing a metazoan cellular biomass in a cultivation infrastructure; and (b) inhibiting MOB1, LATS1 kinase, LATS2 kinase, WW45, MST1 kinase, and/or MST2 kinase or homologs thereof in the cellular biomass.

In some embodiments, inhibiting MOB1, LATS1 kinase, LATS2 kinase, WW45, MST1 kinase, and/or MST2 kinase or homologs thereof comprises manipulating cells of the cellular biomass to introduce insertion or deletion mutations in the genes encoding these proteins. In some embodiments, inhibiting MOB1, LATS1 kinase, LATS2 kinase, WW45, MST1 kinase, and/or MST2 kinase or homologs thereof comprises over-expressing dominant negative mutants of these proteins in the cells of the cellular biomass.

In some embodiments, the cellular biomass is adherent to a substrate. In some embodiments, the substrate is impermeable. In such embodiments, the biomass thickness is measured as a minimum distance between a basal plane of the cellular biomass and an apical plane of the cellular biomass, e.g. at the region of interest. In some embodiments, the substrate is permeable. In such embodiments, the biomass thickness is measured as half of a minimum distance between a basal plane of the cellular biomass and an apical plane of the cellular biomass, e.g. at the region of interest.

In some embodiments, the cellular biomass is cultured in a suspension culture, and forms a self-adherent aggregate. In such embodiments, the biomass thickness is measured as half a minimum distance between opposing apical planes of the cellular biomass, e.g. at the region of interest. In some embodiments, the cellular biomass is cultured in a suspension culture as a single cell suspension that may remain as a single cell suspension even after increasing the culture density by inhibiting HIPPO signaling or the cellular biomass may start as a single cell suspension and form self-adherent aggregates after increasing the culture density by inhibiting the HIPPO signaling.

In some embodiments, the cellular biomass comprises cells from a livestock, poultry, game, or aquatic species. In some embodiments, the cellular biomass comprises myogenic cells.

In some embodiments, cell proliferation within the cellular biomass is increased through inhibition of HIPPO signaling. In some embodiments, cell survival within the cellular biomass is increased through inhibition of HIPPO signaling. In some embodiments, growth of the cellular biomass (for example, cell number) is increased by inhibiting HIPPO signaling. In some embodiments, cell proliferation, survival and growth are increased within the cellular biomass without addition of serum.

DETAILED DESCRIPTION OF THE INVENTION

Figure 1:
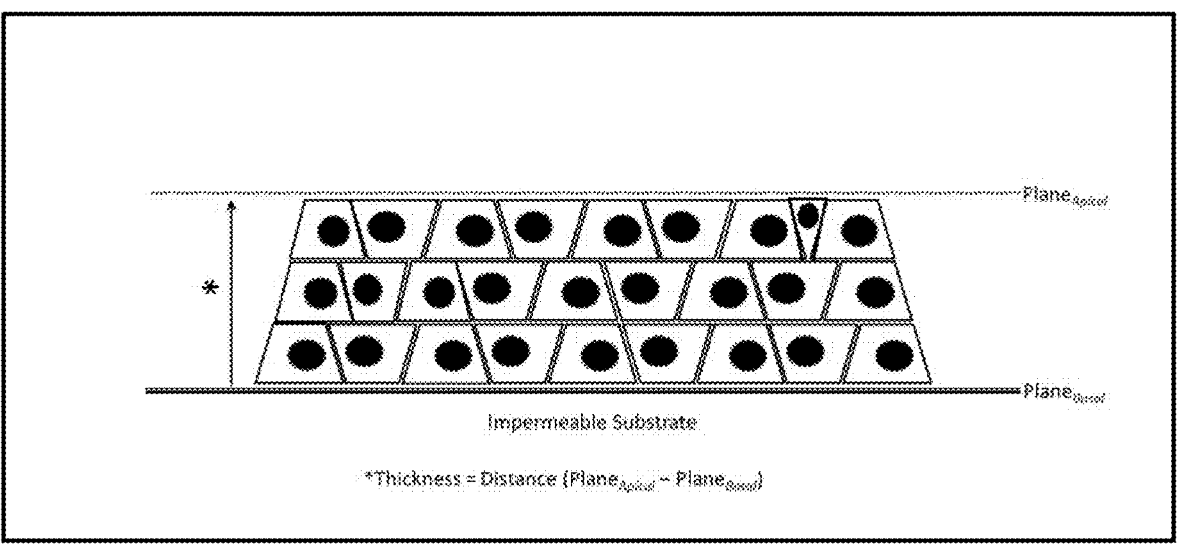
FIG. 1 depicts an exemplary embodiment where a cellular biomass is cultivated on a substrate impermeable to physiological solutions.

Provided are compositions and methods for increasing the density of a metazoan cellular biomass in a cultivation infrastructure; for increasing the thickness of a cellular biomass in a cultivation infrastructure; and for promoting anchorage-independent growth of a cellular biomass in a cultivation infrastructure. These methods comprise inhibiting the HIPPO signaling pathway, e.g. by (a) activating Yes-Associated Protein 1 (YAP1) and/or Transcriptional Co-Activator with PDZ-binding motif (TAZ or WWTR1) or homologs thereof and/or (b) by inhibiting MOB1, LATS1 kinase, LATS2 kinase, WW45, MST1 kinase, and/or MST2 kinase or homologs thereof in the cellular biomass.

Also provided are compositions and methods for increasing proliferation of cells; for increasing the density of a metazoan cellular biomass in a cultivation infrastructure; for increasing the thickness of a cellular biomass in a cultivation infrastructure; and for promoting anchorage-independent growth of a cellular biomass in a cultivation infrastructure without the use of serum.

Also provided are compositions and methods for increasing proliferation of cells; for increasing the density of a metazoan cellular biomass in a cultivation infrastructure; for increasing the thickness of a cellular biomass in a cultivation infrastructure; and for promoting anchorage-independent growth of a cellular biomass in a cultivation infrastructure in the presence of serum.

Also provided are compositions and methods for producing edible metazoan cellular biomass or therapeutic metazoan cellular biomass comprising: (a) culturing a metazoan cellular biomass in a cultivation infrastructure and (b) increasing the density or the thickness of the metazoan cellular biomass in the cultivation infrastructure by inhibiting the HIPPO signaling pathway. The term "edible" cellular biomass as used herein encompasses raw or uncooked metazoan meat as well as partially or fully cooked metazoan meat. The term "therapeutic cellular biomass" or "cellular biomass for therapeutic purposes" as used herein encompasses cells, partial or whole tissue of a metazoan species, cells, partial or whole organ of a metazoan species, or a graft, prepared for and used in therapeutic, medical or cosmetic applications.

Before describing certain embodiments in detail, it is to be understood that this invention is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this invention and in the specific context where each term is used. Certain terms are discussed below or elsewhere in the specification, to provide additional guidance to the practitioner in describing the compositions and methods of the invention and how to make and use them. The scope and meaning of any use of a term will be apparent from the specific context in which the term is used. As such, the definitions set forth herein are intended to provide illustrative guidance in ascertaining particular embodiments of the invention, without limitation to particular compositions or biological systems.

As used in the present disclosure and the appended claims, the singular forms "a," "an" and "the" include plural references unless the content clearly dictates otherwise.

Throughout the present disclosure and the appended claims, unless the context requires otherwise, the word "comprise", or variations such as "comprises" or "comprising", will be understood to imply the inclusion of a stated element or group of elements but not the exclusion of any other element or group of elements.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery.

Cellular Biomass

As referred to herein, a cellular biomass is comprised of metazoan cells and their extracellular products. The cells can be primary cells, or cell lines. The methods provided herein are applicable to any metazoan cell in culture.

In some embodiments, the cellular biomass is harvested for the formulation of cell-based food products, such as cultured animal meat. The term "cultured meat" as used herein refers to uncooked or cooked meat produced using cell culture methods. In some embodiments, the methods utilize cells with the potential to differentiate into skeletal muscle.

In some embodiments, the cellular biomass is harvested for the formulation of cell-based therapeutic products, such as cultured cells, tissue, graft, or whole or part of an organ. Thus in some embodiments, the methods utilize cells with various lineages or sources. For example, the methods may utilize cells from heart, liver, kidney, pancreas, spleen, bladder, intestine, skin, embryo etc.

In certain embodiments, the cellular biomass comprises cells that are from livestock such as domestic cattle, pigs, sheep, goats, camels, water buffalo, rabbits and the like. In certain embodiments, the cellular biomass comprises cells that are from poultry, e.g. domesticated poultry, such as chicken, turkeys, ducks, geese, pigeons and the like. In certain embodiments, the cellular biomass comprises cells that are from game species such as wild deer, gallinaceous fowl, waterfowl, hare and the like. In certain embodiments, the cellular biomass comprises cells that are from aquatic species or semi-aquatic species, including certain fish, crustaceans, mollusks, cephalopods, cetaceans, crocodilians, turtles, frogs and the like. In certain embodiments, the cellular biomass comprises cells that are from exotic, endangered, conserved or extinct animal species. In certain embodiments, the cellular biomass comprises cells that are from any metazoan species demonstrating the capacity for skeletal muscle tissue specification. In certain embodiments, the cellular biomass comprises cells that are modifiable by a genetic switch to induce rapid and efficient conversion of the cells to skeletal muscle for cultured meat production. In certain embodiments, the cellular biomass comprises cells that are from any metazoan species whose tissues are suitable for dietary consumption.

In specific embodiments, the cellular biomass comprises cells from *Gallus gallus, Bos taurus, Sous scrofa, Meleagris gallopavo, Anas platyrynchos, Salmo salar, Thunnus thynnus, Ovis aries, Coturnix coturnix, Capra aegagrus hircus*, or *Homarus americanus*.

In an exemplary embodiment, the cellular biomass comprises cells from livestock, poultry, game, or aquatic species.

In other embodiments, the cellular biomass comprises cells from humans, primates, rodents, including rats and mice, and companion animals such as dogs, cats, horses, and the like.

It is noted that the cellular biomass can be cultivated for any downstream application, not just limited to food production. For example, the cellular biomass can be cultivated for generating cells, a tissue or graft for therapeutic applications.

In some embodiments, the cells of the cellular biomass are primary stem cells or self-renewing stem cell lines.

In some embodiments, the cells of the cellular biomass are myoblasts, myocytes, fibroblasts, induced pluripotent stem cells, hepatocytes, mesenchymal stem cells, adipocytes, embryonic stem cells or chondrocytes.

In some embodiments, the cells of the cellular biomass are myogenic cells. In some embodiments, the cells are natively myogenic (e.g. are myogenic cells such as myoblasts, myocytes, satellite cells, side population cells, muscle derived stem cells, mesenchymal stem cells, myogenic pericytes, and mesoangioblasts that are cultured in the cultivation infrastructure). In other embodiments, the cells are not natively myogenic (e.g. are non-myogenic cells such as fibroblasts or non-myogenic stem cells that are cultured to become myogenic cells in the cultivation infrastructure).

In some embodiments, the cells of the cellular biomass are somatic cells. In some embodiments, the cells of the cellular biomass are not somatic cells.

In some embodiments, the cellular biomass comprises cells of the skeletal muscle lineage. Cells of the skeletal muscle lineage include myoblasts, myocytes, and skeletal muscle progenitor cells, also called myogenic progenitors, that include satellite cells, side population cells, muscle derived stem cells, mesenchymal stem cells, myogenic pericytes, and mesoangioblasts.

In some embodiments, the cellular biomass is cultivated in a suspension culture and forms a self-adherent aggregate. A self-adherent aggregate refers to masses of viable cells suspended in a physiological liquid medium (e.g. suspension culture) aggregated due to, for example, their (1) adherence to each other (e.g. cadherin cell adhesion) (2) adherence to a basement membrane or other extracellular matrix secreted by the cells (e.g. integrin cell adhesion) or (3) a combination of both.

Cultivation Infrastructure

As referred to herein, a cultivation infrastructure refers to the environment in which metazoan cells are cultured, i.e. the environment in which the cellular biomass is cultivated.

A cultivation infrastructure may be a tube, a cylinder, a flask, a petri-dish, a multi-well plate, a dish, a vat, an incubator, a bioreactor, an industrial fermenter and the like.

A cultivation infrastructure can be of any scale, and support any volume of cellular biomass and culturing reagents. In some embodiments, the cultivation infrastructure ranges from about 10 μL to about 100,000 L. In exemplary embodiments, the cultivation infrastructure is about 10 μL, about 100 μL, about 1 mL, about 10 mL, about 100 mL, about 1 L, about 10 L, about 100 L, about 1000 L, about 10,000 L, or even about 100,000 L.

In some embodiments, the cultivation infrastructure comprises a substrate. A cultivation infrastructure may comprise a permeable substrate (e.g. permeable to physiological solutions) or an impermeable substrate (e.g. impermeable to physiological solutions).

In some embodiments, the cultivation infrastructure comprises a primary substrate, which can be a flat, concave, or convex substrate. In some embodiments, the cultivation infrastructure further comprises a secondary substrate, either introduced, or autologous, to direct cellular growth between the substrates, e.g. to direct attachment, proliferation and hypertrophy of cells on a plane perpendicular to the primary substrate.

In some embodiments, the cultivation infrastructure comprises a hydrogel, a liquid cell culture media, or soft agar.

In some embodiments, the cultivation infrastructure does not comprise a substrate to which cells can adhere. In some embodiments, the cultivation infrastructure comprises a suspension culture, e.g. supporting the growth of a self-adhering biomass, or single-cell suspension in a liquid medium.

In some embodiments, the cultivation infrastructure comprises adherent cells (i.e. those cells that adhere to a substrate). In some embodiments, the cultivation infrastructure comprises non-adherent cells (i.e. those cells that do not adhere to a substrate). In some embodiments, the cultivation infrastructure comprises both adherent and non-adherent cells.

Culture Density

Mass production of cells remains limited by several factors. One such factor is the culture density, described here as the ratio of the amount of biomass harvestable to the volume of the cultivation infrastructure. Increasing the culture density of the biomass may result in increased yields per unit of infrastructure volume, thereby decreasing the infrastructure volume required to cultivate the desired product and the overall efficiency of the cultivation process.

A primary factor limiting the culture density is the maximum thickness of the cultivated biomass attainable by cells in culture, for example for reasons of contact inhibition. In some embodiments, the culture density is increased by increasing the thickness of the cultivated cellular biomass. The thickness of a cellular biomass is determined by the cultivation infrastructure in which it is grown. Planes of a cultivation infrastructure can be described as apical and basal. The apical plane is the interface of the biomass surface with an extracellular medium. The basal plane is the interface of the biomass with a primary substrate.

Due to cell-to-cell contact inhibition, metazoan cells, when cultured on a substrate in a cultivation infrastructure, generally form a monolayer and stop proliferating once they reach confluence. In some embodiments, methods of increasing the culture density or the thickness of a metazoan cellular biomass comprise culturing a metazoan cellular biomass on a substrate in a cultivation infrastructure; and forming stratified layers of cells by inhibiting the HIPPO signaling pathway, for example, by activating YAP1 and/or TAZ in the cellular biomass or by inhibiting MOB1, LATS1 kinase, LATS2 kinase, WW45, MST1 kinase, and/or MST2 kinase. For example, see FIGS. 1 and 2. Inhibition of the HIPPO signaling pathway and formation of stratified layers of cells of the cellular biomass may suppress cell death (i.e. apoptosis, anoikis) and lead to detachment of the cellular biomass from the substrate thereby promoting anchorage-independent growth.

Metazoan cells, when cultured in suspension in a cultivation infrastructure, may adhere to the top, bottom or sidewalls of the cultivation infrastructure. Provided herein are methods that support anchorage-independent growth in suspension, for example, by inhibiting cell death and/or inducing proliferation of single cells of a metazoan cellular biomass suspended in a suspension culture to induce, support or maintain anchorage-independent growth. For example, see FIG. 3 that shows an exemplary embodiment where a cellular biomass is cultivated in a suspension culture, as a self-adherent aggregate. Alternately, in cellular biomass is cultivated in suspension culture, as a single-cell suspension. Accordingly, in some embodiments, methods of increasing the culture density or the thickness of a metazoan cellular biomass comprise culturing a metazoan cellular biomass in suspension in a cultivation infrastructure; and forming multiple layers of cells of the cellular biomass on top of each other by inhibiting the HIPPO signaling pathway, for example, by activating YAP1 and/or TAZ or by inhibiting MOB1, LATS1 kinase, LATS2 kinase, WW45, MST1 kinase, and/or MST2 kinase in the cellular biomass.

Figure 2:
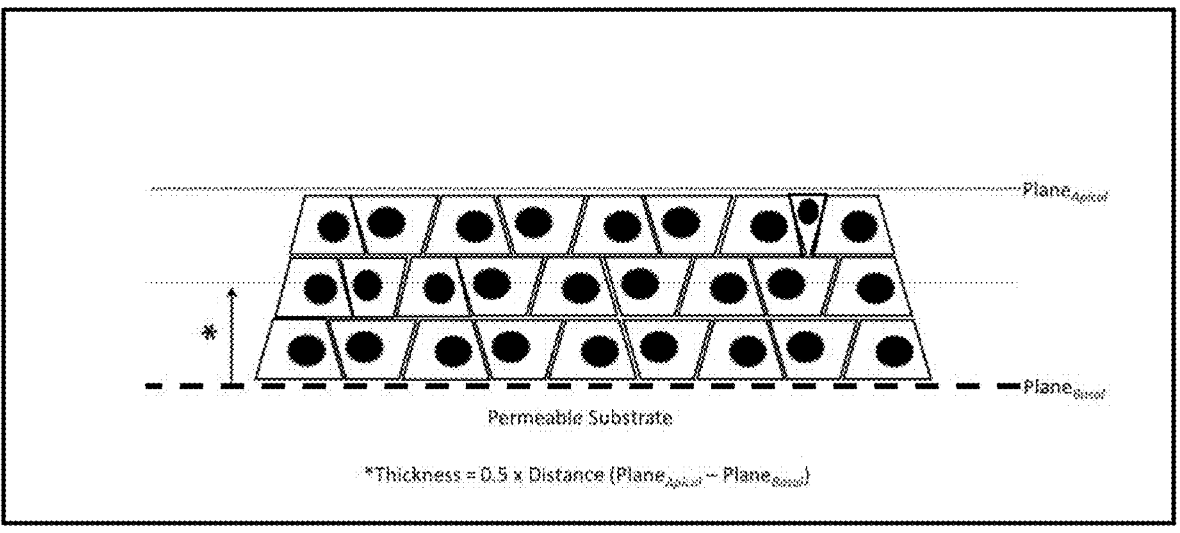
FIG. 2 depicts an exemplary embodiment where a cellular biomass is cultivated on a substrate permeable to physiological solutions.
Figure 3:
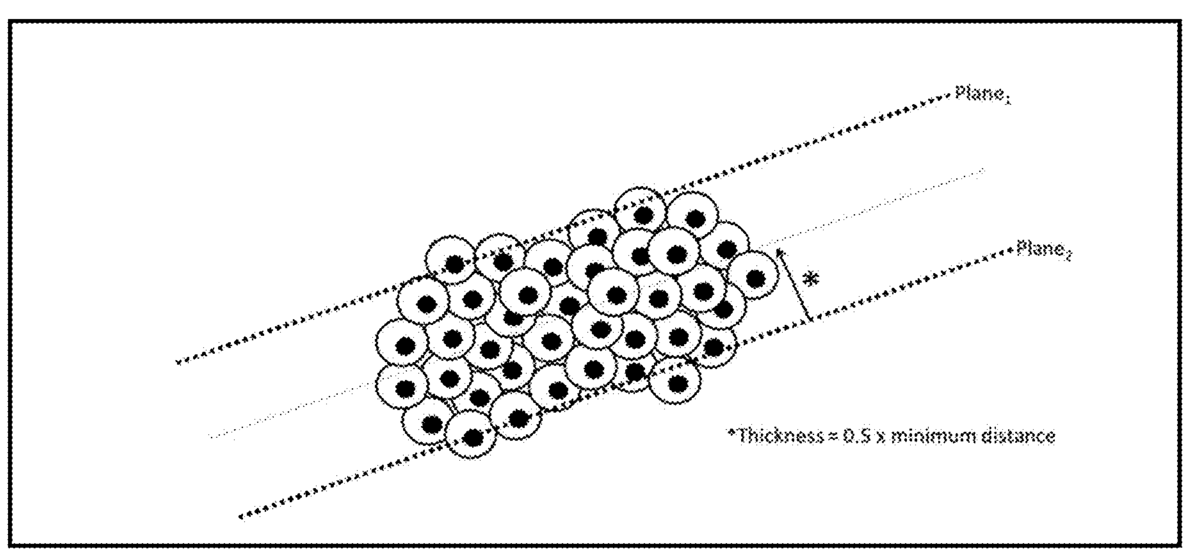
FIG. 3 depicts an exemplary embodiment where a cellular biomass is cultivated in a suspension culture, as a self-adherent aggregate.

In one embodiment, the methods described herein lead to the loss of contact inhibition of adherent cells. In various aspects, the methods can decrease contact inhibition by about 10%, 20%, 30%, 40%, 50%, 60%, 70%, 80%, 90%, or 100%, including values and ranges therebetween, compared to the methods where the HIPPO signaling is not inhibited.

Where a biomass is cultivated on a substrate impermeable to physiological solutions, the thickness of the cellular biomass is the distance between the basal and apical plane of the cultivated biomass (depicted in FIG. 1).

Where the biomass is cultivated on a permeable substrate, the thickness is a fraction (e.g. about half) of the distance between the basal and apical plane of the cultivated biomass (depicted in FIG. 2).

Where the biomass is cultivated in a suspension culture, as a self-adherent aggregate, the thickness is a fraction (e.g. about half) of the minimum distance between opposing apical planes (depicted in FIG. 3).

Accordingly, provided herein are compositions and methods to increase the culture density and thickness of a cellular biomass in a cultivation infrastructure. In some embodiments, increasing the culture density of the cellular biomass in the cultivation infrastructure results in an increased yield harvestable per unit volume of the cultivation infrastructure. For example, in some embodiments, increasing the culture density of the cellular biomass in the cultivation infrastructure results in an increased cell mass per unit volume of the cultivation infrastructure. In some embodiments, the method results in volumetric expansion of the biomass between the lower threshold, delimited by contact inhibition of cell growth at or near the basal plane, and the upper threshold, delimited by the maximal thickness attainable given the rate of diffusion of wastes and nutrients across the biomass. This volumetric expansion between the upper and lower threshold can be further promoted by the inclusion of a secondary substrate, either introduced, or autologous, to direct cellular growth between the substrates.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase in the cellular biomass as described in greater detail below), the culture density of the cellular biomass may reach about $10^5$ cells/mL, about $10^6$ cells/mL, about $10^7$ cells/mL, about $10^8$ cells/mL, about $10^9$ cells/mL, or about $10^{10}$ cells/mL (cells in the cellular biomass/mL of cultivation infrastructure), including values and ranges therebetween.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase in the cellular biomass as described in greater detail below), the culture density of the cellular biomass may reach about 1 g/L, 5 g/L, 10 g/L, 25 g/L, 50 g/L, 75 g/L, 100 g/L, 150 g/L, 200 g/L, 250 g/L, 300 g/L, 350 g/L, 400 g/L, 450 g/L, 500 g/L, 550 g/L, 600 g/L, 650 g/L, 700 g/L, 750 g/L, 800 g/L, 850 g/L, 900 g/L, or 1000 g/L (g of cellular biomass/L of cultivation infrastructure), including values and ranges therebetween. In some embodiments, the culture density of the cellular biomass may range from about 1 g/L to about 5 g/L, about 1 g/L to about 750 g/L, about 1 g/L to about 500 g/L, about 1 g/L to about 250 g/L, about 1 g/L to about 100 g/L, about 1 g/L to about 50 g/L, about 5 g/L to about 1000 g/L, about 5 g/L to about 750 g/L, about 5 g/L to about 500 g/L, about 5 g/L to about 250 g/L, about 5 g/L to about 100 g/L, about 5 g/L to about 50 g/L, about 25 g/L to about 1000 g/L, about 25 g/L to about 750 g/L, about 25 g/L to about 500 g/L, about 25 g/L to about 300 g/L, about 25 g/L to about 250 g/L, about 25 g/L to about 100 g/L, about 50 g/L to about 1000 g/L, about 50 g/L to about 750 g/L, about 50 g/L to about 500 g/L, about 50 g/L to about 300 g/L, about 50 g/L to about 250 g/L, about 100 g/L to 1000 g/L, about 100 g/L to about 750 g/L, about 100 g/L to about 500 g/L, about 200 g/L to about 1000 g/L, about 200 g/L to about 750 g/L, about 200 g/L to about 500 g/L, about 300 g/L to about 1000 g/L, about 300 g/L to about 800 g/L, about 400 g/L to about 1000 g/L, or about 500 g/L to about 1000 g/L including values and ranges therebetween.

As provided herein, the culture density of the biomass in the cultivation infrastructure is determined by calculating the cell number per unit volume of the cultivation infrastructure, by determining the biomass per unit volume of the cultivation infrastructure, by determining the biomass DNA content per unit volume of the cultivation infrastructure, by determining the biomass RNA content per unit volume of the cultivation infrastructure, by determining the biomass protein content per unit volume of the cultivation infrastructure, or by visual, electronic, metabolic, spectroscopic, or microscopic, measurement of the biomass density.

In some embodiments, the culture density of the biomass in the cultivation infrastructure is calculated as the ratio of the amount of biomass harvestable to the volume of the cultivation infrastructure. In some embodiments, the culture density of the biomass in the cultivation infrastructure is calculated as the ratio of the amount of biomass harvestable to the volume of the culture medium used within the cultivation infrastructure. In some embodiments, by inhibiting the HIPPO signaling pathway in the cellular biomass, the ratio of the amount of biomass harvestable to the volume of the cultivation infrastructure is increased about 2 to 30 times, 2 to 25 times, 2 to 20 times, 2 to 15 times, 2 to 10 times, 5 to 30 times, 5 to 25 times, 5 to 20 times, 5 to 15 times, 5 to 50 times, 10 to 50 times, 10 to 40 times, 10 to 30 times, 10 to 20 times, including values and ranges therebetween, compared to the ratio obtained when the HIPPO signaling pathway is not inhibited. In some embodiments, the ratio is increased by about 2, 3, 4, 5, 6, 7, 8, 9, 10, 12, 15, 20, 25, 30, 35, 40, 45, or about 50 times, including values and ranges therebetween, compared to the ratio obtained when the HIPPO signaling pathway is not inhibited.

In some embodiments, the culture density and/or thickness of a cellular biomass where HIPPO signaling is inhibited is about 1.025 fold, 1.05 fold, 1.10-fold, 1.15-fold, 1.20-fold, 1.25-fold, 1.30 fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where HIPPO signaling is not inhibited.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, the thickness of the cellular biomass may reach from about 5 μm to about 400 μm, about 5 μm to about 350 μm, about 5 μm to about 300 μm, about 5 μm to about 250 μm, about 5 μm to about 200 μm, about 5 μm to about 150 μm, about 5 μm to about 100 μm, about 10 μm to about 400 μm, about 10 μm to about 350 μm, about 10 μm to about 300 μm, about 10 μm to about 250 μm, about 10 μm to about 200 μm, about 10 μm to about 150 μm, about 10 μm to about 100 μm, about 20 μm to about 400 μm, about 20 μm to about 350 μm, about 20 μm to about 300 μm, about 20 μm to about 250 μm, about 20 μm to about 200 μm, about 20 μm to about 150 μm, about 20 μm to about 100 μm, about 50 μm to about 500 μm, about 50 μm to about 450 μm, about 50 μm to about 400 μm, about 50 μm to about 350 μm, about 50 μm to about 300 μm, about 50 μm to about 250 μm, about 100 μm to about 500 μm about 100 μm to about 400 μm, about 100 μm to about 300 μm, or about 100 μm to about 250 μm. including values and ranges therebetween.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, the thickness of the cellular biomass may reach from about 10 μm to about 2 mm, about 10 μm to about 1.5 mm, about 10 μm to about 1 mm, about 10 μm to about 500 μm, about 50 μm to about 2 mm, about 50 μm to about 1.5 mm, about 50 μm to about 1 mm, about 50 μm to about 500 μm, about 100 μm to about 2 mm, about 100 μm to about 1.5 mm, about 100 μm to about 1 mm, about 100 μm to about 500 μm, about 150 μm to about 2 mm, about 150 μm to about 1.5 mm, about 150 μm to about 1 mm, or about 150 μm to about 500 μm, including values and ranges therebetween.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, the thickness of the cellular biomass may reach from 100 μm to about 20 mm, about 100 μm to about 15 mm, about 100 μm to about 10 mm, about 100 μm to about 5 mm, about 1 mm to about 20 mm, about 1 mm to about 15 mm, about 1 mm to about 10 mm, about 5 mm to about 20 mm, or about 5 mm to about 15 mm, including values and ranges therebetween. For example, in some embodiments, by inhibiting the HIPPO signaling pathway in the cellular biomass, the thickness of the cellular biomass may reach about 100 μm, 250 μm, 500 μm, 1 mm, 1.5 mm, 2 mm, 2.5 mm, 3 mm, 3.5 mm, 4 mm, 4.5 mm, or 5 mm, including values and ranges therebetween. In some embodiments, by inhibiting the HIPPO signaling pathway in the cellular biomass, the thickness of the cellular biomass may reach about 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, 18 mm, 18.5 mm, 19 mm, 19.5 mm, or 20 mm, including values and ranges therebetween.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, there is an increased yield of cellular biomass harvestable per unit volume of the cultivation infrastructure. In some embodiments, the increase is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000% compared to when there is no inhibition of the HIPPO signaling pathway in the cellular biomass.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, there is an increased yield of cellular biomass harvestable per unit volume of the cultivation infrastructure. In some embodiments, the increase is at least about 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold compared to when there is no inhibition of the HIPPO signaling pathway in the cellular biomass.

In some embodiments, inhibition of the HIPPO signaling pathway in the cellular biomass increases the culture density and/or thickness of the cellular biomass by increasing the rate of proliferation of cells of the cellular biomass. In some embodiments, the increase in the rate of cell proliferation is at least at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, including values and ranges therebetween, compared to when there is no inhibition of the HIPPO signaling pathway in the cellular biomass. In some embodiments, the increase in the rate of cell proliferation is about 25-1000%, about 25-750%, about 25-500%, about 50-1000%, about 50-750%, about 50-500%, about 100-1000%, about 100-750%, or about 100-500%, including values and ranges therebetween, compared to when there is no induced inhibition of the HIPPO signaling pathway in the cellular biomass. In some embodiments, the cellular biomass is not adherent.

In some embodiments, inhibition of the HIPPO signaling pathway in the cellular biomass decreases cell death within the cellular biomass. In some embodiments, the decrease of cell death is at least at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, including values and ranges therebetween, compared to when there is no induced inhibition of the HIPPO signaling pathway in the cellular biomass. In some embodiments, decreased cell death within the cellular biomass is about 2.5-10%, about 2.5-75%, about 2.5-50%, about 5.0-100%, about 5.0-75%, about 5.0-50%, about 10-100%, about 10-75%, or about 10-50%, including values and ranges therebetween, compared to when there is no induced inhibition of the HIPPO signaling pathway in the cellular biomass. In some embodiments, the cellular biomass is not adherent.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase in the cellular biomass), there is an increase in density and thickness, with little or no contact inhibition of the proliferating cells in the biomass.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, there is an increase in density and thickness, with minimal impact on the rate of diffusion of wastes and nutrients across the biomass.

In some embodiments, methods for increasing the culture density of a metazoan cellular biomass in a cultivation infrastructure comprise: (a) culturing a metazoan cellular biomass in a cultivation infrastructure, and (b) inhibiting the HIPPO signaling pathway (e.g., by activating YAP1 and/or TAZ or homologs thereof, or by inhibiting MOB1, LATS1 kinase, LATS2 kinase, WW45, MST1 kinase, and/or MST2 kinase or homologs thereof) in the cellular biomass to provide a culture density of about $10^5$ cells/mL to about $10^{10}$ cells/mL in the cultivation infrastructure. In some embodiments, the step of inhibiting the HIPPO signaling pathway is carried out to provide a culture density of about 5 g/L to about 1000 g/L in the cultivation infrastructure. Ranges and values of culture densities that may be provided by the methods of the invention are described throughout this disclosure. Accordingly, in various embodiments, the step of inhibiting the HIPPO signaling pathway may be carried out to provide the ranges or values of culture densities described throughout this disclosure.

In some embodiments, methods for increasing the thickness of a metazoan cellular biomass in a cultivation infrastructure comprise: (a) culturing a metazoan cellular biomass in a cultivation infrastructure, and (b) inhibiting the HIPPO signaling pathway (e.g., by activating YAP1 and/or TAZ or homologs thereof, or by inhibiting MOB1, LATS1 kinase, LATS2 kinase, WW45, MST1 kinase, and/or MST2 kinase or homologs thereof) in the cellular biomass to provide a thickness of about 10 μm to about 2 mm to the cellular biomass in the cultivation infrastructure. Ranges and values of the thickness of cellular biomass that may be provided by the methods of the invention are described throughout this disclosure. Accordingly, in various embodiments, the step of inhibiting the HIPPO signaling pathway may be carried out to provide the ranges or values of thickness described throughout this disclosure.

Anchorage-Independent Growth

Provided herein are compositions and methods to promote/enhance anchorage-independent growth of a cellular biomass in a cultivation infrastructure. More specifically the methods promote/enhance the growth of cells that are typically anchorage-dependent in a suspension culture in an anchorage independent manner. These methods comprise inhibition of the HIPPO signaling pathway in the cellular biomass. FIG. 3 depicts the growth of a cellular biomass in an anchorage-independent context, in a suspension culture.

In some embodiments, methods to promote anchorage-independent growth of a cellular biomass in a cultivation infrastructure comprises: (a) culturing metazoan cells in a cultivation infrastructure; (b) antagonizing the HIPPO signaling pathway in the cells to increase the rate of cell proliferation (c) antagonizing the HIPPO signaling pathway to repress cell death. The rate of cell proliferation can be assessed, for example, by counting the number of cells in the S-phase. In some embodiments, an increase in the rate of cell proliferation and decrease in cell death promotes adherent cells to transition to a non-adherent form. In some embodiments, an increase in the rate of cell proliferation and decrease in cell death promotes transition of anchorage-independent growth cells in cells from anchorage-dependent growth.

In one embodiment, inhibition of the HIPPO signaling pathway promotes anchorage-independent growth by increasing the rate of cell proliferation. In some embodiments, increase in the rate of cell proliferation is at least 2.5%, at least 5%, 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, including values and ranges therebetween, compared to when there is no inhibition of the HIPPO signaling pathway in the cellular biomass. In some embodiments, the increase in the rate of cell proliferation is about 25-1000%, about 25-750%, about 25-500%, about 50-1000%, about 50-750%, about 50-500%, about 100-1000%, about 100-750%, or about 100-500%, including values and ranges therebetween, compared to when there is no inhibition of the HIPPO signaling pathway in the cellular biomass.

In one embodiment, the methods described herein promote anchorage-independent growth by decreasing cell-to-cell contact inhibition. In some embodiments, the decrease in contact inhibition provided by the present methods is about 10%, 20%, 30%, 40%, 50%, 60%, 70%, 80%, 90%, or 100%, including values and ranges therebetween, compared to the methods where the HIPPO signaling is not inhibited.

In one embodiment, the methods described herein promote anchorage-independent growth by decreasing cell death. In some embodiments, the decrease in contact inhibition provided by the present methods is about 2.5%, 5%, 10%, 20%, 30%, 40%, 50%, 60%, 70%, 80%, 90%, or 100%, including values and ranges therebetween, compared to the methods where the HIPPO signaling is not inhibited.

Methods

Provided herein are methods to increase the culture density in a cultivation infrastructure, to increase the thickness of a cellular biomass in a cultivation infrastructure, and/or to promote anchorage-independent growth of a cellular biomass. Also provided are methods of making edible or therapeutic cellular biomass comprising increasing the culture density or the thickness of a cellular biomass in a cultivation infrastructure.

In some embodiments, at least one step of the methods described herein can be carried out in the absence of serum. For example, by using serum-free media for culturing of the cells of a cellular biomass, for inhibiting the HIPPO signaling pathway, for differentiation of the cellular biomass, and/or for harvesting of the cellular biomass. In some embodiments, the entire method can be performed in serum-free conditions. In other embodiments, some steps are carried out in the absence of serum while some steps are carried out in the presence of serum. In some embodiments, provided herein are methods of increasing cell proliferation in the absence of serum.

In various embodiments, the methods of the present disclosure comprise inhibiting the HIPPO signaling pathway.

Inhibiting the HIPPO Signaling Pathway

In some embodiments, inhibiting the HIPPO signaling pathway comprises activating Yes-Associated Protein 1 (YAP1) or homologs thereof in the cellular biomass, activating Transcriptional Co-Activator with PDZ-binding motif (TAZ, WWTR1) or homologs thereof in the cellular biomass, or activating both YAP1 and TAZ or homologs thereof in the cellular biomass. In some embodiments, inhibiting the HIPPO signaling pathway comprises inhibiting a regulatory protein, Mps One Binder kinase activator 1 (MOB1) or homologs thereof, in the cellular biomass, inhibiting Large Tumor Suppressor kinase 1 (LATS1) or LATS2 kinase or homologs thereof in the cellular biomass, inhibiting MOB1 and either the LATS1 or LATS2 kinase or homologs thereof in the cellular biomass or inhibiting MOB1 and both LATS1 and LATS2 kinases or homologs thereof in the cellular biomass. In some embodiments, inhibiting the HIPPO signaling pathway comprises inhibiting a regulatory protein, WW45 or homologs thereof, in the cellular biomass, inhibiting Macrophage Stimulating 1 (MST1) kinase or MST2 kinase or homologs thereof in the cellular biomass, inhibiting WW45 and either the MST1 or MST2 kinase or homologs thereof in the cellular biomass or inhibiting WW45 and both MST1 and MST2 kinases or homologs thereof in the cellular biomass.

As contemplated herein, in some embodiments, the activation of YAP1 and TAZ or homologs thereof or the inhibition of MOB1, LATS1/2 kinases, WW45, and MST1/2 kinases or homologs thereof is at the gene level or the protein level. Accordingly, in the methods described herein, the YAP1, TAZ, MOB1, LATS1/2 kinases, WW45, and MST1/2 kinases or homologs thereof may be in the wild-type or mutant form.

In some embodiments, the HIPPO signaling pathway may be inhibited by adding a HIPPO signaling inhibitor to culture media. In some embodiments, HIPPO signaling inhibitors include animal serum, sphingosine-1-phosphate, thrombin, and lysophosphatidic acid. In some embodiments, HIPPO signaling may be inhibited by adding YAP1 and/or TAZ proteins (purified, synthetic, or recombinantly produced), recombinantly produced dominant negative mutants of MOB1, LATS1/2 kinases, WW45, and/or MST1/2 kinases, or combinations thereof.

Figure 14:
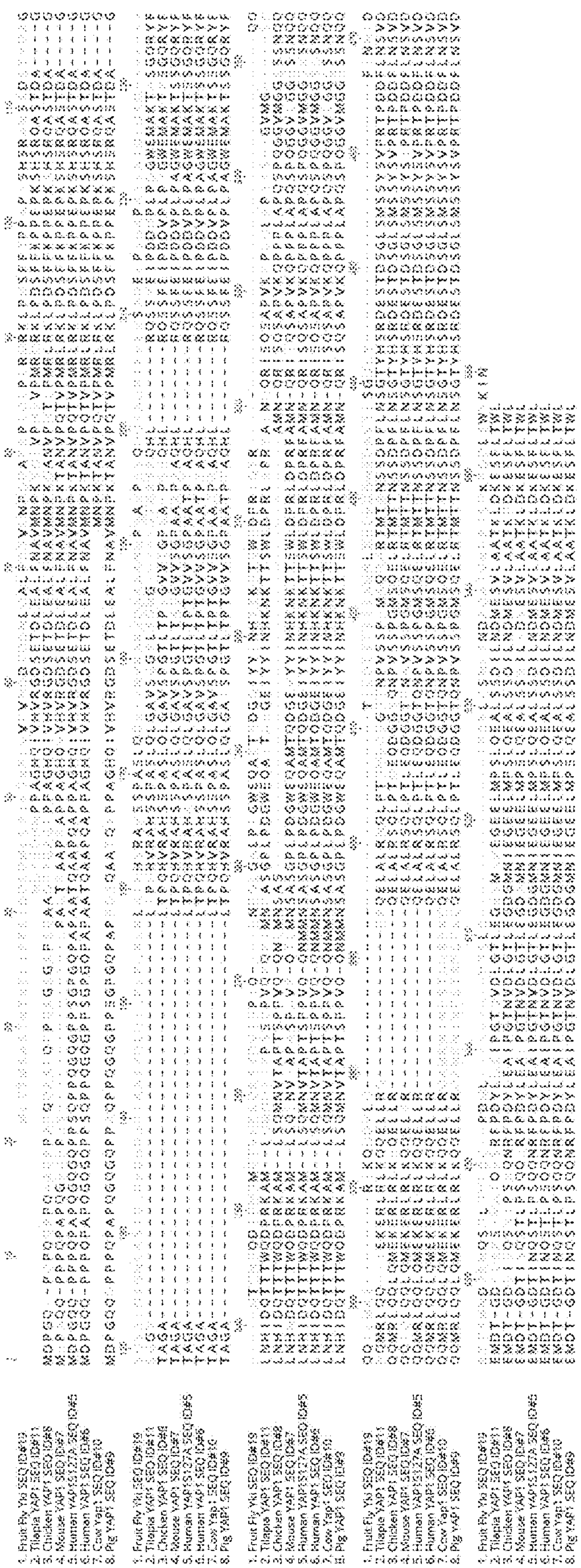
FIG. 14 shows amino acid residues that are conserved between YAP1 and its homologs from various species.
Figure 15:
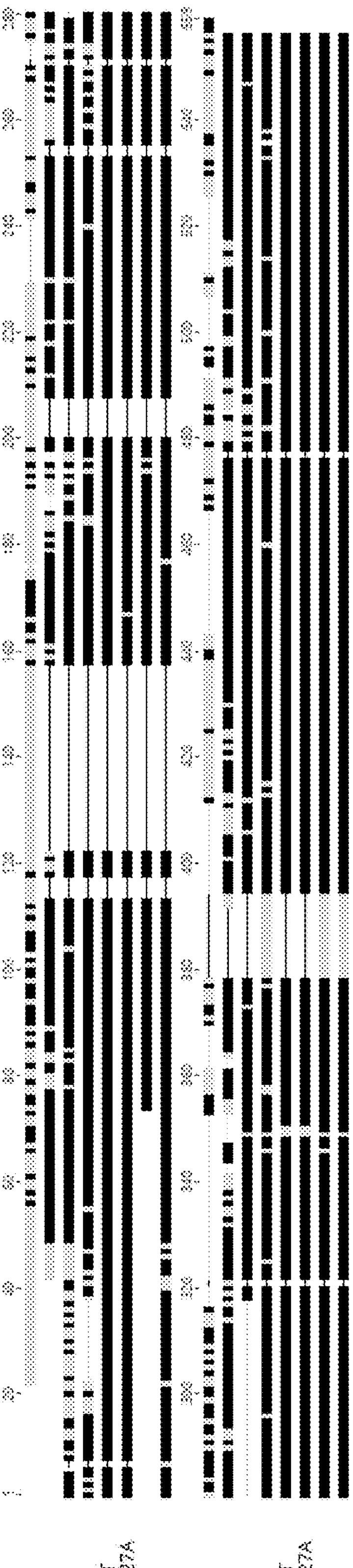
FIG. 15 shows the homology between YAP1 and its homologs from various species.
Figure 16:
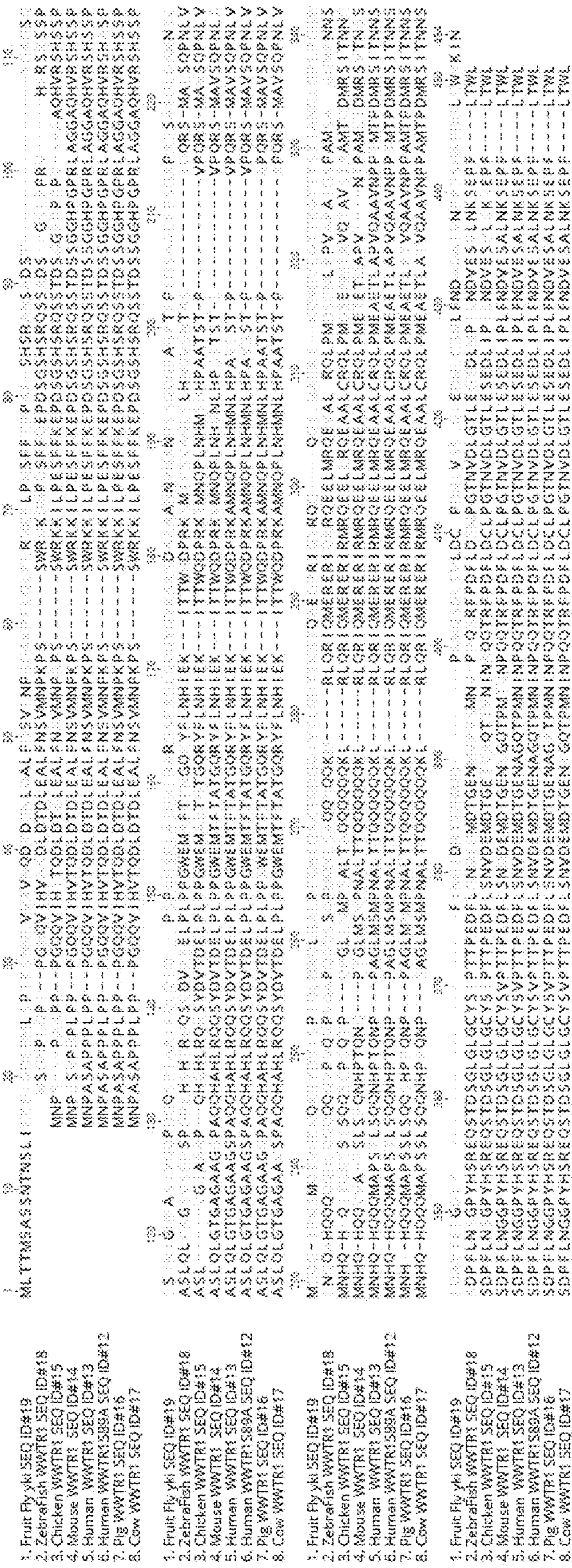
FIG. 16 shows amino acid residues that are conserved between WWTR1 and its homologs from various species.

In some embodiments, the HIPPO signaling may be inhibited by using or targeting homologs of YAP1, TAZ, MOB1, LATS1/2 kinases, WW45, and MST1/2 kinases. The term "homolog" as used herein encompasses orthologs (from different species) and paralogs (from the same species). In mammals, the YAP1 and TAZ proteins are expressed from the YAP1 and WWRT1 genes, respectively, and constitute paralogs of one another. Certain metazoan species, however, may not express proteins identified as YAP1 or TAZ, and instead express homologs of YAP1 and/or TAZ whose functions are conserved, in whole or in part, by YAP1 or TAZ. For instance, *Drosophila melanogaster* expresses a single homolog of YAP1 and WWTR1 genes, identified as the Yki gene, which encodes the transcriptional co-activator Yorkie protein. FIGS. 14 and 15 show conserved amino acid residues and protein domains of YAP1 and its homologs from various species. FIG. 16 shows conserved amino acid residues of WWTR1 and its homologs from various species. Although the homologs of YAP1 and/or TAZ are phylogenetically diverse, they show a high degree of conserved activity that is similar to YAP1 and TAZ. Therefore, many of these homolog proteins not identified as YAP1 or TAZ may be used to functionally substitute YAP1 or TAZ in the methods described herein. Accordingly, in some embodiments, methods disclosed herein may comprise activating one or more homologs of YAP1 and TAZ. Methods of activating YAP1 and/or TAZ are described in greater detail below. Similar methods can be used for activation of one or more homologs of YAP1 and TAZ.

Many metazoan species may not express MOB1, LATS1/2 kinases, WW45, and MST1/2 kinases; but instead express homologs of these proteins. For example, in *Drosophila melanogaster*, a single protein, Warts, is a homolog of the mammalian LATS1/2 proteins; a single protein, Mats, is a homolog of the mammalian MOB1 proteins; a single protein, Hippo, is a homolog for the mammalian MST1/2 proteins; and a single protein, Salvador, is a homolog of the mammalian WW45 protein. Accordingly, in certain embodiments, methods of the present disclosure may comprises inhibition of homologs of MOB1, LATS1/2 kinases, WW45, and MST1/2 kinases, such as Mats/Warts or Hippo/Salvador. For example, in embodiments, where the metazoan cellular biomass comprises cells with a genotype more closely akin to *Drosophila melanogaster*, the methods of increasing the culture density or the thickness of cellular biomass may comprise inhibiting Mats/Warts and/or Hippo/Salvador. Methods of inhibiting MOB1, LATS1/2 kinases, WW45, and MST1/2 kinases are described in greater detail below. Similar methods can be used for inhibiting one or more homologs of MOB1, LATS1/2 kinases, WW45, and MST1/2 kinases.

In some embodiments, inhibiting the HIPPO signaling pathway in the cellular biomass comprises inhibiting, at the gene or protein level, one or more non-canonical HIPPO signaling agonists such as aPKC, Tao1, Msn and/or PRP4k that are expressed, for example, in *Drosophila melanogaster*, or homologs thereof.

In embodiments, where the HIPPO signaling is inhibited by introducing into the cells of the cellular biomass an exogenous nucleic acid (e.g., a vector comprising a gene expressing constitutively active YAP1) or an exogenous protein (e.g. a wild-type or mutant YAP1 protein), the exogenous nucleic acid or the protein can be heterologous to the metazoan species or it can be species-matched. For example, the culture density and/or thickness of a cellular biomass comprising chicken skeletal muscle cells can be increased by introducing into the cells of the cellular biomass an exogenous nucleic acid that expresses constitutively active form of chicken YAP1 (species-matched) or human YAP1 (heterologous).

It is understood that the methods described throughout this disclosure for inhibiting the HIPPO signaling can be used alone or in combination. For example, methods of inhibiting the HIPPO signaling such as activating YAP1 and/or homologs thereof in the cellular biomass; activating TAZ and/or homologs thereof in the cellular biomass; activating both YAP1 and TAZ and/or homologs thereof in the cellular biomass; inhibiting MOB1, LATS1/2 kinases, WW45, and/or MST1/2 kinases and/or homologs thereof in the cellular biomass; inhibiting non-canonical HIPPO signaling agonists such as aPKC, Tao1, Msn and/or PRP4k and/or homologs thereof in the cellular biomass; contacting the cellular biomass with one or more of serum, lysophosphatidic acid, sphingosine-1-phosphate and/or thrombine, etc. can be used alone or in combinations.

Activating YAP1

In some embodiments, the methods of activating comprise increasing the amount of YAP1 in the cellular biomass by delivering a YAP1 protein directly, e.g. a purified protein, a synthetic protein, or a recombinantly expressed protein, to the cellular biomass (e.g. contacting the cultured cellular biomass with such a protein).

In some embodiments, the methods of activating comprise increasing the cellular expression of YAP1, by expressing a polynucleotide that encodes YAP1. In some embodiments, the polynucleotide is ectopically expressed from a construct that is introduced into the cells of the biomass, for example expressed from a plasmid, or other vector. In some embodiments, the construct is integrated into the cell's host genome, and the expression is driven in that manner (e.g. introduction mediated by CRISPR-based technology). In some embodiments, the expression of the polynucleotide involves injecting a naked DNA, delivering a DNA complexed with a liposome, using a viral vector (e.g. retrovirus, lentivirus, adenovirus, adeno-associated virus, herpes-simplex virus) to deliver an expression vector, and the like. In some embodiments, the expression is constitutive. In some embodiments, the expression is conditional, e.g. inducible, e.g. under the control of an inducible promoter, e.g. an inducible Tet construct.

In some embodiments, the YAP1 protein that is delivered or expressed comprises a mutation. In some embodiments, the YAP1 comprises a mutation in one or more motifs that allow for phosphorylation of YAP1 by the Large Tumor Suppressor Kinase 1 paralogs, LATS1 kinase and/or LATS2 kinase. In some embodiments the mutated YAP1 comprises a mutation at one or more of S5, S61, S109, S127, S163, S164, and S318 ("S" serine residue number corresponds to the human YAP1 protein). In some embodiments the mutation is an S to A (serine to alanine) mutation. In exemplary embodiments, the mutated YAP1 comprises one or more of S5A, S61A, S109A, S127A, S163A, S164A, and S318A mutations. It is noted that the residue positions recited above refer to the human YAP1 protein. It is understood that the corresponding serine residues in other organisms contributing to the motif for phosphorylation may differ.

In some embodiments, the methods of activating comprise increasing the transcriptional activation of the endogenous YAP1 gene in the cellular biomass. This can be accomplished, for example, by adding a purified, synthetic, or recombinantly produced transcriptional activator of the YAP1 gene to the cellular biomass. In one embodiment, the transcriptional activator of the YAP1 gene added to the culture medium could be a constitutively active form that would drive a continuous expression of the YAP1 gene. In another embodiment, transcriptional activation of the YAP1 gene can be accomplished using nucleic acid sequence-directed transcriptional activators. For example, clustered regularly interspaced short palindromic repeats (CRISPR) and the CRISPR associated protein 9 (Cas9) system can provide effective gene modification (activation and repression) through RNA-guided DNA targeting. The Cas9 protein can be altered to create an endonuclease-defective Cas9 (dCas9). In one embodiment, the dCas9 protein can be fused to a transactivation domain of a transcription factor or a transcriptional activator and the fusion protein can be used to drive transcriptional activation of the endogenous YAP1 gene.

In some embodiments, the methods of activating YAP1 comprise regulating one or more mechanical factors, including modulating substrate elasticity/rigidity, confinement, stretching, and shear stress, in the cellular biomass. Such methods may result in mechanotransduction of YAP1 signaling.

In some embodiments, the activating methods comprise agonizing YAP1, e.g. by contacting the cellular biomass with serum; or by inhibiting a Hippo signaling pathway, by contacting the cellular biomass with one or more of unfractionated animal serum, lysophosphatididic acid, sphingosine-1-phosphate and thrombin. In some embodiments, the activation of YAP1 can be downregulated, as needed by Hippo pathway inhibitors such as epinephrine and glucagon, which repress co-activation by YAP1.

In some embodiments, the culture density of a cellular biomass where YAP1 is activated is about 1.010-fold, 1.025-fold, 1.05 fold, 1.10 fold, 1.15-fold, 1.20 fold, 1.25-fold, 1.30-fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where YAP1 is not activated.

Activating TAZ

In some embodiments, the methods of activating comprise increasing the amount of TAZ in the cellular biomass by delivering a TAZ protein directly, e.g. a purified protein, a synthetic protein, or a recombinantly expressed protein to the cellular biomass (e.g. contacting the cultured cellular biomass with such a protein).

In some embodiments, the methods of activating comprise increasing the cellular expression of TAZ, by expressing a polynucleotide that encodes TAZ. In some embodiments, the polynucleotide is ectopically expressed from a construct that is introduced into the cells of the biomass, for example expressed from a plasmid, or other vector. In some embodiments, the construct is integrated into the cell's host genome, and the expression is expression is driven in that manner (e.g. introduction mediated by CRISPR-based technology). In some embodiments the expression of the polynucleotide involves injecting a naked DNA, delivering a DNA complexed with a liposome, using a viral vector (e.g. retrovirus, lentivirus, adenovirus, adeno-associated virus, herpes-simplex virus) to deliver an expression vector, and the like. In some embodiments, the expression is constitutive. In some embodiments, the expression is conditional, e.g. inducible, e.g. under the control of an inducible promoter, e.g. an inducible Tet construct.

In some embodiments, the TAZ protein that is delivered or expressed comprises a mutation. In some embodiments, the TAZ comprises a mutation in one or more motifs that allow for phosphorylation of TAZ by the Large Tumor Suppressor Kinase 1 paralogs, LATS1 kinase and/or LATS2 kinase. In some embodiments the mutated TAZ comprises a mutation at S89 ("S" serine residue number corresponds to the human TAZ protein). In some embodiments the mutation is an S to A (serine to alanine) mutation. In an exemplary embodiment, the mutated TAZ comprises a S89A mutation. It is noted that the residue positions recited above refer to the human TAZ protein. It is understood that the corresponding serine residues in other organisms contributing to the motif for phosphorylation may differ.

In some embodiments, the methods of activating comprise increasing the transcriptional activation of the endogenous WWTR1 gene that encodes the TAZ protein in the cellular biomass. This can be accomplished, for example, by adding a purified, synthetic, or recombinantly produced transcriptional activator of the WWTR1 gene to the cellular biomass. In one embodiment, the transcriptional activator of the WWTR1 gene added to the culture medium could be a constitutively active form that would drive a continuous expression of the WWTR1 gene. In another embodiment, transcriptional activation of the WWTR1 gene can be accomplished using nucleic acid sequence-directed transcriptional activators. For example, the endonuclease-defective dCas9 protein can be fused to a transactivation domain of a transcription factor or a transcriptional activator and the fusion protein can be used to drive transcriptional activation of the endogenous WWTR1 gene.

In some embodiments, the methods of activating TAZ comprise regulating one or more mechanical factors, including modulating substrate elasticity/rigidity, confinement, stretching, and shear stress, in the cellular biomass. Such methods may result in mechanotransduction of TAZ signaling.

In some embodiments, the activating methods comprise agonizing TAZ, e.g. by contacting the cellular biomass with serum; or by inhibiting a Hippo signaling pathway, by contacting the cellular biomass with one or more of unfractionated animal serum, lysophosphatididic acid, sphingosine-1-phosphate and thrombin. In some embodiments, the activation of TAZ can be downregulated, as needed by Hippo pathway inhibitors such as epinephrine and glucagon, which repress co-activation by TAZ.

In some embodiments, the culture density and/or thickness of a cellular biomass where TAZ is activated is about 1.010-fold, 1.025-fold, 1.05 fold, 1.10 fold, 1.15-fold, 1.20 fold, 1.25-fold, 1.30-fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where TAZ is not activated.

Activating YAP1 and TAZ

In some embodiments, the methods of activating comprise increasing the amount of both YAP1 and TAZ in the cellular biomass by delivering YAP1 and TAZ proteins directly, e.g. purified proteins, synthetic proteins, or recombinantly expressed proteins, or combinations thereof, to the cellular biomass.

In some embodiments, the methods of activating comprise increasing the cellular expression of YAP1 and TAZ, by expressing polynucleotides that encode YAP1 and TAZ. In some embodiments, the polynucleotides are ectopically expressed from constructs that are introduced into the cells of the biomass, for example expressed from a plasmid, or other vector. In some embodiments, the constructs are integrated into the cell's host genome, and the expression is driven in that manner (e.g. introduction mediated by CRISPR-based technology). In some embodiments the expression of the polynucleotides involve injecting a naked DNA, delivering a DNA complexed with a liposome, using a viral vector (e.g. retrovirus, lentivirus, adenovirus, adeno-associated virus, herpes-simplex virus) to deliver an expression vector, and the like, or combinations thereof. In some embodiments, the expression is constitutive. In some embodiments, the expression is conditional, e.g. inducible, e.g. under the control of an inducible promoter, e.g. an inducible Tet construct. In some embodiments, the expression of one of YAP1 or TAZ is constitutive, whereas the expression of the other of YAP1 or TAZ is inducible.

In some embodiments, the YAP1 and/or TAZ protein that is delivered or expressed comprises a mutation. In some embodiments, the YAP1 and/or TAZ comprise a mutation in one or more motifs that allow for phosphorylation of YAP1 by the Large Tumor Suppressor Kinase 1 paralogs, LATS1 kinase and/or LATS2 kinase. In some embodiments the mutated YAP1 comprises a mutation at one or more of S5, S61, S109, S127, S163, S164, and S318 ("S" serine residue number corresponds to the human YAP1 protein). In some embodiments the mutation is an S to A (serine to alanine) mutation. In exemplary embodiments, the mutated YAP1 comprises one or more of S5A, S61A, S109A, S127A, S163A, S164A, and S318A mutations. In some embodiments the mutated TAZ comprises a mutation at S89 ("S" serine residue number corresponds to the human TAZ protein). In some embodiments, the mutation is an S to A (serine to alanine) mutation. In an exemplary embodiment, the mutated TAZ comprises a S89A mutation. It is noted that the residue positions recited above refer to the human YAP1 an TAZ proteins. It is understood that the corresponding serine residues in other organisms contributing to the motif for phosphorylation may differ. In some embodiments, the TAZ is wild type, and the YAP1 is mutated. In some embodiments, the YAP1 is wild type and the TAZ is mutated. In some embodiments both the YAP1 and TAZ are mutated.

In some embodiments, the methods of activating comprise increasing the transcriptional activation of the endogenous YAP1 and WWTR1 genes in the cellular biomass. This can be accomplished, for example, by adding purified, synthetic, or recombinantly produced transcriptional activators of the YAP1 and WWTR1 genes to the cellular biomass. In one embodiment, the transcriptional activators of the YAP1 and WWTR1 genes added to the culture medium could be constitutively active and drive a continuous expression of the two genes. In another embodiment, transcriptional activation of the YAP1 and WWTR1 genes can be accomplished using nucleic acid sequence-directed transcriptional activators. For example, the endonuclease-defective dCas9 protein can be fused to a transactivation domain of a transcription factor or a transcriptional activator and the fusion protein can be used to drive transcriptional activation of the endogenous YAP1 and WWTR1 gene.

In some embodiments, the methods of activating YAP1 and TAZ comprise regulating one or more mechanical factors, including modulating substrate elasticity/rigidity, confinement, stretching, and shear stress, in the cellular biomass. Such methods may result in mechanotransduction of YAP1 and TAZ signaling.

In some embodiments, the activating methods comprise agonizing YAP1 and TAZ, e.g. by contacting the cellular biomass with serum; or by inhibiting a Hippo signaling pathway, by contacting the cellular biomass with one or more of unfractionated animal serum, lysophosphatididic acid, sphingosine-1-phosphate and thrombin. In some embodiments, the activation of YAP1 and TAZ can be downregulated, as needed by Hippo pathway inhibitors such as epinephrine and glucagon, which repress co-activation by YAP1 and TAZ.

In some embodiments the culture density and/or thickness of a cellular biomass where YAP1 and TAZ is activated is about 1.010-fold, 1.025-fold, 1.05 fold, 1.10 fold, 1.15-fold, 1.20 fold, 1.25-fold, 1.30-fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where YAP1 and TAZ are not activated.

Inhibiting MOB1 and/or LATS1/2 Kinases

In some embodiments, the methods of inhibiting comprise introducing INDEL (insertion or deletion) mutations into a gene encoding MOB1, gene encoding LATS1 kinase, and/or gene encoding LATS2 kinase into the cells of the cellular biomass. This can be accomplished using any gene based technologies, for example, using CRISPR-Cas (Clustered Regularly Interspersed Short Palindromic Repeats) based technology or TALEN based technology.

In some embodiments, the methods of inhibiting comprise introducing into the cells of the cellular biomass a vector expressing a polynucleotide that encodes a dominant negative mutant of MOB1, LATS1 kinase, and/or LATS2 kinase. In some embodiments, the polynucleotide is ectopically expressed from a construct that is introduced into the cells of the biomass, for example expressed from a plasmid, or other vector. In some embodiments, the construct is integrated into the cell's host genome, and the expression is driven in that manner (e.g. introduction mediated by CRISPR-based technology). In some embodiments, the expression of the polynucleotide involves injecting a naked DNA, delivering a DNA complexed with a liposome, using a viral vector (e.g. retrovirus, lentivirus, adenovirus, adeno-associated virus, herpes-simplex virus) to deliver an expression vector, and the like. In some embodiments, the expression is constitutive. In some embodiments, the expression is conditional, e.g. inducible, e.g. under the control of an inducible promoter, e.g. an inducible Tet construct.

In some embodiments, the methods of inhibiting comprise delivering dominant negative mutants of MOB1, LATS1 kinase, and/or LATS2 kinase directly, e.g. purified proteins, synthetic proteins, or recombinantly expressed proteins, or combinations thereof, to the cellular biomass.

In some embodiments, the methods of inhibiting comprise transcriptional repression of the endogenous genes encoding MOB1, LATS1 kinase, and/or LATS2 kinase in cells of the cellular biomass. This can be accomplished, for example, by using nucleic acid sequence-directed transcriptional repressors. For example, an endonuclease-defective Cas9, dCas9, can be combined with a guide RNA that targets the promoter region of the genes encoding MOB1, LATS1 kinase, and/or LATS2 kinase and reduces the transcriptional activation and concomitant gene expression.

In some embodiments, the methods of inhibiting comprise inhibiting Hippo signaling, by contacting the cellular biomass with one or more of unfractionated animal serum, lysophosphatididic acid, sphingosine-1-phosphate and thrombin.

In some embodiments the culture density and/or thickness of a cellular biomass where MOB1, LATS1 kinase, and/or LATS2 kinase are inhibited is about 1.010-fold, 1.025-fold, 1.05 fold, 1.10 fold, 1.15-fold, 1.20 fold, 1.25-fold, 1.30-fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where MOB1, LATS1 kinase, and/or LATS2 kinase are not inhibited.

Inhibiting WW45 and/or MST1/2 Kinases

In some embodiments, the methods of inhibiting comprise introducing INDEL (insertion or deletion) mutations into a gene encoding WW45, gene encoding MST1 kinase, and/or gene encoding MST2 kinase into the cells of the cellular biomass. This can be accomplished by using any gene based technologies, for example, using CRISPR-Cas (Clustered Regularly Interspersed Short Palindromic Repeats) based technology or TALEN based technology.

In some embodiments, the methods of inhibiting comprise introducing into the cellular biomass a vector expressing a polynucleotide that encodes a dominant negative mutant of WW45, MST1 kinase, and/or MST2 kinase. In some embodiments, the polynucleotide is ectopically expressed from a construct that is introduced into the cells of the biomass, for example expressed from a plasmid, or other vector. In some embodiments, the construct is integrated into the cell's host genome, and the expression is driven in that manner (e.g. introduction mediated by CRISPR-based technology). In some embodiments, the expression of the polynucleotide involves injecting a naked DNA, delivering a DNA complexed with a liposome, using a viral vector (e.g. retrovirus, lentivirus, adenovirus, adeno-associated virus, herpes-simplex virus) to deliver an expression vector, and the like. In some embodiments, the expression is constitutive. In some embodiments, the expression is conditional, e.g. inducible, e.g. under the control of an inducible promoter, e.g. an inducible Tet construct.

In some embodiments, the methods of inhibiting comprise delivering to the cells of the cellular biomass dominant negative mutants of WW45, MST1 kinase, and/or MST2 kinase directly, e.g. purified proteins, synthetic proteins, or recombinantly expressed proteins, or combinations thereof.

In some embodiments, the methods of inhibiting comprise transcriptional repression of the endogenous genes encoding WW45, MST1 kinase, and/or MST2 kinase in the cells of the biomass. This can be accomplished, for example, by using nucleic acid sequence-directed transcriptional repressors. For example, an endonuclease-defective Cas9, dCas9, can be combined with a guide RNA that targets the promoter region of the genes encoding WW45, MST1 kinase, and/or MST2 kinase and reduces the transcriptional activation and concomitant gene expression.

In some embodiments, the methods of inhibiting comprise inhibiting Hippo signaling, by contacting the cellular biomass with one or more of unfractionated animal serum, lysophosphatididic acid, sphingosine-1-phosphate and thrombin.

In some embodiments, the culture density and/or thickness of a cellular biomass where WW45, MST1 kinase, and/or MST2 kinase are inhibited is about 1.010-fold, 1.025-fold, 1.05 fold, 1.10 fold, 1.15-fold, 1.20 fold, 1.25-fold, 1.30-fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where WW45, MST1 kinase, and/or MST2 kinase are not inhibited.

Serum Free Conditions

Unfractionated animal serum (UAS), for e.g., fetal bovine serum (FBS), is commonly used as a mitogenic supplement for cell cultures. However, there are certain drawbacks and/or concerns associated with the use of serum such as high cost, batch-to-batch variations, its derivation from an animal source and the like. Accordingly, in one embodiment, provided herein are compositions and methods for increasing cell proliferation, cell viability, and reducing cell death without adding serum to culture medium. In some embodiments, provided are compositions and methods for increasing the culture density and/or thickness of a cellular biomass and for promoting anchorage-independent growth comprising inhibiting the HIPPO signaling pathway without added serum.

The term "serum" as used herein refers to the liquid fraction of whole blood that is collected after the blood is allowed to clot. The clot can be removed by for e.g., centrifugation, and the resulting supernatant is designated serum.

Figure 4:
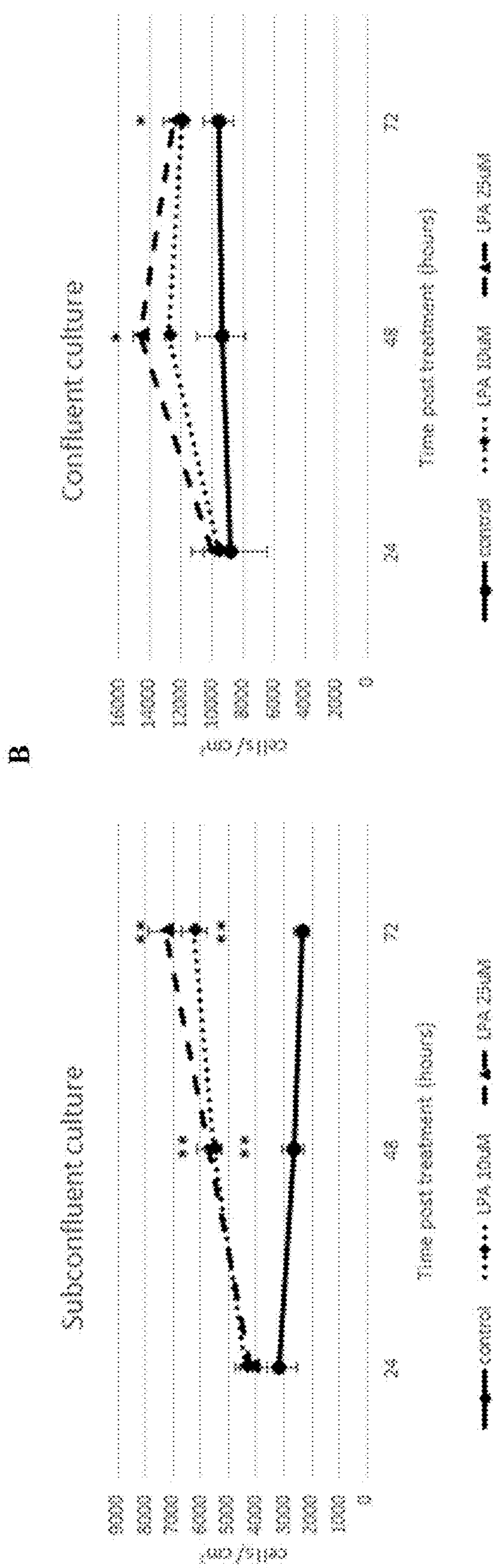
FIG. 4 shows the effect of lysophosphatidic acid on proliferation of primary bovine myoblasts in subconfluent (A) and confluent (B) cultures.

The inventors have found that it is possible to increase cell proliferation, cell viability, reduce cell death, and increase the culture density and/or thickness of a cellular biomass without adding serum to the culture medium (FIG. 4). For example, compositions and methods such as ectopic expression of YAP1 and/or TAZ; addition of YAP1 and/or TAZ proteins to the culture medium; activation of the endogenous YAP1 and/or TAZ genes using, for example, nucleic acid sequence-directed transcriptional activators; addition of HIPPO inhibitors such as lysophosphatidic acid, sphingosine-1-phosphate, and thrombin; and/or ectopic expression of dominant negative mutants of MOB1, LATS1 kinase, LATS2 kinase, WW45, MST1 kinase, and/or MST2 kinase can induce cell proliferation and increase the culture density and/or thickness of a cellular biomass without addition of serum.

Post Expansion Treatment of Cellular Biomass

Methods for increasing the culture density and thickness of cellular biomass and methods for anchorage-independent cell growth described above provide an expanded cellular biomass. Once the desired level of expansion (e.g. a specific range or value of culture density and/or thickness) of the cellular biomass is achieved, inhibition of the HIPPO signaling pathway can be partially or fully terminated and the expanded biomass may be differentiated and harvested.

In some embodiments, inhibition of the HIPPO signaling pathway can be partially or fully terminated by partial or complete removal of the HIPPO inhibitors. For example, in some embodiments, inhibition of the HIPPO signaling pathway can be partially or fully terminated by partial or complete removal of externally added HIPPO inhibitors such as serum, lysophosphatidic acid, YAP1 and TAZ proteins, dominant negative mutants of MOB1, LATS1/2 kinases, WW45, and/or MST1/2 kinases, and the like. In embodiments where the HIPPO signaling is inhibited by expression of YAP1 and/or TAZ proteins through a vector or expression of dominant negative mutants of MOB1, LATS1/2 kinases, WW45, and/or MST1/2 kinases through a vector, inhibition can be partially or fully terminated by activating a silencing switch included in the vector. For example, a silencing switch can be a transcriptional repressor that is included in the vector, which upon activation can repress the transcription of the desired gene.

After partial or complete termination of inhibition of HIPPO signaling, the expanded cellular biomass may be differentiated. In some embodiments, cells of the expanded biomass can be differentiated into a phenotype of interest by contacting the cells with a differentiation agent. For example, if the phenotype of interest for the expanded cellular biomass is skeletal muscle and the cellular biomass comprises cells of a non-muscle lineage (e.g., non-myogenic stem cells or fibroblasts), the expanded cellular biomass can be contacted with a differentiation agent that would induce the skeletal muscle phenotype into the cells of the biomass. Exemplary differentiation agents that may induce skeletal muscle phenotype include myogenic transcription factors such as MYOD1, MYOG, MYF5, MYF6, PAX3, PAX7, paralogs, orthologs, and genetic variants thereof. A PCT publication, WO/2015/066377, discloses exemplary methods for differentiating cells into a skeletal muscle phenotype and is incorporated by reference herein in its entirety. Accordingly, in some embodiments, the expanded cellular biomass may be differentiated into the skeletal muscle phenotype using the methods described in WO/2015/066377.

In some embodiments, cells of the expanded biomass can be differentiated into a phenotype of interest without a differentiation agent. For example, if the phenotype of interest for the expanded biomass is a skeletal muscle and the cellular biomass comprises cells of the skeletal muscle lineage, then these cells may differentiate into the skeletal muscle phenotype on their own without a need for an external differentiation agent. In these embodiments, a partial or complete removal of the antagonism of the HIPPO signaling pathway may be sufficient to induce differentiation of cells of to the skeletal muscle lineage and into the skeletal muscle phenotype. However, in some embodiments, an external differentiation agent such as one or more myogenic transcription factors can be used to differentiate cells of the skeletal muscle lineage into the skeletal muscle phenotype.

The expanded and/or differentiated cellular biomass can be processed as a raw, uncooked food product (cultured meat) or as a cooked food product or as a cooked/uncooked food ingredient. In some embodiments, processing comprises withdrawal of the culture medium that supports the viability, survival, growth or expansion (e.g., increase in the culture density and/or thickness of the biomass, anchorage-independent growth) and differentiation of the cellular biomass. Withdrawal may comprise physical removal of the culture medium or altering the composition of the culture medium, for example, by addition of components that would reduce or prevent further expansion and/or differentiation of the biomass or by depletion of components that support expansion and/or differentiation of the biomass.

In some embodiments, processing comprises exposing the biomass to sub-physiological temperatures that would not support the expansion and/or differentiation of the biomass. Sub-physiological temperatures include a temperature of about 15° C. (about 59° F.) or lower, about 10° C. (about 50° F.) or lower, about 0° C. to about 15° C. (about 32° F. to about 59° F.), about 0° C. to −15° C. (about 32° F. to about 5° F.), about −15° C. to about 15° C. (about 5° F. to about 59° F.), about 0° C. to −213° C. (about 32° F. to about −350° F.), about −30° C. to about −100° C. (about −22° F. to about −148° F.), about −50° C. to about −90° C. (about −58° F. to about −130° F.), or about −170° C. to about −190° C. (about −274° F. to about −310° F.). For example, in one embodiment, the expanded and/or differentiated biomass can be cooled to a temperature of about 2° C. to about 8° C. (about 35° F. to about 46.5° F.). In another embodiment, the expanded and/or differentiated biomass can be frozen, for example, by cooling to a temperature of about 32° F. or lower, e.g. about 32° F. to about 0° F., about 32° F. to about −10° F., about 32° F. to about −20° F., about 32° F. to about −30° F., about 32° F. to about −40° F., about 32° F. to about −50° F., about 32° F. to about −60° F., about 32° F. to about −70° F., about 32° F. to about −80° F., and the like. In some embodiments, the expanded and/or differentiated biomass can be exposed to sub-physiological temperatures as low as about −300° F. to about −350° F., such as the liquid nitrogen temperature of about −321° F.

In some embodiments, processing comprises exposing the biomass to superphysological temperatures that would not support the viability, survival, expansion and/or differentiation of the biomass. In one embodiment, exposing the biomass to superphysiological temperatures comprises fully or partially cooking the biomass, for example, by heating the biomass to a temperature of about 100° F. to about 600° F., about 100° F. to about 550° F., about 100° F. to about 500° F., about 100° F. to about 450° F., about 100° F. to about 400° F., about 100° F. to about 350° F., about 100° F. to about 300° F., about 100° F. to about 250° F., about 100° F. to about 200° F. or about 100° F. to about 150° F.

In some embodiments, provided herein are methods of producing edible cellular biomass (also referred to herein as "cultured meat") or therapeutic cellular biomass comprising, (a) culturing a metazoan cellular biomass in a cultivation infrastructure; (b) inhibiting the HIPPO signaling pathway in the cellular biomass, for example, by activating YAP1 and/or TAZ or by inhibiting MOB1, LATS1 kinase, LATS2 kinase, WW45, MST1 kinase, and/or MST2 kinase in the cellular biomass, to increase the culture density or the thickness of the cellular biomass; (c) optionally differentiating the cellular biomass into a phenotype of interest (e.g. skeletal muscle); (d) harvesting the cellular biomass to provide an edible or therapeutic cellular biomass.

In some embodiments, methods of producing edible cellular biomass or therapeutic cellular biomass comprise: (a) culturing a metazoan cellular biomass in a cultivation infrastructure; (b) inhibiting the HIPPO signaling pathway in the cellular biomass to provide a culture density of about $10^5$ cell/mL to about $10^{10}$ cells/mL or about 1 g/L to about 1000 g/L (or other values and ranges of the culture density described throughout this disclosure) in the cultivation infrastructure; (c) optionally differentiating the cellular biomass into a phenotype of interest (e.g. skeletal muscle); (d) harvesting and processing the cellular biomass to provide an edible or therapeutic cellular biomass.

In some embodiments, methods of producing edible cellular biomass or therapeutic cellular biomass comprise: (a) culturing a metazoan cellular biomass in a cultivation infrastructure; (b) inhibiting the HIPPO signaling pathway in the cellular biomass to provide a thickness of the cellular biomass of about 10 μm to about 2 mm (or other values and ranges of the thickness of the cellular biomass described throughout this disclosure) in the cultivation infrastructure; (c) optionally differentiating the cellular biomass into a phenotype of interest (e.g. skeletal muscle); (d) harvesting and processing the cellular biomass to provide an edible or therapeutic cellular biomass; (e) improve cell cell proliferation without added serum; (f) improve anchorage-independent cell proliferation.

Kits and Articles of Manufacture

The present application also provides kits for increasing the culture density in a cultivation infrastructure, for increasing the thickness of a cellular biomass in a cultivation infrastructure, and/or for promoting/increasing anchorage-independent growth of a cellular biomass in a cultivation infrastructure. For example, the kits may comprise the cells of interest, a cultivation infrastructure, and the HIPPO signaling pathway inhibitors such as YAP1 or TAZ vectors or protein; compositions for enhancing the activation of endogenous YAP1 and/or TAZ gene; compositions for the inhibition of MOB1, LATS1 kinase, LATS2 kinase, WW45, MST1 kinase, and/or MST2 kinase; vectors expressing dominant negative mutants of MOB1, LATS1 kinase, LATS2 kinase, WW45, MST1 kinase and/or MST2 kinase; and the like.

The present application also provides articles of manufacture comprising any one of the compositions or kits described herein.

It is to be understood that the terminology employed herein is used for the purpose of describing particular embodiments only and is not intended to be limiting since the scope of the present invention will be limited only by the appended claims and equivalents thereof. The following examples are for illustrative purposes. These are intended to show certain aspects and embodiments of the present invention but are not intended to limit the invention in any manner.

EXAMPLES

Example 1: Increasing the Thickness of Biomass Cultivated on a Substrate

One protocol for increasing the thickness of a biomass cultivated on a substrate comprises 7 steps: (1) transfect an anchorage-dependent, bovine myoblasts with a construct expressing YAP1 or TAZ under the control of a doxycycline-inducible eukaryotic promoter and containing an antibiotic-resistance gene; (2) select and enrich the transfected cells with a dosage of antibiotic lethal to the non-transfected cells; (3) passage the cells to a cultivation substrate supporting cell adhesion, and cultivating the cells to super-confluence in a proliferation medium, and for four additional days after the cells become super confluent, with daily culture media changes; in the presence of doxycycline; (4) aspirate the liquid proliferation medium from the cell biomass; (5) add liquid differentiation medium to the cell biomass, omitting doxycycline and differentiate the biomass into skeletal muscle over the course of four days, with daily media changes; (6) mechanically dissociate the cells from the substrate, and measure the weight of the bovine skeletal muscle biomass; and (7) prepare bovine skeletal muscle biomass as a food product by rinsing in an isotonic buffer and frying in an oiled pan until evenly brown. The expected yield limit of the cells population expressing the ectopic YAP1 or TAZ is expected to be at least 4-fold greater than the wild-type cells, due to the ability of the cells overexpressing the YAP1 or TAZ to bypass contact inhibition of cellular proliferation.

Example 2: Adapting Anchorage-Dependent Cells for Cultivation in Suspension

Anchorage-dependent cells can be adapted for cultivation in suspension, and can include at least the following steps: (1) transfect an anchorage-dependent, chicken myoblasts with a construct expressing YAP1 or TAZ under the control of a doxycycline-inducible eukaryotic promoter and containing an antibiotic-resistance gene; (2) select and enrich the transfected cells with a dosage of antibiotic lethal to the non-transfected cells; (3) passage the cells in a single-cell suspension to a shaker flask in proliferation medium supplemented with doxycycline, and shake flask in a slow, orbital motion sufficient to prevent the cells from sedimentation within the flask and keep cells in suspension; (4) clonally isolate proliferating cells from the suspension culture and passage to another suspension culture, as described in step no. 3 for scaling the cultivation of biomass, or into an anchorage-dependent culture, as described in Example 1, for cultivation of skeletal muscle biomass to be formulated as food.

Example 3: Isolation of Primary Cells from a Metazoan Source

Protocol #1: Prior to isolation of cells, a 150 $cm^2$ flask (T-150 flask) was prepared for cell attachment by dispersal of a 10 mL of a peptide solution (e.g. 0.1% gelatin) into the flask and incubating the flask for at least 1 hour at 37° C. The aqueous peptide solution was aspirated from the T-150 flask and the flask was rinsed with phosphate-buffered saline. 25 mL of growth medium was formulated to support proliferation of the cell type isolated. For example, a growth medium comprising Dulbecco's Modified Eagle Medium+10% bovine serum, was added to the flask and the flask was incubated and equilibrated under standard culture conditions, such as about 37° C. in 5% atmospheric $CO_2$.

Under aseptic conditions, a bovine skeletal muscle tissue was excised with dissection instruments. Viable metazoan tissues were harvested and minced into approximately 2 mm×2 mm sections. 150 mg tissue sections were weighed and then transferred to a sterile 50 mL centrifuge tube containing 8 mL of enzymatic cell dissociation solution (e.g. 0.17% trypsin and 0.085% collagenase in Hank's Balanced Salt Solution, pH 7.4). The centrifuge tube was closed tightly and incubated on ice. Following overnight incubation on ice, the tube was incubated at 37° C. for 15 minutes. The enzymatic tissue digest was triturated with a sterile 5 mL serological pipet for 1 minute. Cell suspension was passed through a sterile 70 μm strainer into a sterile 50 mL centrifuge tube. 20 mL of cold Dulbecco's Modified Eagle Medium was added to the strainer. The strainer was discarded, and the tube capped. The tube was centrifuged at 300×g for 5 minutes. The supernatant was aspirated, and the cell pellet was resuspended using the growth medium equilibrated in the 150 $cm^2$ flask. The cell suspension was transferred to the 150 $cm^2$ flask and the flask was returned to incubator for incubation under standard culture conditions.

The cells were checked daily for growth and contamination. The culture medium was changed every two to three days. After the cell cultures reached a confluence of 70% to 90%, the cells were dissociated and either cryopreserved or passaged using standard cell culture technique.

Protocol #2: Prior to isolation of cells, a T-150 flask was prepared as described in Protocol #1. In this protocol, a commercially available tissue dissociation instrument (e.g., from Miltenyi Biotech, Inc.) was used to dissociate tissues in conjunction with a commercially available skeletal muscle dissociation kit (e.g. from Miltenyi Biotech, Inc.). Skeletal muscle dissociation kit enzymes were mixed with Dulbecco's Modified Eagle Medium according to the manufacturer's instructions. ~5 mL of the enzymatic mixture was transferred into a gentleMACS C tube (Miltenyi Biotech, Inc.) according to the manufacturer's instructions.

Under aseptic conditions, a metazoan tissue of interest (e.g. a skeletal muscle tissue) was excised with dissection instruments. Viable tissues were minced into 2-4 mm pieces. Approximately one gram of the minced tissue was added to the gentleMACS C tube containing the enzymatic mixture. The gentleMACS C tube was closed tightly, loaded onto the tissue dissociation instrument, and an appropriate program cycle on the instrument was run according to the manufacturer's instructions. Once the program cycle ended, the gentleMACS C tube was unloaded and centrifuged at 300×g for 5 minutes to sediment isolated cells to the tube bottom. The cell isolate was resuspended in Dulbecco's Modified Eagle Medium and the cell suspension was applied to a 70 μM cell strainer placed on a 50 mL centrifuge tube. The cell strainer was washed with 20 mL of cold Dulbecco's Modified Eagle Medium and the cell strainer was discarded. The cell suspension was centrifuged at 300×g for 20 minutes, and the supernatant was aspirated completely. The cell suspension was resuspended using equilibrated cell growth medium from the T-150 flask and the flask was returned to the incubator for incubation under physiological conditions.

The isolated cells were checked daily for growth and contamination. The culture medium was changed every two to three days. After the cultures reached a confluence of 70% to 90%, the cells were dissociated and either cryopreserved or passaged using standard cell culture technique.

Example 4: Inhibition of the HIPPO Signaling Pathway Using Lysophosphatidic Acid (LPA) Increases the Culture Density/Thickness of Cellular Biomass Bovine myoblasts were isolated from a bovine skeletal muscle tissue using the protocol described above. Isolated myoblasts were plated at a culture density of 2000 (subconfluent) or 10,000 (confluent) cells per well in a 96 well plate in triplicate wells. The cells were allowed to adhere for 24 hours, at which time LPA was added at a concentration of 0, 10 or 25 μM in the medium. Cells were subsequently harvested and counted by bright field cell imaging (Cytation 5 live cell imaging, analyzed with Lionheart software). FIG. 4A shows that the cells in the subconfluent culture increased by 309% and the cells in the confluent culture (FIG. 4B) increased by 130%. Data shown are mean+/−SD. Significance was determined by the Student's T test.

Figure 5:
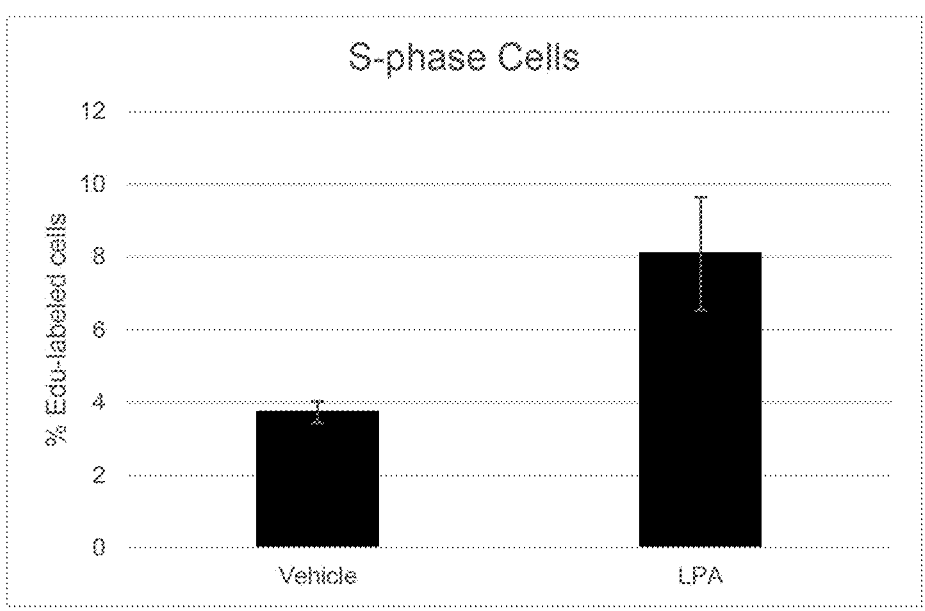
FIG. 5 shows that the treatment of primary bovine myoblasts with lysophosphatidic acid induces cell proliferation.
Figure 6:
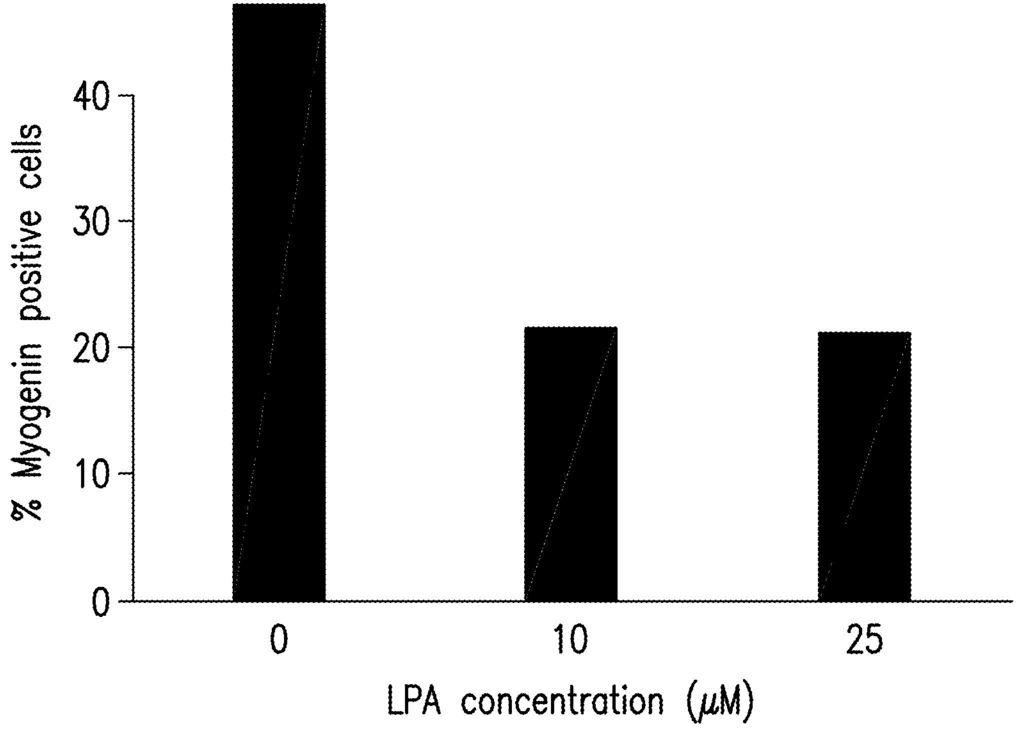
FIG. 6 shows that the treatment of primary bovine myoblasts with lysophosphatidic acid decreases differentiation of myoblasts to mature muscle cells.

In another experiment, bovine myoblasts were plated at a culture density of 10,000 cells per well in a 96 well plate in triplicate wells. The cells were allowed to adhere for 24 hours, when 10 μM LPA was added in the medium. Cells were subsequently harvested. After 24 hours, the proliferation rate was measured by EdU incorporation using a commercially available nucleoside pulse labeling kit such as the Click-iT-EdU kit (ThermoFisher). Briefly, cells were treated with 3 μM EdU, incubated at room temperature for 6 hours and detected according to the manufacturer's instructions, Cells were labeled with Alexa Fluor® 647 azide and analyzed using Fluorescence-Activated Cell Sorting (FACS) using 633 nm excitation and a 660/20 nm emission filter. FIG. 5 shows that the LPA treated cells had increased percentage (216% increase) of cells in the S-phase, which is indicative of increased proliferation, compared to vehicle-treated (culture medium alone without LPA) cells.

Example 5: Treatment of Cells with LPA Decreases Differentiation of the Cells

Isolated bovine myoblasts were plated in a culture medium without adding serum at a culture density of 10,000 cells per well in a 96 well plate in triplicate wells. The cells were allowed to adhere for 24 hours, when LPA was added at a concentration of 0, 10 or 25 μM in serum-free medium. LPA was added daily until harvesting. Myogenin was used as a marker of differentiation to mature muscle cells. To determine the degree of differentiation to mature muscle cells, cultures were fixed in 4% paraformaldehyde for 10 min and then washed with PBS. Cells were incubated with PBS/0.2% BSA/0.1% Triton-X100 for 20 min followed by incubation with an anti-myogenin antibody (Abcam, mouse, 1/150) for 1 h at room temperature. After 3 washes with PBS/0.2% BSA, cells were incubated with secondary antibodies (goat anti-rabbit Alexa488, 1/800; goat anti-mouse Alexa555, 1/800, Invitrogen) for 30 min at room temperature. Nucleus was stained with DAPI. LPA treated cells show reduced expression of myogenin.

Example 6: Generation of Plasmids Expressing YAP1-RFP, TAZ-GFP and Control Vectors Reporter vectors containing GFP and RFP reporter sequences, namely, pDd669-AD+RFP and pD663-ARc+GFP were obtained from ATUM Bio and used as control vectors. Human YAP1 polynucleotide sequence containing a constitutively active mutation S127A (SEQ ID NO: 1) was assembled into pD663-ARc vector, and human TAZ polynucleotide sequence containing a constitutively active mutation S89A (SEQ ID NO: 3) was assembled into pD669-AD for enforced expression of these genes. Vectors were introduced into cultured cells using Lipofectamine reagent (ThermoFisher) according to manufacturer's instructions, and selected using G418 (Sigma, pDd669 vectors) or puromycin (Sigma, pD663 vectors) for 14 days.

Figure 7:
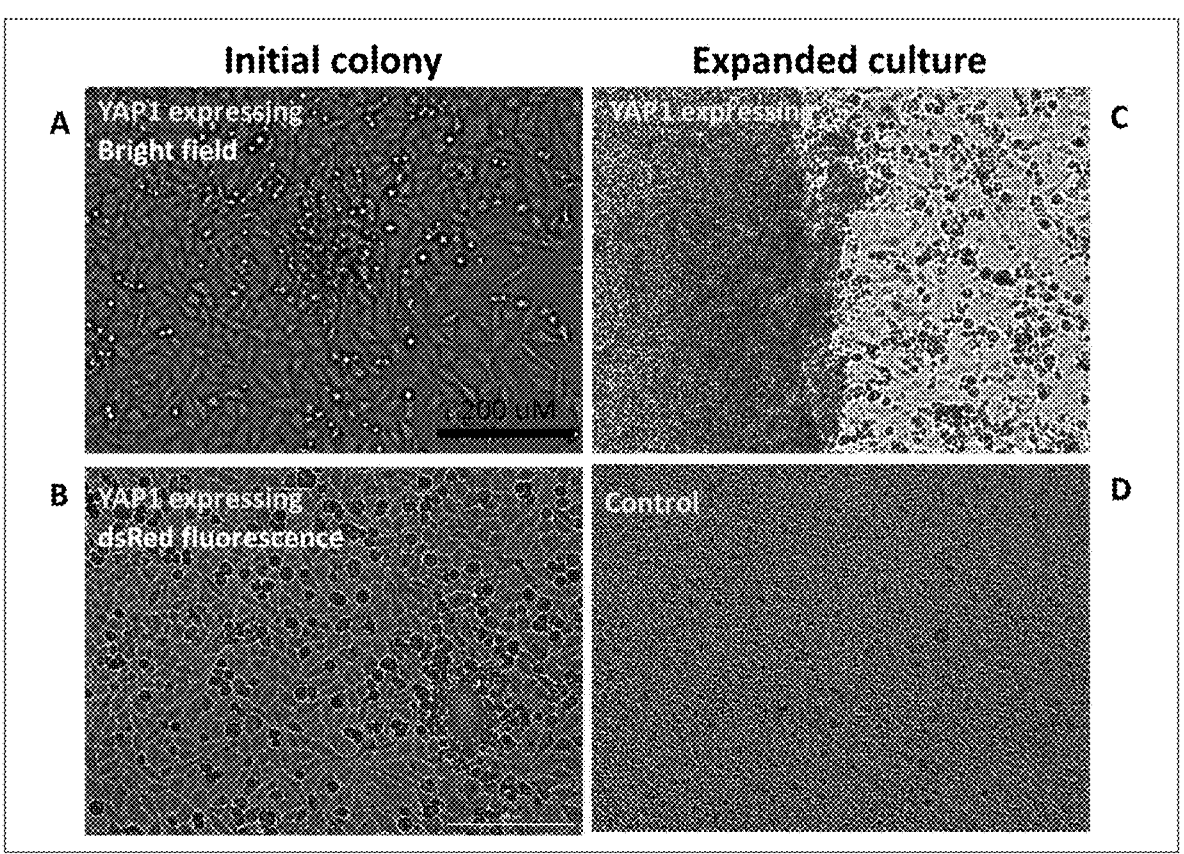
FIG. 7 shows images of chicken fibroblasts (DF1) transduced with a plasmid expressing constitutively active YAP1 and dsRed and untransfected fibroblasts (control). Panels A and B show the initial colonies (prior to expansion) of the cells transduced with the plasmid (A—under bright field setting, B—under fluorescent setting). Panels C and D show images of expanded colonies of fibroblasts transduced with the YAP1-dsRed plasmid (C) and untransfected fibroblasts (D).

Example 7: Expression of Constitutively Active YAP1 Increases the Culture Density and the Thickness of the Cellular Biomass Cells originating from a chicken fibroblast cell line, (DF1), were transduced with a plasmid expressing hYAP1, dsRed, and a neomycin resistance gene. Cells were selected for 8 days in the presence of G418, when dsRed positive colonies appeared in culture. Selected cells were plated in a 6 well plate and cultured for 3 weeks. As shown in FIG. 7, YAP1-expressing cells proliferated, showed loss of contact inhibition, and formed stratified multiple cell layers thereby increasing the culture density and the thickness of the initial cellular biomass when allowed to proliferate for 2 weeks after formation of a confluent monolayer. For example, in FIG. 7C, a large colony of stratified cells, as seen on the left side of image, boarders a monolayer of cells, as seen on the right side of the image. This characteristic colony-formation and cell stratification was observed only in DF1 cultures expressing ectopic YAP1. The initial thickness of the YAP1 expressing cultures was less than 20 μm and the thickness after expansion was 80 μm. In contrast, control cultures (untransfected cells) remained in a uniform monolayer. These results indicate that overexpression of YAP1 leads to loss of contact inhibition and increases the culture density and the thickness of cellular biomass.

Figure 17:
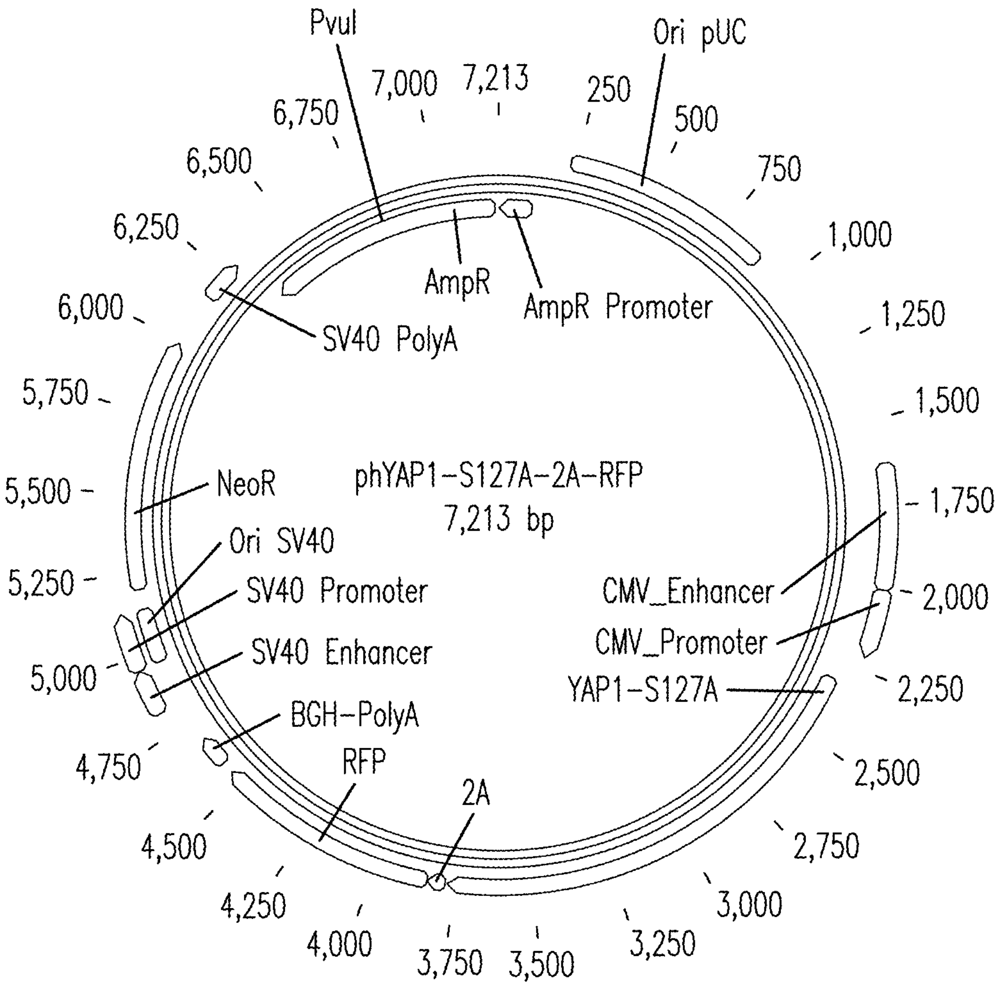
FIG. 17 shows a map of an exemplary plasmid containing a hYAP1 and RFP construct.
Figure 18:
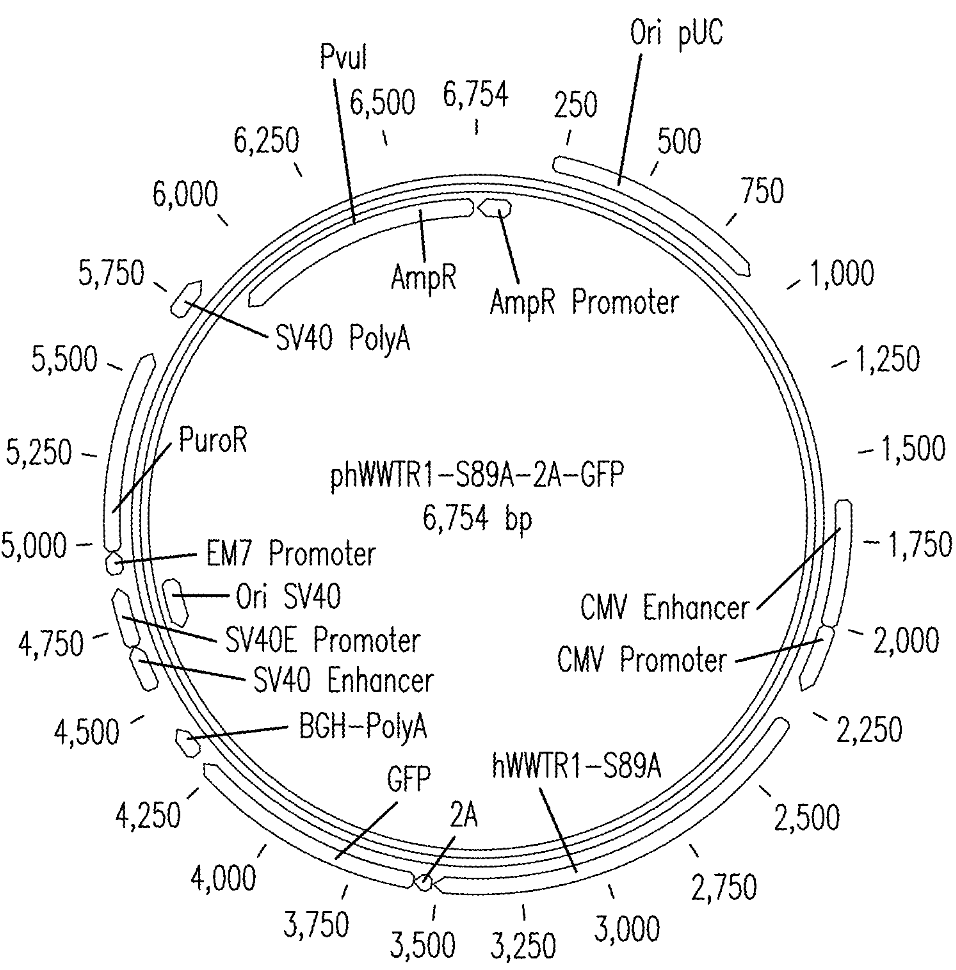
FIG. 18 shows a map of an exemplary plasmid containing a hWWTR1 and GFP construct.

In another experiment, the increase in the thickness of the cellular biomass was measured as follows. Isolated primary fibroblasts were transfected with a plasmid expressing hYAP1 and RFP. FIGS. 17 and 18 show maps of exemplary plasmids expressing (a) hYAP1 and RFP (FIG. 17) and (b) hWWTR1 (a gene encoding TAZ) and GFP (FIG. 18).

Figure 8:
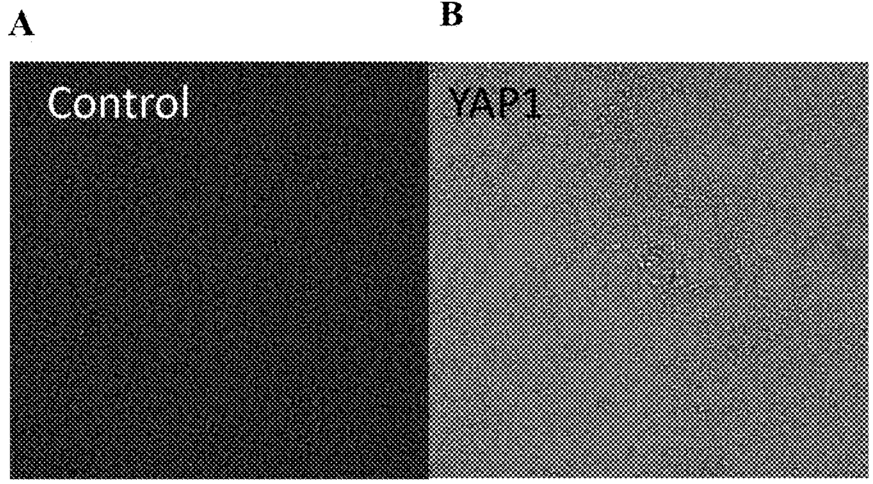
FIG. 8 shows the wild-type cell culture (A) and the culture of hYAP1 (human YAP1) expressing cells (B) on day 9.

Untransfected cells and hYAP1-RFP expressing cells were seeded at a density of $2.5\times10^5$ per well in a 6-well plate and allowed to grow for 9 days post-confluence. Colonies of varying thickness were observed in the well containing hYAP1-RFP expressing cells whereas the well containing untransfected, wild-type cells showed a monolayer growth. Images were captured using the ImageXpress Micro XLS Widefield High-Content analysis system. Z-stacks were obtained from the base of the cells to the top of the cells to include all the cells in the region of interest (ROI). The number of 2D images per z-stacks relies on the thickness of the cells being imaged and the step size. Previous studies have measured 3D cell thickness and volumes from single section information, from partial stacks or even from cell diameter. The hYAP1-RFP expressing cells formed colonies of cells that were thicker than a regular monolayer. This is indicative of a decrease in contact inhibition due to the overexpression of YAP1. FIG. 8 (panel A) shows the wild-type cell culture and panel B shows the culture of hYAP1 expressing cells. The thickness of wild-type and YAP1 expressing cellular biomass on day 9 of the culture was as follows:

TABLE 1

| Cell type | Thickness |
|---|---|
| Wild type | 6 μM |
| YAP1 expressing | 17 μM |

Example 8: Expression of Constitutively Active YAP1 Increases Cell Mass

Figure 9:
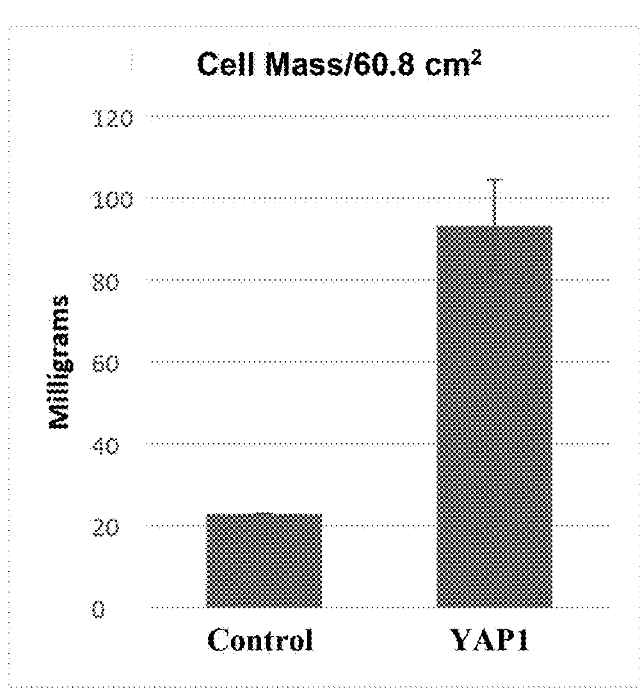
FIG. 9 shows the effect of constitutive expression of YAP1 on cell mass/60.8 $cm^2$ for wild-type cells vs. cells transduced hYAP1-RFP plasmid.

DF1 fibroblasts expressing hYAP1-RFP or wild type cells were plated at $5.5\times10^3$ cells per $cm^2$ in 10 cm tissue culture plates. After 11 days, the cultures were harvested using a cell scraper and a PBS rinse. The suspension was transferred into a 15 mL tube and centrifuged at 500 g for 5 minutes. The supernatant was aspirated and the wet cell mass was measured on an electronic scale. As shown in FIG. 9, wet cell mass/60.8 $cm^2$ of YAP1-expressing cells was significantly more (about 4.5 fold) than that of wild-type cells.

Example 9: YAP1 Expression in Cells Transfected with YAP1-dsRed Plasmid

Figure 10:
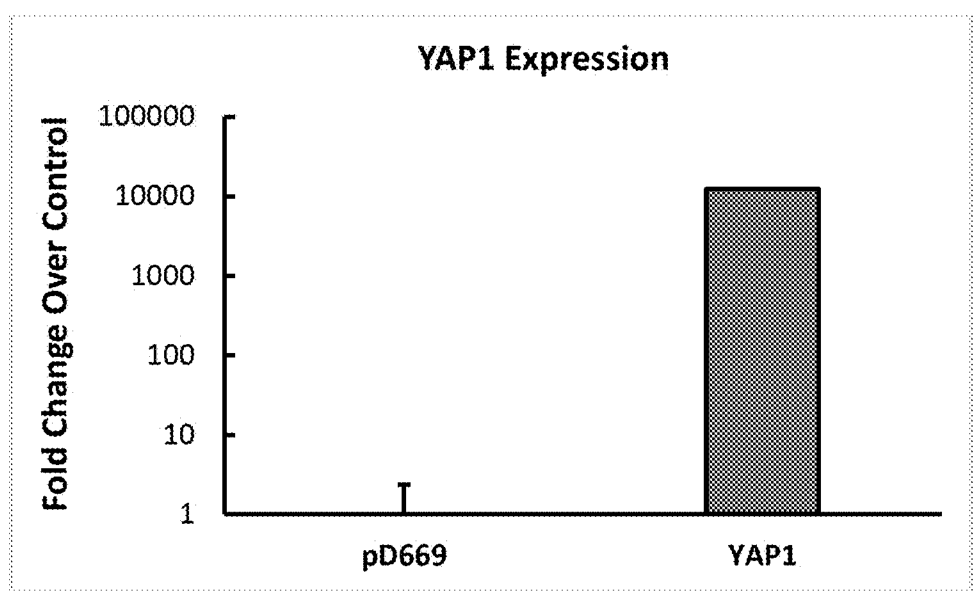
FIG. 10 shows the level of YAP1 mRNA in wild-type cells and cells transduced with hYAP1-dsRed plasmid and selected for dsRed.

Wild type and YAP1 transfected DF1 chicken fibroblast cells were cultured for 2 days and harvested using trypsin digestion. RNA was harvested using a commercially available RNA isolation kit Quick-RNA MiniPrep from Zymo Research). RNA was quantified using the NanoPhotometer (Implen). 250 ng of total RNA was used for a cDNA reaction using a commercially available reverse transcriptase kit (BioRad). 12.5 ng of cDNA was used for a qPCR reaction using the SsoAdvanced Universal Probes Supermix (Bio-Rad). Human YAP1 mRNA expression and chicken actin mRNA expression was quantified using a commercially available Taqman assay kits (ThermoFisher Scientific). The sequences for primers and probes used in this experiment are listed as SEQ ID NOs: 21-23. Relative gene expression analysis was carried out using the delta-delta Ct method. Cells transfected with hYAP1-dsRed plasmid show a high expression of hYAP1 mRNA (FIG. 10).

Figure 11:
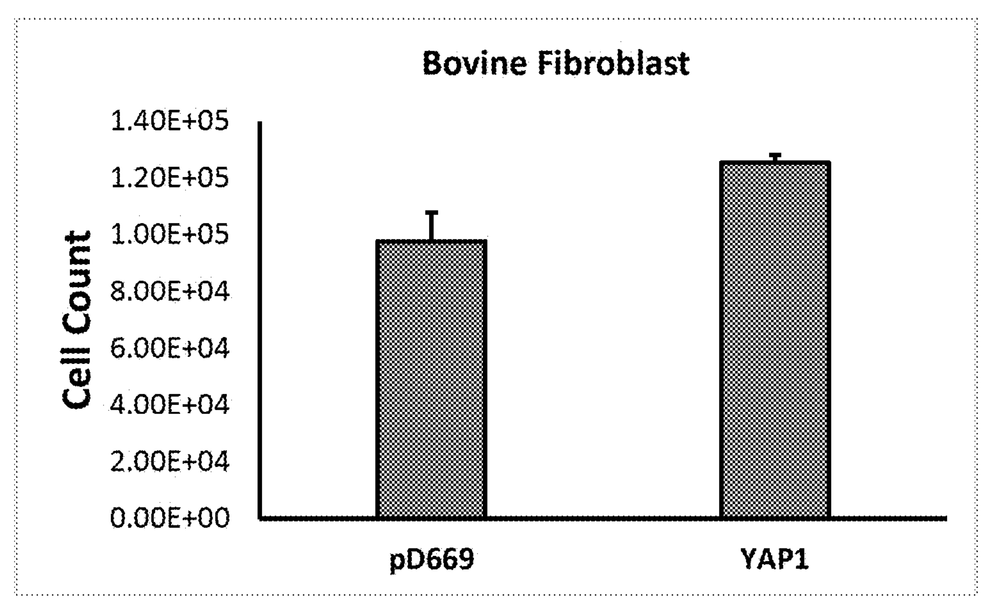
FIG. 11 shows that the expression of constitutively active YAP1 increases proliferation of primary bovine fibroblasts (A) and chicken fibroblasts (B).
Figure 11:
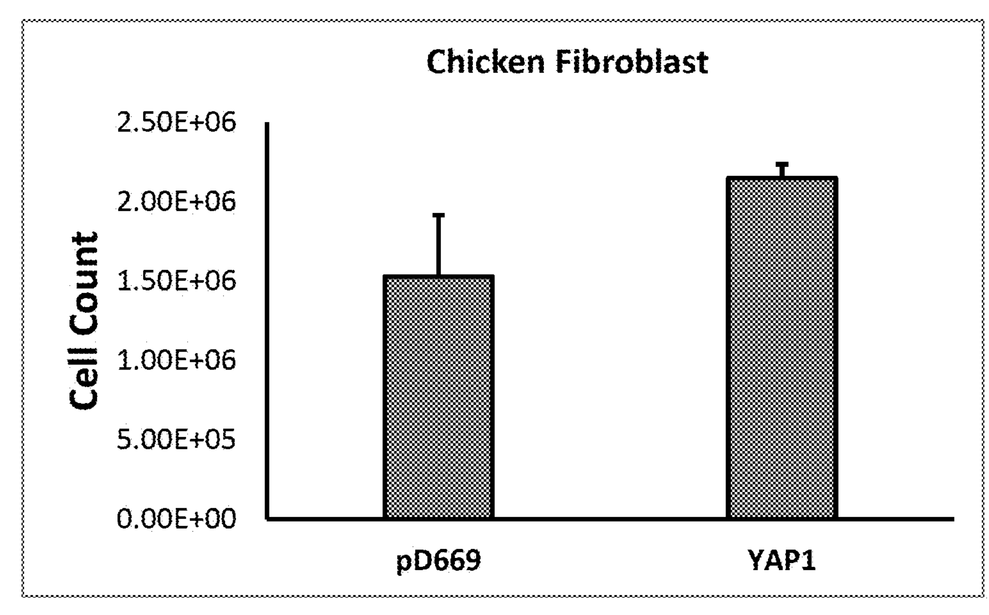

Example 10: Expression of Constitutively Active YAP1 Increases Cell Proliferation Primary bovine fibroblasts and chicken DF1 fibroblasts at a culture density of $1.5\times10^5$ per sample were transduced with a plasmid expressing hYAP1 and dsRed, with neomycin resistance gene. Cells were harvested after 72 hours and counted by the Trypan blue method on a hemacytometer. Cells transduced with YAP1 showed an increased growth rate (FIG. 11). Error bar indicates standard deviation. **=P<0.01*=P<0.05

Example 11: Expression of YAP1 Increases the Rate of Cell Proliferation

Figure 12:
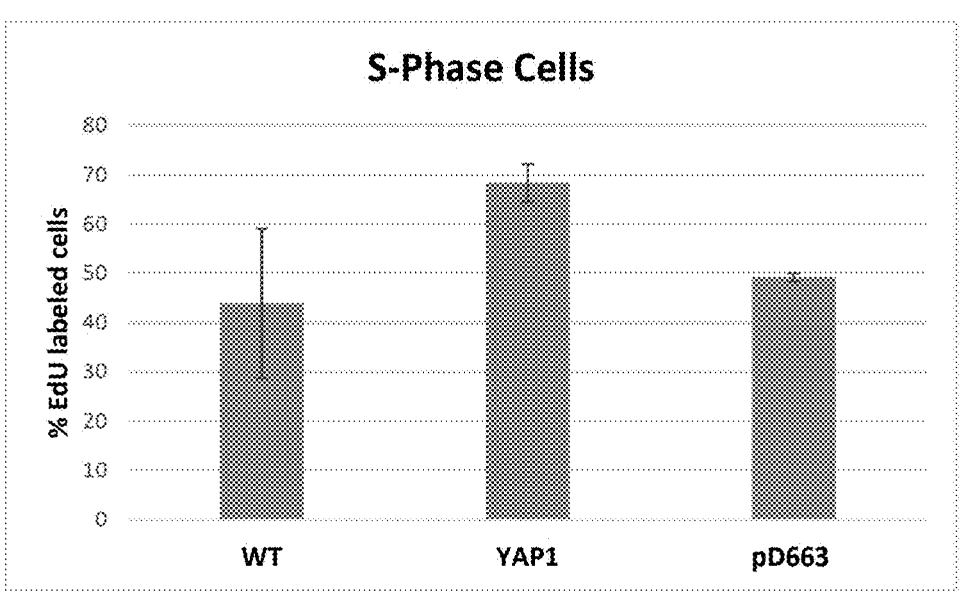
FIG. 12 shows that the expression of constitutively active YAP1 increases rate of cell proliferation. Panel A shows the rate of proliferation of wild-type DF1 cells (chicken fibroblast cell line); DF1 cells transfected with a hYAP1-RFP plasmid, and DF1 cells transfected with a control plasmid (pD663). Panel B shows a clear separation of proliferating cells that have incorporated EdU and non-proliferating cells that did not incorporate EdU.
Figure 12:
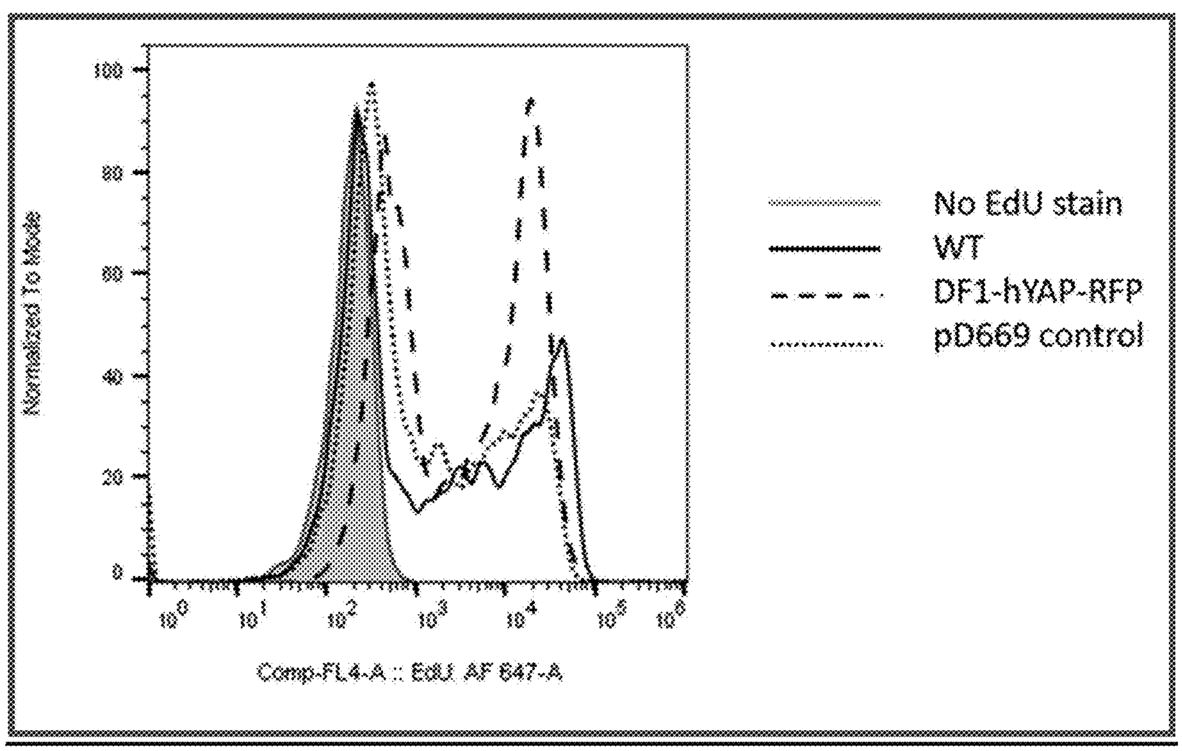

DF1 cells (chicken fibroblast cell line) were transduced with a hYAP1-RFP expressing plasmid or a control vector with dsRed (pD663). hYAP1-RFP expressing cells were selected by flow cytometric sorting based on the expression of dsRed from the hYAP1-RFP vector. Similarly, cells transduced with a control vector expressing dsRed, but no hYAP1 (pD663) were selected by flow cytometric sorting based on the expression of dsRed. The selected transduced cells were allowed to adhere for 24 hours, harvested, and seeded at a density of $1\times10^5$ cells per well in a 12 well plate. After 48 hours, the cells were treated with 3 μM EdU, incubated at room temperature for 6 hours and detected using the manufacturer's instructions. Cells were labeled with Alexa Fluor® 647 azide and analyzed by a FACS using 633 nm excitation and a 660/20 nm emission filter. YAP1-expressing cells have the highest number of cells in the S-phase, which is indicative of increased proliferation (FIG. 12A). The histogram in FIG. 12B shows a separation between cells which have incorporated EdU, indicative of proliferating cells vs. cells which did not incorporate EdU, indicative of non-proliferating cells.

Figure 13:
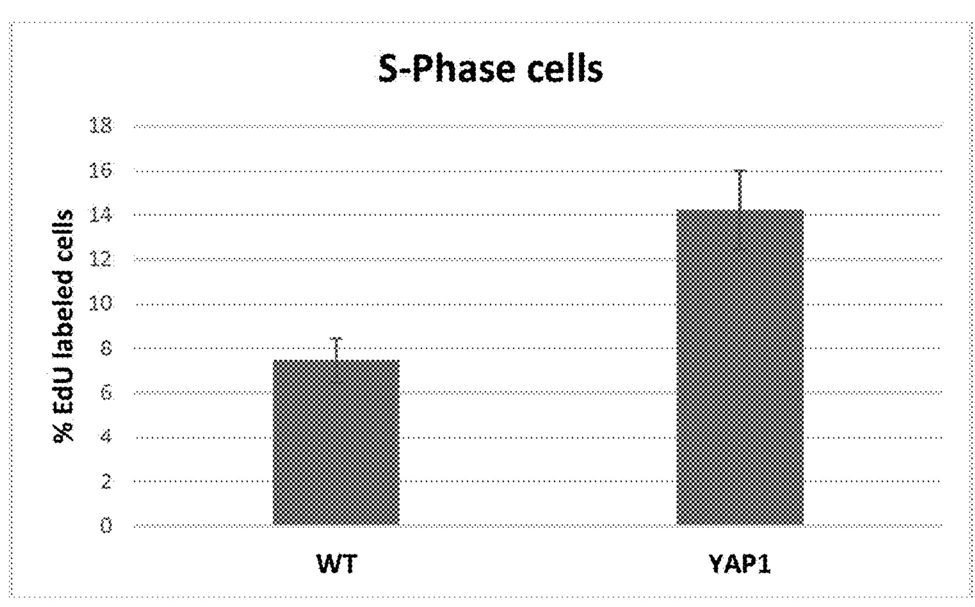
FIG. 13 shows that the ectopic expression of YAP1 in cells cultured in suspension induces cell proliferation.

Example 12: Expression of YAP1 Increases the Rate of Cell Proliferation in Suspension Cultures DF1 cells were transduced using the hYAP1-RFP plasmid and seeded at a density of $1\times10^4$ cells per well in a low binding plate (24-well). After 6 days, the cells were treated with 3 μM EdU, incubated at room temperature for 6 hours and detected according to the manufacturer's instructions. The cells were labeled with Alexa Fluor® 647 azide and analyzed using a FACS using 633 nm excitation and a 660/20 nm emission filter. Despite their native adherent characteristics, YAP1 expressing cells have a significantly higher number of cells in the S-phase (FIG. 13), which is indicative of increased proliferation and transition from anchorage-dependent to anchorage-independent growth in culture.

The invention claimed is:

1. A method for adapting anchorage-dependent cells to suspension culture, comprising:

a) providing anchorage-dependent cells comprising i) a nucleic acid encoding a YAP protein, operably linked to a regulatory sequence that promotes ectopic expression in the anchorage-dependent cells, or ii) a nucleic acid encoding a TAZ protein, operably linked to a regulatory sequence that promotes ectopic expression in the anchorage-dependent cells, wherein the anchorage-dependent cells are poultry or bovine fibroblast cells or poultry or bovine primary muscle-derived cells;

b) ectopically expressing the YAP protein or the TAZ protein in the anchorage-dependent cells in a suspension culture in a cultivation infrastructure which does not comprise a substrate to which cells can adhere, wherein the suspension culture comprises agitation to prevent sedimentation and aggregation, thereby adapting the anchorage-dependent cells to suspension culture to produce suspension-adapted cells which proliferate in the suspension culture;

c) isolating the proliferating suspension-adapted cells from the suspension culture; and d) culturing the isolated proliferating suspension-adapted cells in a second suspension culture to a density of about $10^5$ cells/mL to about $10^{10}$ cells/mL in at least 1000 L.

2. The method of claim 1, wherein isolating the proliferating suspension-adapted cells comprises clonal isolation.

3. The method of claim 1, wherein the anchorage-dependent cells are myogenic.

4. The method of claim 1, further comprising forming the isolated proliferating suspension-adapted cells from step (d) into a comestible food product.

5. The method of claim 1, further comprising forming the isolated proliferating suspension-adapted cells in step (d) into a self-adherent aggregate.

6. The method of claim 5, wherein the self-adherent aggregate forms from a clonally isolated cell growing in the suspension culture.

7. The method of claim 1, further comprising in step (b) inhibiting HIPPO signaling by contacting the anchorage-dependent cells with one or more of lysophosphatidic acid, sphingosine-1-phosphate, and thrombin.

8. The method of claim 1, wherein step (b) is in serum free media.

9. A method for adapting anchorage-dependent cells to suspension culture, comprising:

a) culturing the anchorage-dependent cells in a suspension culture in a cultivation infrastructure which does not comprise a substrate to which the cells can adhere and under conditions that inhibit HIPPO signaling in the anchorage-dependent cells, wherein the suspension culture comprises agitation to prevent sedimentation and aggregation, thereby adapting the anchorage-dependent cells to suspension culture to produce suspension-adapted cells which proliferate in the suspension culture, wherein the anchorage-dependent cells are poultry or bovine fibroblast cells or poultry or bovine primary muscle-derived cells, and wherein inhibiting HIPPO signaling comprises activating YAP and/or TAZ or homologs thereof, or inhibiting MOB1, LATS1 kinase, LATS2 kinase, WW45, MST1 kinase, and/or MST2 kinase or homologs thereof; and b) passaging the proliferating suspension-adapted cells in the suspension culture to another suspension culture, and growing the cells to a density of about $10^5$ cells/mL to about $10^{10}$ cells/mL in at least 1000 L.

10. The method of claim 9, further comprising clonally isolating a proliferating suspension-adapted cell from the suspension culture of step (a).

11. The method of claim 9, wherein the anchorage-dependent cells have been transfected with a construct comprising a nucleic acid encoding a YAP protein or a construct comprising a nucleic acid encoding a TAZ protein operably linked to a regulatory sequence that promotes ectopic expression in the anchorage-dependent cells, and wherein the YAP protein or the TAZ protein is ectopically expressed in the anchorage-dependent cells in step (a).

12. The method of claim 11, wherein the nucleic acid encoding the YAP protein or the nucleic acid encoding the TAZ protein is operably linked to a doxycycline-inducible promoter and the culturing of the anchorage-dependent cells is in the presence of doxycycline.

13. The method of claim 9, wherein step (a) is in serum free media.

14. The method of claim 11, wherein the regulatory sequence is an inducible promoter.

* * * * *